(12) United States Patent
Sauer et al.

(10) Patent No.: US 8,790,325 B2
(45) Date of Patent: Jul. 29, 2014

(54) DISPOSABLE WEARABLE ABSORBENT ARTICLES WITH ANCHORING SUBSYSTEMS

(75) Inventors: Andrew James Sauer, Cincinnati, OH (US); Michael Dale Trennepohl, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 933 days.

(21) Appl. No.: 11/899,812

(22) Filed: Sep. 7, 2007

(65) Prior Publication Data

US 2009/0069779 A1 Mar. 12, 2009

(51) Int. Cl.
*A61F 13/15* (2006.01)

(52) U.S. Cl.
USPC ............................... 604/385.22; 604/385.27

(58) Field of Classification Search
USPC ........................... 604/385.24–385.27, 385.22
See application file for complete search history.

(56) References Cited

U.S. PATENT DOCUMENTS

| | | |
|---|---|---|
| 84,703 A | 12/1868 | Moore |
| 1,155,659 A | 10/1915 | Johnson |
| 1,157,774 A | 10/1915 | Goodnou |
| 1,485,001 A | 2/1924 | Willis |
| 1,487,154 A | 3/1924 | Deloris et al. |
| 1,609,769 A | 12/1926 | Perlzweig |
| 1,661,936 A | 3/1928 | Ferstl |
| 1,705,194 A | 3/1929 | Marinsky |
| 1,756,508 A | 4/1930 | Bersin |
| 1,917,979 A | 7/1933 | Kelly |
| 2,025,843 A | 12/1935 | Anderson |
| 2,126,905 A | 8/1938 | Englander et al. |
| 2,413,970 A | 1/1947 | Hawley, Jr. |
| 2,493,113 A | 1/1950 | Dance |
| 2,572,331 A | 10/1951 | Gilessen |
| 2,652,058 A | 9/1953 | Carpenter |
| 2,699,171 A | 1/1955 | McWilliams |
| 3,441,025 A | 4/1969 | Ralph |
| 3,635,221 A | 1/1972 | Champaigne |
| 3,658,064 A | 4/1972 | Pociluyko |

(Continued)

FOREIGN PATENT DOCUMENTS

| | | |
|---|---|---|
| EP | 0323634 A2 | 12/1989 |
| EP | 0 858 787 | 8/1998 |

(Continued)

OTHER PUBLICATIONS

U.S. Appl. No. 12/204,844, filed Sep. 5, 2008, Andrew James Sauer.

(Continued)

*Primary Examiner* — Melanie Hand
(74) *Attorney, Agent, or Firm* — Kathleen Y. Carter; John G. Powell; Charles R. Ware

(57) ABSTRACT

The present disclosure includes an embodiment wherein a disposable wearable absorbent article comprises a side and an anchoring subsystem. The anchoring subsystem includes a first side anchoring member with a first middle, disposed along a first pathway, and a second side anchoring member with a second middle, disposed along a second pathway. At least a portion of the first middle is coextensive with at least a portion of the second middle, and at least a portion of the first pathway is distinct from at least a portion of the second pathway.

12 Claims, 37 Drawing Sheets

(56) References Cited

U.S. PATENT DOCUMENTS

| | | |
|---|---|---|
| 3,692,618 A | 9/1972 | Dorschner et al. |
| 3,802,817 A | 4/1974 | Matsuki et al. |
| 3,825,006 A | 7/1974 | Ralph |
| 3,848,594 A | 11/1974 | Buell |
| 3,860,003 A | 1/1975 | Buell |
| 3,911,173 A | 10/1975 | Sprague, Jr. |
| 3,929,135 A | 12/1975 | Thompson |
| 4,116,892 A | 9/1978 | Schwarz |
| 4,209,016 A | 6/1980 | Schaar |
| 4,315,508 A | 2/1982 | Bolick |
| 4,324,246 A | 4/1982 | Mullane et al. |
| 4,340,563 A | 7/1982 | Appel et al. |
| 4,342,314 A | 8/1982 | Radel et al. |
| 4,381,781 A | 5/1983 | Sciaraffa et al. |
| 4,463,045 A | 7/1984 | Ahr et al. |
| 4,515,595 A | 5/1985 | Kievit et al. |
| 4,573,986 A | 3/1986 | Minetola et al. |
| 4,609,518 A | 9/1986 | Curro et al. |
| 4,610,678 A | 9/1986 | Weisman et al. |
| 4,629,643 A | 12/1986 | Curro et al. |
| 4,655,760 A | 4/1987 | Morman et al. |
| 4,662,875 A | 5/1987 | Hirotsu et al. |
| 4,673,402 A | 6/1987 | Weisman et al. |
| 4,695,278 A | 9/1987 | Lawson |
| 4,699,621 A | 10/1987 | Stevens et al. |
| 4,701,171 A | 10/1987 | Boland et al. |
| 4,701,172 A | 10/1987 | Stevens |
| 4,701,173 A | 10/1987 | Zehner et al. |
| 4,701,174 A | 10/1987 | Johnson |
| 4,701,175 A | 10/1987 | Boland et al. |
| 4,710,189 A | 12/1987 | Lash |
| 4,718,900 A | 1/1988 | Boland et al. |
| 4,720,415 A | 1/1988 | VanderWielen et al. |
| 4,756,709 A | 7/1988 | Stevens |
| 4,770,656 A | 9/1988 | Proxmire et al. |
| 4,785,996 A | 11/1988 | Ziecker et al. |
| 4,795,454 A | 1/1989 | Dragoo |
| 4,808,178 A | 2/1989 | Aziz et al. |
| 4,816,025 A | 3/1989 | Foreman |
| 4,834,735 A | 5/1989 | Alemany et al. |
| 4,834,738 A | 5/1989 | Kielpikowski et al. |
| 4,834,741 A | 5/1989 | Sabee |
| 4,838,885 A | 6/1989 | Bernardin |
| 4,842,666 A | 6/1989 | Werenicz |
| 4,846,815 A | 7/1989 | Scripps |
| 4,850,990 A | 7/1989 | Huntoon et al. |
| 4,850,992 A | 7/1989 | Amaral et al. |
| 4,857,067 A | 8/1989 | Wood et al. |
| 4,865,823 A | 9/1989 | Minagawa et al. |
| 4,869,724 A | 9/1989 | Scripps |
| 4,888,231 A | 12/1989 | Angstadt |
| 4,892,536 A | 1/1990 | Desmarais et al. |
| 4,894,060 A | 1/1990 | Nestegard |
| 4,909,803 A | 3/1990 | Aziz et al. |
| 4,938,753 A | 7/1990 | Van Gompel et al. |
| 4,940,464 A | 7/1990 | Van Gompel et al. |
| 4,946,527 A | 8/1990 | Battrell |
| 4,962,571 A | 10/1990 | Visser |
| 4,963,140 A | 10/1990 | Robertson et al. |
| 4,968,312 A | 11/1990 | Khan |
| 4,988,344 A | 1/1991 | Reising et al. |
| 4,988,345 A | 1/1991 | Reising |
| 4,990,147 A | 2/1991 | Freeland |
| 4,995,873 A | 2/1991 | Knight |
| 5,006,394 A | 4/1991 | Baird |
| 5,026,364 A | 6/1991 | Robertson |
| 5,037,416 A | 8/1991 | Allen et al. |
| 5,062,840 A | 11/1991 | Holt et al. |
| 5,069,672 A | 12/1991 | Wippler |
| 5,077,868 A | 1/1992 | Visser |
| 5,092,861 A | 3/1992 | Nomura et al. |
| 5,137,537 A | 8/1992 | Herron et al. |
| 5,143,679 A | 9/1992 | Weber et al. |
| 5,147,345 A | 9/1992 | Young et al. |
| 5,151,092 A | 9/1992 | Buell et al. |
| 5,156,793 A | 10/1992 | Buell et al. |
| 5,167,897 A | 12/1992 | Weber et al. |
| 5,171,236 A | 12/1992 | Dreier et al. |
| 5,171,239 A | 12/1992 | Igaue et al. |
| 5,217,447 A | 6/1993 | Gagnon |
| 5,221,274 A | 6/1993 | Buell et al. |
| 5,246,433 A | 9/1993 | Hasse et al. |
| 5,260,345 A | 11/1993 | DesMarais et al. |
| 5,269,755 A | 12/1993 | Bodicky |
| 5,269,775 A | 12/1993 | Freeland et al. |
| 5,304,162 A | 4/1994 | Kuen |
| 5,306,266 A | 4/1994 | Freeland |
| 5,318,555 A | 6/1994 | Siebers et al. |
| 5,342,338 A | 8/1994 | Roe |
| 5,358,500 A | 10/1994 | LaVon et al. |
| 5,366,782 A | 11/1994 | Curro et al. |
| 5,374,262 A | 12/1994 | Keuhn et al. |
| 5,380,313 A | 1/1995 | Goulait et al. |
| 5,386,595 A | 2/1995 | Kuen et al. |
| 5,387,207 A | 2/1995 | Dyer et al. |
| 5,397,318 A | 3/1995 | Dreier |
| 5,399,177 A | 3/1995 | Blaney et al. |
| 5,405,682 A | 4/1995 | Shawyer et al. |
| 5,407,439 A | 4/1995 | Goulait |
| 5,411,498 A | 5/1995 | Fahrenkrug et al. |
| 5,422,172 A | 6/1995 | Wu |
| 5,423,789 A | 6/1995 | Kuen |
| 5,433,826 A | 7/1995 | Glomb et al. |
| 5,458,592 A | 10/1995 | Abuto et al. |
| 5,470,639 A | 11/1995 | Gessner et al. |
| 5,514,121 A | 5/1996 | Roe et al. |
| 5,518,801 A | 5/1996 | Chappell et al. |
| 5,540,671 A | 7/1996 | Dreier |
| 5,540,673 A | 7/1996 | Thomas et al. |
| 5,540,976 A | 7/1996 | Shawver et al. |
| 5,542,942 A | 8/1996 | Kline et al. |
| 5,554,142 A | 9/1996 | Dreier et al. |
| 5,554,145 A | 9/1996 | Roe et al. |
| 5,562,646 A | 10/1996 | Goldman et al. |
| 5,569,233 A | 10/1996 | Goulait |
| 5,569,234 A | 10/1996 | Buell et al. |
| 5,571,096 A | 11/1996 | Dobrin et al. |
| 5,580,411 A | 12/1996 | Nease et al. |
| 5,595,567 A | 1/1997 | King et al. |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |
| 5,620,431 A | 4/1997 | LeMahieu et al. |
| 5,622,589 A | 4/1997 | Johnson et al. |
| 5,624,427 A | 4/1997 | Bergman et al. |
| 5,625,222 A | 4/1997 | Yoneda et al. |
| 5,634,917 A | 6/1997 | Fujioka et al. |
| 5,635,191 A | 6/1997 | Roe et al. |
| 5,635,290 A | 6/1997 | Stopper et al. |
| 5,635,588 A | 6/1997 | Eshuis et al. |
| H1670 H | 7/1997 | Aziz et al. |
| 5,643,239 A | 7/1997 | Bodford et al. |
| 5,643,242 A | 7/1997 | LaVon et al. |
| 5,643,588 A | 7/1997 | Roe et al. |
| 5,650,222 A | 7/1997 | DesMarais et al. |
| 5,653,703 A | 8/1997 | Roe et al. |
| 5,662,638 A | 9/1997 | Johnson et al. |
| 5,669,894 A | 9/1997 | Goldman et al. |
| 5,669,897 A | 9/1997 | LaVon et al. |
| 5,669,900 A | 9/1997 | Bullwinkel et al. |
| 5,669,901 A | 9/1997 | LaFortune et al. |
| 5,674,216 A | 10/1997 | Buell et al. |
| 5,691,035 A | 11/1997 | Chappell et al. |
| 5,695,849 A | 12/1997 | Shawver et al. |
| 5,700,256 A | 12/1997 | Yamamoto et al. |
| 5,723,087 A | 3/1998 | Chappell et al. |
| 5,735,840 A | 4/1998 | Kline et al. |
| 5,749,865 A | 5/1998 | Yamamoto et al. |
| 5,772,825 A | 6/1998 | Schmitz |
| 5,776,123 A | 7/1998 | Goerg et al. |
| 5,779,831 A | 7/1998 | Schmitz |
| 5,797,824 A | 8/1998 | Tracy |
| 5,865,823 A | 2/1999 | Curro |

(56) References Cited

U.S. PATENT DOCUMENTS

| | | |
|---|---|---|
| 5,873,870 A | 2/1999 | Seitz et al. |
| 5,885,681 A | 3/1999 | Korpman |
| 5,891,544 A | 4/1999 | Chappell et al. |
| 5,897,545 A | 4/1999 | Kline et al. |
| 5,899,895 A * | 5/1999 | Robles et al. ............ 604/385.29 |
| 5,916,206 A | 6/1999 | Otsubo et al. |
| 5,916,661 A | 6/1999 | Benson et al. |
| 5,916,663 A | 6/1999 | Chappell et al. |
| 5,928,212 A | 7/1999 | Kline et al. |
| 5,938,648 A | 8/1999 | Lavon et al. |
| 5,941,864 A | 8/1999 | Roe |
| 5,941,865 A | 8/1999 | Otsubo et al. |
| 5,944,707 A | 8/1999 | Ronn |
| 5,947,944 A | 9/1999 | Hetzler et al. |
| 5,952,252 A | 9/1999 | Shawver et al. |
| 5,957,908 A | 9/1999 | Kline et al. |
| 5,997,521 A | 12/1999 | Robles et al. |
| 5,997,989 A | 12/1999 | Gessner et al. |
| 6,001,460 A | 12/1999 | Morman et al. |
| 6,004,306 A | 12/1999 | Robles et al. |
| 6,010,491 A | 1/2000 | Roe et al. |
| 6,013,589 A | 1/2000 | DesMarais et al. |
| 6,015,764 A | 1/2000 | Mccormack et al. |
| 6,027,483 A | 2/2000 | Chappell et al. |
| 6,042,673 A | 3/2000 | Johnson et al. |
| 6,096,668 A | 8/2000 | Abuto et al. |
| 6,103,647 A | 8/2000 | Shultz et al. |
| 6,107,537 A | 8/2000 | Elder et al. |
| 6,120,487 A | 9/2000 | Ashton |
| 6,120,489 A | 9/2000 | Johnson et al. |
| 6,132,409 A | 10/2000 | Vogt et al. |
| 6,156,424 A | 12/2000 | Taylor |
| 6,168,584 B1 | 1/2001 | Allen et al. |
| 6,168,585 B1 | 1/2001 | Cesco-Cancian |
| 6,169,151 B1 | 1/2001 | Waymouth et al. |
| 6,179,820 B1 | 1/2001 | Fernfors |
| 6,193,701 B1 | 2/2001 | Van Gompel et al. |
| 6,225,243 B1 | 5/2001 | Austin |
| 6,251,097 B1 | 6/2001 | Kline et al. |
| 6,264,641 B1 | 7/2001 | Van Gompel et al. |
| 6,303,208 B1 | 10/2001 | Pelkie |
| 6,306,121 B1 | 10/2001 | Damaghi et al. |
| 6,313,372 B1 | 11/2001 | Suzuki |
| 6,364,863 B1 | 4/2002 | Yamamoto et al. |
| 6,383,431 B1 | 5/2002 | Dobrin et al. |
| 6,413,249 B1 | 7/2002 | Turi et al. |
| 6,414,215 B1 | 7/2002 | Roe |
| 6,423,043 B1 | 7/2002 | Gustafsson |
| 6,432,098 B1 | 8/2002 | Kline et al. |
| 6,436,512 B1 | 8/2002 | Kauschke et al. |
| 6,437,214 B1 | 8/2002 | Everett et al. |
| 6,441,266 B1 | 8/2002 | Dyer et al. |
| 6,448,467 B1 | 9/2002 | Herrlein et al. |
| 6,465,073 B1 | 10/2002 | Morman et al. |
| 6,479,154 B1 | 11/2002 | Walton et al. |
| 6,482,191 B1 | 11/2002 | Roe et al. |
| 6,498,284 B1 | 12/2002 | Roe |
| 6,503,236 B1 | 1/2003 | Uitenbroek et al. |
| 6,518,378 B2 | 2/2003 | Waymouth et al. |
| 6,531,027 B1 | 3/2003 | Lender et al. |
| 6,547,774 B2 | 4/2003 | Ono et al. |
| 6,555,643 B1 | 4/2003 | Rieger |
| 6,559,262 B1 | 5/2003 | Waymouth et al. |
| 6,573,423 B1 | 6/2003 | Herrlein et al. |
| 6,579,274 B1 | 6/2003 | Morman et al. |
| 6,585,713 B1 | 7/2003 | LeMahieu et al. |
| 6,595,975 B2 | 7/2003 | Vogt et al. |
| 6,605,172 B1 | 8/2003 | Anderson et al. |
| 6,616,648 B2 | 9/2003 | Hermansson et al. |
| 6,623,468 B2 | 9/2003 | Shimoe |
| 6,623,837 B2 | 9/2003 | Morman et al. |
| 6,627,564 B1 | 9/2003 | Morman et al. |
| 6,632,211 B2 | 10/2003 | Otsubo |
| 6,641,568 B2 | 11/2003 | Ashton et al. |
| 6,667,258 B2 | 12/2003 | Quinn |
| 6,677,258 B2 | 1/2004 | Carroll et al. |
| 6,680,265 B1 | 1/2004 | Smith et al. |
| 6,680,422 B2 | 1/2004 | Roe |
| 6,717,028 B1 | 4/2004 | Oberstadt |
| 6,726,792 B1 | 4/2004 | Johnson et al. |
| 6,746,434 B2 | 6/2004 | Johnson et al. |
| 6,811,865 B2 | 11/2004 | Morman et al. |
| 6,811,871 B2 | 11/2004 | Sen et al. |
| 6,827,806 B2 | 12/2004 | Uitenbroek et al. |
| 6,843,134 B2 | 1/2005 | Anderson et al. |
| 6,849,324 B2 | 2/2005 | Meece et al. |
| 6,875,710 B2 | 4/2005 | Eaton et al. |
| 6,896,843 B2 | 5/2005 | Topolkaraev et al. |
| 6,909,028 B1 | 6/2005 | Shawver et al. |
| 6,915,700 B2 | 7/2005 | Anderson et al. |
| 6,942,894 B2 | 9/2005 | Alberg et al. |
| 7,013,941 B2 | 3/2006 | Schneider et al. |
| 7,024,939 B2 | 4/2006 | Anderson et al. |
| 7,028,735 B2 | 4/2006 | Schneider et al. |
| 7,056,411 B2 | 6/2006 | Desai et al. |
| 7,062,983 B2 | 6/2006 | Anderson et al. |
| 7,066,921 B2 | 6/2006 | Schmoker et al. |
| 7,087,287 B2 | 8/2006 | Curro et al. |
| 7,094,227 B2 | 8/2006 | Ishguro et al. |
| 7,122,022 B2 | 10/2006 | Drevik |
| 7,223,818 B2 | 5/2007 | Autran et al. |
| 7,744,579 B2 | 6/2010 | Langdon et al. |
| 2001/0023341 A1 | 9/2001 | Karami |
| 2001/0041879 A1 | 11/2001 | Karami et al. |
| 2001/0042584 A1 | 11/2001 | Karami et al. |
| 2002/0002021 A1 | 1/2002 | May et al. |
| 2002/0007164 A1 | 1/2002 | Boggs et al. |
| 2002/0010455 A1 | 1/2002 | Hermansson et al. |
| 2002/0035354 A1 | 3/2002 | Mirle et al. |
| 2002/0045879 A1 | 4/2002 | Karami |
| 2002/0111598 A1 | 8/2002 | Vogt et al. |
| 2002/0138065 A1 | 9/2002 | Yeater |
| 2002/0151858 A1 | 10/2002 | Karami et al. |
| 2003/0021951 A1 | 1/2003 | Desai et al. |
| 2003/0065298 A1 | 4/2003 | Mirle et al. |
| 2003/0078558 A1 | 4/2003 | Karami et al. |
| 2003/0084996 A1 | 5/2003 | Alberg et al. |
| 2003/0087059 A1 | 5/2003 | Jackson et al. |
| 2003/0087098 A1 | 5/2003 | Eaton et al. |
| 2003/0088220 A1 | 5/2003 | Molander et al. |
| 2003/0088228 A1 | 5/2003 | Desai et al. |
| 2003/0091807 A1 | 5/2003 | Desai et al. |
| 2003/0109842 A1 | 6/2003 | Louis et al. |
| 2003/0144645 A1 | 7/2003 | Karami |
| 2003/0162458 A1 | 8/2003 | Tsujiyama et al. |
| 2003/0220626 A1 | 11/2003 | Karami |
| 2003/0225382 A1 | 12/2003 | Tombult-Meyer et al. |
| 2003/0233082 A1 | 12/2003 | Kline et al. |
| 2004/0006326 A1 | 1/2004 | Nakajima et al. |
| 2004/0024109 A1 | 2/2004 | Hamersky et al. |
| 2004/0049836 A1 | 3/2004 | Ashraf et al. |
| 2004/0082933 A1 | 4/2004 | Karami |
| 2004/0092677 A1 | 5/2004 | Hanke et al. |
| 2004/0110442 A1 | 6/2004 | Rhim et al. |
| 2004/0121687 A1 | 6/2004 | Morman et al. |
| 2004/0121690 A1 | 6/2004 | Mleziva |
| 2004/0132374 A1 | 7/2004 | Kobayashi |
| 2004/0153043 A1 | 8/2004 | Sugito et al. |
| 2004/0162536 A1 | 8/2004 | Becker et al. |
| 2004/0167486 A1 | 8/2004 | Busam et al. |
| 2004/0173036 A1 | 9/2004 | Anderson et al. |
| 2004/0193133 A1 | 9/2004 | Desai et al. |
| 2004/0193134 A1 | 9/2004 | Mueller et al. |
| 2004/0222553 A1 | 11/2004 | Desai et al. |
| 2004/0224132 A1 | 11/2004 | Roe et al. |
| 2005/0070866 A1 | 3/2005 | Isele et al. |
| 2005/0096624 A1 | 5/2005 | Hoshino et al. |
| 2005/0106980 A1 | 5/2005 | Abed et al. |
| 2005/0124952 A1 | 6/2005 | Zehner et al. |
| 2005/0130544 A1 | 6/2005 | Cheng et al. |
| 2005/0154366 A1 | 7/2005 | Karami et al. |
| 2005/0164586 A1 | 7/2005 | Autran et al. |
| 2005/0165173 A1 | 7/2005 | Autran et al. |
| 2005/0177123 A1 | 8/2005 | Catalan |

(56) References Cited

U.S. PATENT DOCUMENTS

| | | |
|---|---|---|
| 2005/0211368 A1 | 9/2005 | McGuire et al. |
| 2005/0214461 A1 | 9/2005 | Desai et al. |
| 2005/0215963 A1 | 9/2005 | Autran et al. |
| 2005/0215964 A1 | 9/2005 | Autran et al. |
| 2005/0215972 A1 | 9/2005 | Roe et al. |
| 2005/0215973 A1 | 9/2005 | Roe et al. |
| 2005/0256476 A1 | 11/2005 | Mirle et al. |
| 2005/0273072 A1 | 12/2005 | Hird et al. |
| 2006/0014460 A1 | 1/2006 | Isele et al. |
| 2006/0129119 A1 | 6/2006 | Kistler |
| 2006/0141883 A1 | 6/2006 | Nishiguchi et al. |
| 2006/0155253 A1 | 7/2006 | Dziezok et al. |
| 2006/0155254 A1 | 7/2006 | Dziezok et al. |
| 2006/0189956 A1 | 8/2006 | Catalan |
| 2007/0078427 A1 | 4/2007 | Raycheck et al. |
| 2007/0093769 A1 | 4/2007 | Kline et al. |
| 2007/0142815 A1 | 6/2007 | Macura et al. |
| 2007/0202767 A1 | 8/2007 | Anderson et al. |
| 2007/0287348 A1 | 12/2007 | Autran et al. |
| 2007/0287981 A1 | 12/2007 | Roe et al. |
| 2007/0287982 A1 | 12/2007 | Lodge et al. |
| 2007/0287983 A1 | 12/2007 | Lodge et al. |
| 2008/0004582 A1 | 1/2008 | Lodge et al. |
| 2008/0004583 A1 | 1/2008 | Desai et al. |
| 2008/0004584 A1 | 1/2008 | Langdon et al. |
| 2008/0004586 A1 | 1/2008 | Lodge et al. |
| 2008/0004587 A1 | 1/2008 | Lodge et al. |
| 2008/0004589 A1 | 1/2008 | Roe et al. |
| 2008/0004590 A1 | 1/2008 | Lodge et al. |
| 2008/0004591 A1 | 1/2008 | Desai et al. |
| 2008/0004592 A1 | 1/2008 | Lodge et al. |
| 2008/0004593 A1 | 1/2008 | Lodge et al. |
| 2008/0015537 A1 | 1/2008 | Lodge et al. |
| 2008/0045917 A1 | 2/2008 | Autran |
| 2008/0114326 A1 | 5/2008 | Roe et al. |
| 2008/0125739 A1 | 5/2008 | Lodge et al. |
| 2008/0188822 A1 | 8/2008 | Lodge et al. |

FOREIGN PATENT DOCUMENTS

| | | | |
|---|---|---|---|
| EP | 1350493 A1 | 10/2003 | |
| EP | 1 787 610 | 5/2007 | |
| EP | 1787610 A1 * | 5/2007 | .............. A61F 13/15 |
| GB | 243 719 | 2/1926 | |
| WO | WO 95/16746 A1 | 6/1995 | |
| WO | WO 96/35402 A1 | 11/1996 | |
| WO | WO 98/48750 | 11/1998 | |
| WO | WO 03039421 A | 5/2003 | |
| WO | WO 2005/065680 A1 | 7/2005 | |
| WO | WO 2006/017518 A2 | 2/2006 | |
| WO | WO 2006/017518 A3 | 2/2006 | |
| WO | WO 2006/017674 A1 | 2/2006 | |

OTHER PUBLICATIONS

U.S. Appl. No. 12/204,849, filed Sep. 5, 2008, Andrew James Sauer.
U.S. Appl. No. 12/204,854, filed Sep. 5, 2008, Andrew James Sauer.
U.S. Appl. No. 12/204,858, filed Sep. 5, 2008, Andrew James Sauer.
U.S. Appl. No. 12/204,864, filed Sep. 5, 2008, Andrew James Sauer.

* cited by examiner

Fig. 11E

| | Fig. 11E-A |
|---|---|
| | Fig. 11E-B |
| | Fig. 11E-C |

Fig. 11E-A

| | C1 | C2 | C3 | C4 | C5 | C6 | C7 | C8 | C9 | C10 | C11 | C12 | C13 | C14 | C15 | C16 | C17 |
|---|---|---|---|---|---|---|---|---|---|---|---|---|---|---|---|---|---|
| R1 | 2.32 | 2.61 | 0.78 | 0.26 | 0.31 | 0.31 | 0.27 | 0.31 | 0.52 | 0.37 | 0.37 | 0.22 | 0.21 | 0.34 | 0.28 | 0.30 | 1.62 |
| R2 | 0.87 | 2.86 | 0.89 | 0.31 | 0.18 | 0.37 | 0.26 | 0.46 | 1.10 | 0.56 | 0.56 | 0.24 | 0.25 | 0.31 | 0.30 | 0.40 | 1.43 |
| R3 | 1.84 | 2.62 | 0.50 | 0.37 | 0.29 | 0.19 | 0.36 | 0.28 | 1.89 | 0.50 | 0.50 | 0.24 | 0.27 | 0.32 | 0.31 | 0.46 | 1.32 |
| R4 | 1.75 | 2.20 | 1.02 | 0.41 | 0.26 | 0.40 | 0.23 | 0.39 | 1.71 | 0.45 | 0.45 | 0.29 | 0.28 | 0.39 | 0.37 | 0.45 | 1.70 |
| R5 | 1.95 | 1.84 | 0.95 | 0.44 | 0.32 | 0.36 | 0.40 | 0.84 | 1.89 | 0.46 | 0.46 | 0.23 | 0.34 | 0.40 | 0.28 | 0.40 | 2.05 |
| R6 | 1.89 | 2.42 | 0.55 | 0.41 | 0.34 | 0.26 | 0.32 | 0.52 | 2.91 | 0.36 | 0.36 | 0.26 | 0.26 | 0.36 | 0.25 | 0.33 | 2.32 |
| R7 | 2.17 | 2.80 | 0.49 | 0.30 | 0.31 | 0.29 | 0.30 | 0.39 | 3.90 | 0.43 | 0.43 | 0.30 | 0.24 | 0.32 | 0.23 | 0.30 | 2.20 |
| R8 | 2.40 | 2.65 | 0.51 | 0.46 | 0.27 | 0.39 | 0.30 | 0.39 | 3.54 | 0.45 | 0.45 | 0.36 | 0.32 | 0.35 | 0.44 | 0.52 | 2.21 |
| R9 | 2.50 | 2.36 | 0.62 | 0.55 | 0.57 | 0.41 | 0.32 | 0.61 | 3.74 | 0.61 | 0.61 | 0.30 | 0.44 | 0.44 | 0.54 | 0.51 | 1.70 |
| R10 | 2.48 | 2.49 | 0.55 | 0.61 | 0.55 | 0.56 | 0.45 | 0.77 | 3.03 | 0.65 | 0.65 | 0.60 | 0.45 | 0.58 | 0.56 | 0.55 | 1.94 |

Fig. 11E-B

| | | | | | | | | | | | | | | | | | |
|---|---|---|---|---|---|---|---|---|---|---|---|---|---|---|---|---|---|
| R11 | 2.44 | 2.56 | 0.58 | 0.62 | 0.64 | 0.55 | 0.63 | 0.98 | 1.88 | 0.63 | 0.63 | 0.59 | 0.64 | 0.55 | 0.65 | 0.52 | 2.65 |
| R12 | 2.41 | 2.82 | 0.63 | 0.62 | 0.62 | 0.56 | 0.51 | 0.87 | 2.28 | 0.76 | 0.66 | 0.54 | 0.50 | 0.39 | 0.42 | 0.58 | 2.53 |
| R13 | 2.84 | 2.94 | 0.62 | 0.50 | 0.65 | 0.62 | 0.59 | 0.82 | 4.20 | 0.71 | 0.71 | 0.50 | 0.46 | 0.26 | 0.30 | 0.33 | 2.00 |
| R14 | 3.00 | 2.51 | 0.51 | 0.44 | 0.41 | 0.47 | 0.52 | 1.46 | 3.91 | 0.83 | 0.73 | 0.53 | 0.51 | 0.30 | 0.37 | 0.38 | 1.97 |
| R15 | 2.45 | 2.70 | 0.51 | 0.41 | 0.43 | 0.54 | 0.60 | 1.16 | 3.86 | 0.61 | 0.61 | 0.51 | 0.57 | 0.54 | 0.49 | 0.52 | 1.81 |
| R16 | 2.27 | 2.59 | 0.49 | 0.39 | 0.45 | 0.52 | 0.60 | 1.73 | 3.86 | 0.63 | 0.63 | 0.52 | 0.52 | 0.65 | 0.62 | 0.56 | 1.62 |
| R17 | 2.40 | 2.24 | 0.49 | 0.42 | 0.59 | 0.55 | 0.48 | 1.02 | 2.19 | 0.54 | 0.54 | 0.33 | 0.46 | 0.45 | 0.52 | 0.55 | 1.21 |
| R18 | 2.16 | 2.07 | 0.62 | 0.54 | 0.51 | 0.54 | 0.45 | 1.08 | 0.89 | 0.26 | 0.26 | 0.30 | 0.39 | 0.24 | 0.41 | 0.49 | 1.50 |
| R19 | 1.83 | 2.00 | 0.81 | 0.58 | 0.53 | 0.55 | 0.39 | 0.38 | | | | 0.31 | 0.32 | 0.31 | 0.28 | 0.45 | 0.95 |
| R20 | 1.20 | 1.70 | 0.69 | 0.60 | 0.45 | 0.43 | 0.21 | | | | | | | | 0.23 | 0.37 | 0.88 |
| R21 | 1.97 | 1.55 | 0.80 | 0.53 | 0.32 | 0.32 | 0.14 | | | | | | | | | 0.52 | 0.61 |

Fig. 11E-C

| | | | | | | | | | | | |
|---|---|---|---|---|---|---|---|---|---|---|---|
| R22 | 2.07 | 0.67 | 0.65 | 0.46 | 0.28 | 0.29 | | | | | |
| R23 | 1.65 | 0.70 | 0.53 | 0.28 | 0.32 | 0.28 | | | | | |
| R24 | 1.10 | 0.52 | 0.36 | 0.27 | 0.24 | 0.25 | | | | | |
| R25 | 1.52 | 0.59 | 0.29 | 0.45 | 0.36 | | | | | | |
| R26 | 2.43 | 0.68 | 0.23 | 0.33 | | | | | | | |
| R27 | 2.66 | | | | | | | | | | |

DISPOSABLE WEARABLE ABSORBENT ARTICLES WITH ANCHORING SUBSYSTEMS

FIELD OF THE INVENTION

In general, embodiments of the present disclosure relate to disposable wearable absorbent articles. In particular, embodiments of the present disclosure relate to disposable wearable absorbent articles with anchoring subsystems.

BACKGROUND OF THE INVENTION

Disposable wearable absorbent articles include disposable diapers and disposable incontinence undergarments. A disposable wearable absorbent article can receive and contain bodily waste while being worn by a wearer. Such articles can be made with various materials in a number of configurations. The design of a disposable wearable absorbent article can affect the way that the article fits on a wearer. Unfortunately, some disposable wearable absorbent articles fit wearers poorly. As an example, some disposable wearable absorbent articles can sag or slip down on a wearer. A disposable wearable absorbent article that sags or slips down on a wearer can feel uncomfortable, look unattractive, and perform poorly as the article tends to leak.

BRIEF DESCRIPTION OF THE DRAWINGS

FIG. 11E illustrates an exemplary chart with modulus of elasticity values, obtained from the modulus mapping method testing and recorded for each square of the map of the embodiment of FIG. 11B, according to embodiments of the present disclosure.

DETAILED DESCRIPTION OF THE INVENTION

Figure 1A:
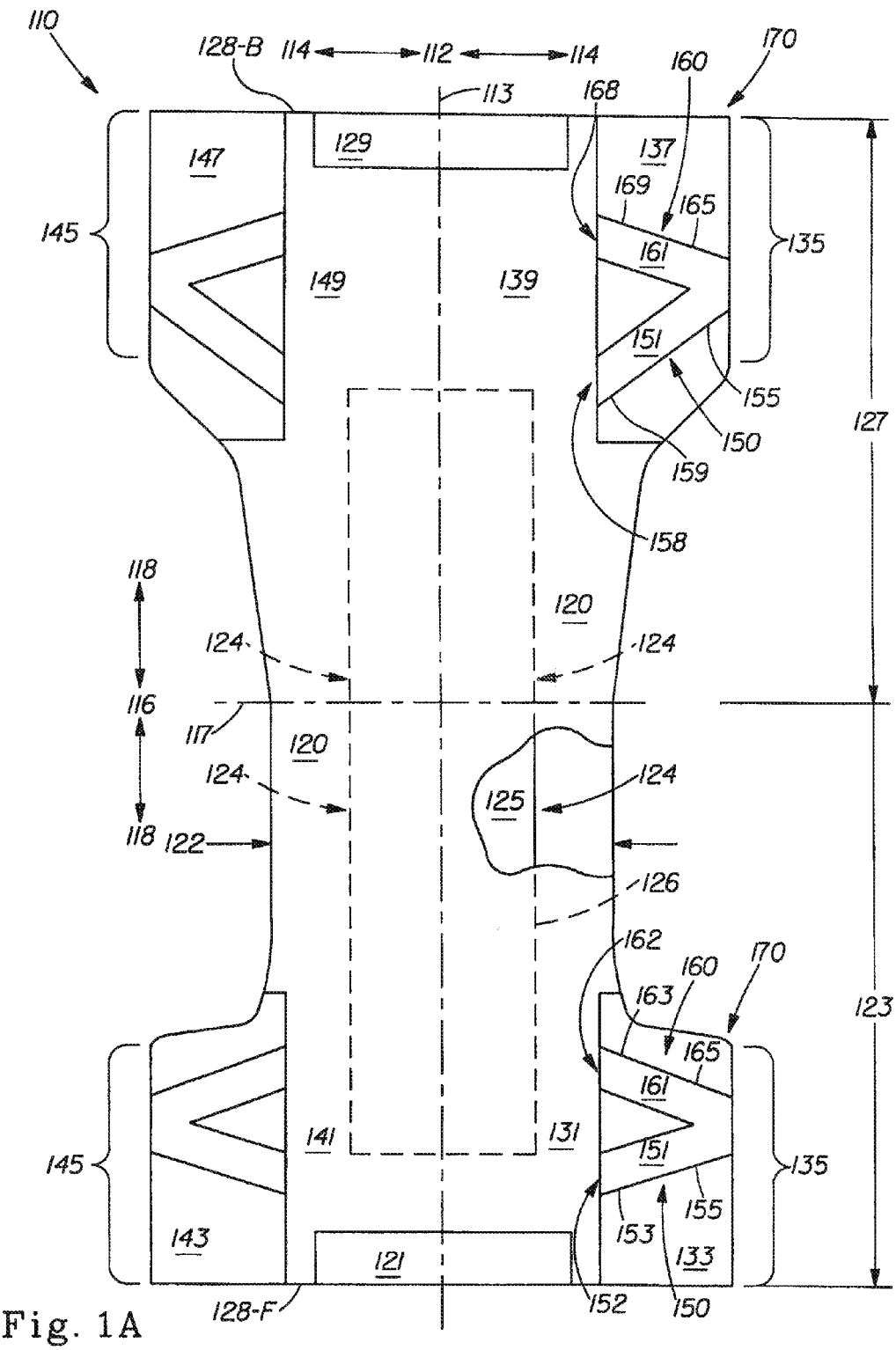
FIG. 1A illustrates a plan view of an inside of a pant-type disposable wearable absorbent article, including an anchoring subsystem with crossing side anchoring members, according to embodiments of the present disclosure.

Embodiments of the present disclosure include disposable wearable absorbent articles with anchoring subsystems that fit wearers well. The designs of these articles help prevent the articles from sagging or slipping down on a wearer. As a result, the disposable wearable absorbent articles of the present disclosure can feel comfortable, look attractive, and perform well as the articles tend to stay in place on wearers and not leak.

Embodiments of the present disclosure include disposable wearable absorbent articles. Throughout the present disclosure, the term "disposable wearable absorbent article" refers to an article, configured to be worn on a lower torso of a human body of a wearer, configured to receive and contain bodily exudates (e.g., urine and feces) from the body, and configured to be partly or wholly disposed of after a single use by the wearer. Thus, a disposable wearable absorbent article is configured such that the soiled article, or a soiled portion of the article, is not intended to be restored and reused (e.g., not intended to be laundered). Examples of disposable wearable absorbent articles include disposable diapers, disposable incontinence undergarments, etc. A disposable wearable absorbent article can be configured in various ways, such as a pant-type configuration or a fastenable configuration.

In embodiments of the present disclosure, a disposable wearable absorbent article can include an absorbent core. Throughout the present disclosure, the term "absorbent core" refers to a part of a disposable wearable absorbent article configured to absorb bodily exudates received into the article from a body of a wearer. An absorbent core can be configured in various ways, as will be understood by one of ordinary skill in the art. Examples of absorbent cores include absorbent core assemblies (with one or more optional core structures), bucket-shaped absorbent cores, removable and/or replaceable absorbent cores, etc.

When a disposable wearable absorbent article is placed on a wearer, the article is placed in an initial position with respect to the wearer. The location of this initial position can depend on a number of factors, such as the size of the article, the shape of the wearer's body, and the manner in which the article is placed on the wearer. For example, an initial position of a fastenable diaper can depend in part on a location at which the diaper is fastened around a wearer. However, as a disposable wearable absorbent article is worn by a wearer, a number of forces can act upon the article.

Some of these forces can tend to move the article on the wearer. Throughout the present disclosure, the term "load" refers to a force that tends to move a disposable wearable absorbent article out of place on a wearer. First, a disposable wearable absorbent article can experience various loads from placement of the article on a wearer. As an example, some pretension forces from fastening the article can drive the article downward. Second, a disposable wearable absorbent article can experience various loads from the article's environment. A wearer's clothes can pull on the article, for example. Third, a disposable wearable absorbent article can experience various loads from a wearer's movements. For example, as a wearer changes positions or moves about, the wearer's body can push against parts of the article or create dynamic forces in the article. Fourth, the force of gravity can move a disposable wearable absorbent article down on a wearer. The article can experience a significant load from the force of gravity, due to a mass of the article as well as a mass of any bodily waste contained by the article. These loads, can act upon a disposable wearable absorbent article, tending to move the article on a wearer.

However, other forces acting upon a disposable wearable absorbent article can tend to hold the article in place on a wearer. First, a disposable wearable absorbent article can experience various holding forces from placement of the article on a wearer. As an example, other pretension forces from fastening the article can drive the article upward. Second, parts of a disposable wearable absorbent article can experience friction forces from contact with a wearer's skin. For example, the article can experience a friction force where a waistband of the article wraps around and against the wearer's waist. Third, parts of a disposable wearable absorbent article can experience reaction forces from contact with various external anatomical features on a wearer's body. As an example, the article can experience reaction forces where the article contacts protruding portions of the wearer's hips. In this example, the reaction forces react against the force of gravity by pushing up on the article. These holding forces can act upon a disposable wearable absorbent article, tending to hold the article in place on a wearer.

As some forces tend to move a disposable wearable absorbent article down on a wearer and other forces tend to hold the article up on the wearer, part or all of the article may or may not move, depending on whether or not such forces are balanced. If the forces tending to hold the article up can equal the forces tending to move the article down, then the article can hold in place on the wearer. If the forces tending to move the article down are greater than the forces tending to hold the article up, then part or all of the article can move down on the wearer. Sometimes, forces can move down part or all of disposable wearable absorbent article, resulting in sagging and/or slipping.

However, embodiments of the present disclosure can help prevent disposable wearable absorbent articles from sagging or slipping down on a wearer. A disposable wearable absorbent article can include an anchoring subsystem. In various embodiments, an anchoring subsystem can be configured to collect at least some of the loads acting upon the article. The anchoring subsystem can also be configured to anchor itself to a body of a wearer. In this way, the anchoring subsystem can balance at least some of the collected loads with holding forces obtained from the anchoring. By balancing the collected loads with the obtained holding forces, the anchoring subsystem can at least assist in holding the disposable wearable absorbent article in place on a wearer.

An anchoring subsystem can be configured to collect loads acting upon a disposable wearable absorbent article, to anchor itself to a body of a wearer, and to balance the collected loads with holding forces obtained from the anchoring. Throughout the present disclosure, the term "anchored" refers to a configured relationship between part or all of an anchoring subsystem in a disposable wearable absorbent article and part or all of a body of a wearer, while the article is worn by the wearer. Where an element of an anchoring subsystem is anchored to a portion of a body of a wearer, at least part of the element is in direct and/or indirect contact with the portion of the body and the anchoring subsystem is configured to at least reduce and/or prevent relative movement between the element and the portion, while the article is worn by the wearer.

An anchoring subsystem can be anchored to a body of a wearer with one or more elements of the anchoring subsystem configured to contact various parts of a body of a wearer. For example, an anchoring subsystem can be at least partially anchored by wrapping one or more anchoring subsystem elements at least partway around a front, back, and/or side of a body of a wearer, thus creating friction and/or reaction forces. A part of the body with a relatively smaller radius of curvature can, in some embodiments, provide greater friction forces, since an element can tend to wrap around such parts more tightly. This is due to the physics of a flexible material that is wrapped around a curved surface and placed under tension. In this scenario, as a tensile force places the flexible material under tension, the flexible material exerts a normal force perpendicular to and inward on the curved surface. According to the basic Capstan formula, the normal force is proportional to the tensile force divided by the radius of the curved surface. Thus, at a given tensile force as the radius becomes smaller the normal force becomes larger. Also as an example, an anchoring subsystem can be at least partially anchored by setting one or more anchoring subsystem elements on, around, and/or above protruding portions of a body of a wearer, thus creating friction and/or reaction forces. A part of the body with a relatively larger horizontal protrusion can, in some embodiments, provide greater reaction forces, since an element can tend to hang and/or ride on such parts more securely.

In order to collect loads, anchor itself to a body of a wearer, and balance various forces, an anchoring subsystem can be configured to include a number of anchoring subsystem elements. In some embodiments, an anchoring subsystem element can be an elongated element configured to carry tension. Anchoring subsystem elements can follow various pathways on external surfaces of a body of a wearer of the disposable wearable absorbent article in which the anchoring subsystem is included. The shapes of these external surfaces can affect the shapes of the pathways. The shapes of the pathways can, in turn, affect configurations of anchoring subsystem elements. Many external surfaces on human bodies include curved shapes, such as a curve around a hip of a human body. Different human bodies can include different curves as bodies have various sizes and shapes. In some embodiments, part or all of an anchoring subsystem element that follows a curved pathway can be a geodesic.

The term geodesic relates to a theoretical element with mathematical properties described by curved geometries. In this theoretical context, a geodesic is a curved line on a curved surface, wherein the curved line appears to travel straight, without turning to the left or to the right, when viewed from that curved surface. In other words, a geodesic can be thought of as a line pulled taut on a frictionless curved surface. On a flat surface, the shortest distance between two points is a straight line. On a curved surface, the shortest distance between two points is a geodesic. More information on geodesics and their mathematical properties can be found in texts on differential geometry and the theory of general relativity, for example Barrett O'Neill, Elementary Differential Geometry Ch. 7 (Academic Press 2006); and James Foster & David J. Nightingale, A Short Course in General Relativity Ch. 2.1 (Springer Science and Business Media 2006).

Part or all of an anchoring subsystem element can be configured as a geodesic. While, throughout the present disclosure, anchoring subsystem elements are described as geodesics, these descriptions are intended to mean that such anchoring subsystem elements are configured as close approximations to theoretical geodesic elements. Real world elements cannot behave exactly like theoretical geodesic elements since real world elements always have at least some thickness, always experience at least some friction, and are always subject to at least some small non-axial outside forces, as will be understood by one of ordinary skill in the art.

Part or all of an anchoring subsystem element can be configured as a geodesic as the element follows various convex curved pathways on external surfaces of a body of a wearer. An anchoring subsystem element that is loaded in tension (e.g., axial loading) can be configured as a geodesic, since the tension can conform the element to the convex curved pathway. When a point load is added to an anchoring subsystem element that is a geodesic, at an angle other than in-line with the geodesic, that point load deforms the original geodesic, dividing the original geodesic into two new geodesics in the anchoring subsystem element. Similarly, when an anchoring subsystem element, configured in tension as a geodesic, passes over a concave portion of a generally convex external surface of a human body, the element bridges the concave portion, separating the anchoring subsystem element into two geodesics on either convex side of the concave portion. Further, the bridging portion of the anchoring subsystem element is also a geodesic, since it is a straight line in space. When an anchoring subsystem element that is a geodesic is subjected to a load distributed along at least a portion of the length of the element, at an angle other than in-line with the geodesic, the element no longer behaves as a geodesic, and instead begins to act in a manner referred to herein as "geometric anchoring." An anchoring subsystem can include a number of anchoring subsystem elements, at least some of which can be configured as geodesics.

One kind of anchoring subsystem element is a side anchoring member (SAM). A SAM is one or more physical, tension-carrying elements and/or areas disposed along a defined SAM pathway in an anchoring subsystem of a disposable wearable absorbent article. A SAM has two defined ends, a middle between the two ends, and a defined length from its one end to its other end. A SAM can have one or more widths, each of which is less than its defined length. A SAM pathway cannot substantially or completely encircle the lower torso of the body of the wearer. At least a portion of a SAM pathway passes through a side of the disposable wearable absorbent article. In some embodiments, a SAM can be contained within a side of the disposable wearable absorbent article.

A side of a disposable wearable absorbent article can be defined in various ways. A side of a disposable wearable absorbent article can include a portion of a front of the article as well as a portion of a back of the article. Sometimes, a side of a disposable wearable absorbent article can be considered disposed in a portion of the article that is laterally offset from a lateral centerline of the article. Throughout the present disclosure, unless otherwise stated, a side of a disposable wearable absorbent article is disposed in a portion of the article that is laterally outboard from longitudinal edges of an absorbent core of the article. In some instances, a side of a disposable wearable absorbent article can be considered disposed in a portion of the article that is laterally outboard from a narrowest portion of a chassis of the article. In various instances, a side of a disposable wearable absorbent article can be considered disposed in a side panel or a side ear of the article. Embodiments of the present disclosure can be used with any of these definitions of a side of a disposable wearable absorbent article.

In an anchoring subsystem of a disposable wearable absorbent article, one or more SAMs can be configured to contact various parts of a body of a wearer, to at least assist in anchoring the anchoring subsystem to the body. A SAM can receive at least some collected loads from one or more elements of the disposable wearable absorbent article, such as a chassis, a fastener, a leg cuff, etc. A SAM can also provide holding forces to help balance the collected loads through contact with the body. In balancing these loads and forces, the SAM carries tensions in the anchoring system. This balancing can enable the anchoring subsystem to at least assist in holding a disposable wearable absorbent article in place on a wearer.

A SAM can be configured in various forms. In some embodiments, a SAM can include a number of elements, such as fasteners. Part or all of a SAM can be straight, curved, angled, segmented, or other shapes, or combinations of any of these shapes. Part or all of a SAM can be structurally associated with one or more elements of the disposable wearable absorbent article. As examples, part or all of a SAM can be discrete from and/or joined to and/or attached to and/or embedded in and/or integral with one or more elements of the disposable wearable absorbent article. Throughout the present disclosure, the term "joined" refers to configurations whereby an element is directly connected to another element by affixing the element directly to the other element and to configurations whereby an element is indirectly secured to another element by affixing the element to intermediate member(s) which in turn are affixed to the other element.

A SAM can be made from any material suitable for carrying tensions in an anchoring system. Part or all of a SAM can include one or more of various elastic, inelastic, extensible, inextensible, stretchable, and/or non-stretchable material(s) and/or any other suitable material(s) and/or combinations of any of these materials. As examples, part or all of a SAM can include one or more of various elastomeric materials, such as extruded films, elastics, nonwovens, scrims, slot-coated films, sprayed or melt-blown fibers, and/or printed elastics and/or any other suitable elastomeric material(s) and/or combinations of any of these materials. Also as examples, part or all of a SAM can be structurally associated with part or all of one or more elements of a disposable wearable absorbent article, such as embodiments wherein one or more of the element(s) are configured with an elastic nonwoven, with an elastic film and extensible nonwoven, with an extensible film and an elastic nonwoven, to be pre-stretched with elastic strands allowed to contract, to be incrementally stretched, with zero strain laminate, and/or in combinations of these and/or other configurations. In some embodiments, a SAM can include one or more laminate materials. In various embodiments, a SAM can be formed from various basis weights, chemistries, and/or incremental stretchings, as will be understood by one of ordinary skill in the art. A SAM can be any suitable width or thickness. For example, a SAM can be from 5 mm to about 75 mm wide or any width within that range. The width and/or thickness of a SAM can, in some embodiments, vary over the length of the SAM.

As described above, an anchoring subsystem can balance loads and forces, thus performing functions similar to those of an anchoring system for a disposable wearable absorbent article, as described in U.S. application Ser. No. 11/599,851. As a result, an anchoring subsystem can provide benefits similar to those of an anchoring system for a disposable wearable absorbent article; helping prevent the article from sagging or slipping down on a wearer. However, an anchoring subsystem differs from an anchoring system in the extent of its presence within a disposable wearable absorbent article. In an anchoring subsystem of a disposable wearable absorbent article, no element of the anchoring subsystem substantially or completely encircles the lower torso of a wearer when the disposable wearable absorbent article is worn by the wearer. Further, an anchoring subsystem is contained within a particular, defined area of a disposable wearable absorbent article. For example, a side anchoring subsystem of a disposable wearable absorbent article is contained within a side of the disposable wearable absorbent article.

FIG. 1A illustrates a plan view of a pant-type disposable wearable absorbent article 110, including an anchoring subsystem 170 with crossing side anchoring members 150, 160, according to embodiments of the present disclosure.

In FIG. 1A, a lateral centerline 113 and a longitudinal centerline 117 provide lines of reference for referring to relative locations of parts of the disposable wearable absorbent article 110. When a first part is nearer to the lateral centerline 113 than a second part, the first part can be considered laterally inboard 112 to the second part. Similarly, the second part can be considered laterally outboard 114 from the first part. When a third part is nearer to the longitudinal centerline 117 than a fourth part, the third part can be considered longitudinally inboard 116 to the fourth part. Similarly, the fourth part can be considered longitudinally outboard 118 from the third part. FIG. 1A includes arrows indicating relative directions for laterally inboard, laterally outboard, longitudinally inboard, and longitudinally outboard, with respect to the disposable wearable absorbent article 110. Throughout the present disclosure, unless otherwise stated, a reference to a lateral dimension, measurement, line, or direction refers to a dimension, measurement, line, or direction substantially perpendicular to the lateral centerline 113, and a reference to a longitudinal dimension, measurement, line, or direction refers to a dimension, measurement, line, or direction substantially perpendicular to the longitudinal centerline 117.

The disposable wearable absorbent article 110 includes a front 123 and a back 127. The front 123 is a portion of the disposable wearable absorbent article 110 disposed generally proximate to and/or below the belly of a wearer, when the disposable wearable absorbent article 110 is worn by the wearer. A general reference to the "front" can mean the front 123, part or all of an element in the front 123, and/or a disposition in the front 123, depending on the context of the reference. The back 127 is a portion of the disposable wearable absorbent article 110 disposed generally proximate to and/or below the back of a wearer, when the disposable wearable absorbent article 110 is worn by the wearer. A general reference to the "back" can mean the back 127, part or all of an element in the back 127, and/or a disposition in the back 127, depending on the context of the reference. The longitudinal centerline of the disposable wearable absorbent article 110 forms a boundary between the front 123 and the back 127. The front and back terminology described above is used for disposable wearable absorbent articles throughout the present disclosure unless otherwise indicated. In some embodiments, the front 123 and the back 127 can be considered first and second halves of the disposable wearable absorbent article 110, although the halves may not be equal.

The disposable wearable absorbent article 110 also includes a chassis 120, a front waistband 121, a narrowest portion 122 of the chassis 120, an absorbent core 125 with longitudinal edges 124, an absorbent core area 126, a front waist edge 128-F, a back waist edge 128-B, and a back waistband 129. A portion of the chassis 120 is illustrated as cut away in order to show the absorbent core 125 and the longitudinal edges 124 more clearly. A front portion of a first side 131 is disposed in the front 123. A back portion of the first side 139 is disposed in the back 127. The disposable wearable absorbent article 110 has a first side panel, which includes a front portion of the first side panel 133 and a back portion of the first side panel 137, configured to connect via a first side interface 135. Throughout the present disclosure, for clarity, side panels are illustrated as distinct elements within disposable wearable absorbent articles. However, in various embodiments, one or more portions or all of a side panel may not be distinct elements within a disposable wearable absorbent article.

Figure 1B:
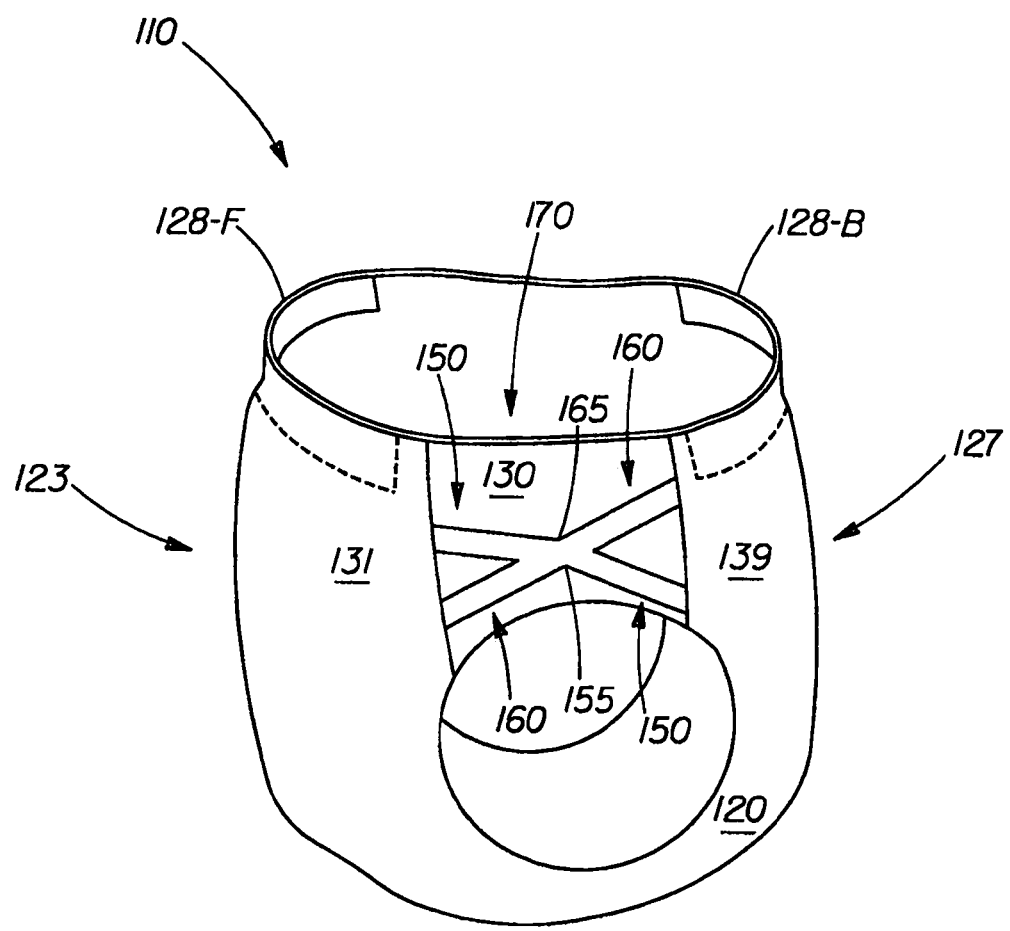
FIG. 1B illustrates a perspective view of an outside of the disposable wearable absorbent article of the embodiment of FIG. 1A, formed for wearing.
Figure 1C:
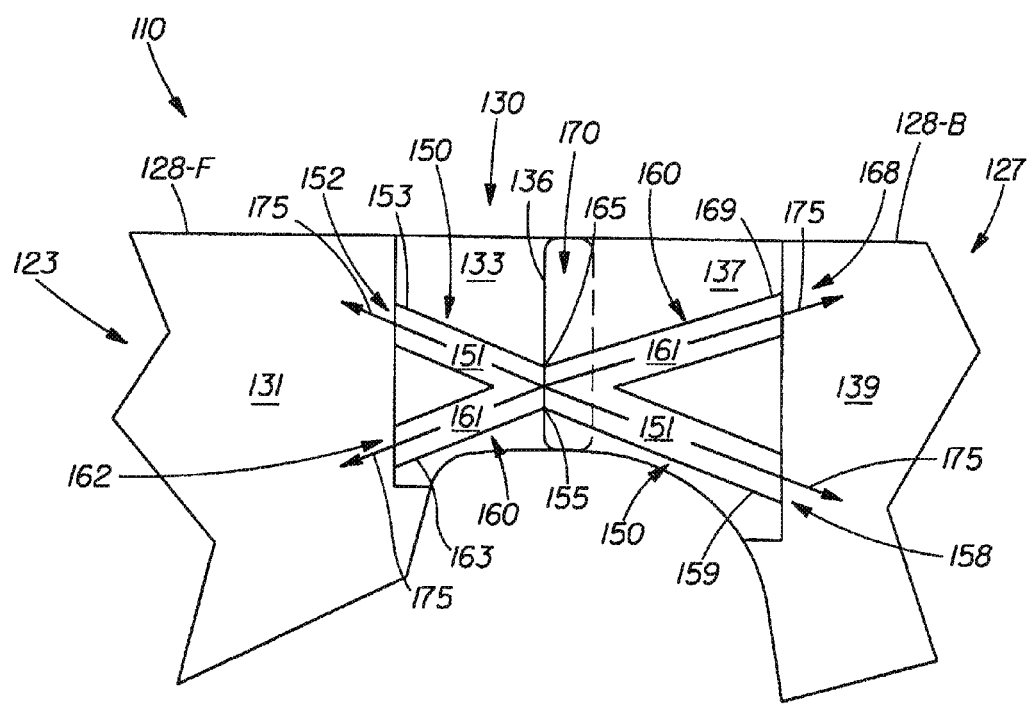
FIG. 1C illustrates an enlarged view of a portion of a side of the disposable wearable absorbent article of the embodiment of FIG. 1B.

The first side panel also includes the anchoring subsystem 170. The anchoring subsystem 170 includes a first SAM 150 and a second SAM 160. The first SAM 150 is disposed along a first SAM pathway 151, and includes a first end 153 disposed at a first location 152, a second end 159 disposed at a second location 158, and a first middle 155 between the first end 153 and the second end 159. The second SAM 160 is disposed along a second SAM pathway 161, and includes a third end 163 disposed at a third location 162, a fourth end 169 disposed at a fourth location 168, and a second middle 165 between the third end 163 and the fourth end 169. Portions of the first SAM pathway 151 are distinct from the second SAM pathway 161. However, the first SAM pathway 151 and the second SAM pathway 161 cross, so a portion of the first middle 155 is coextensive with a portion of the second middle 165. In the embodiment of FIGS. 1A-1C, the coextensive portion bridges the first side interface 135, however, in some embodiments, the SAM pathways can cross in the front portion of the first side panel 133 or in the back portion of the first side panel 137. In various embodiments, part or all of the first SAM pathway 151 and/or the second SAM pathway 161 can be configured as a geodesic, so that the anchoring subsystem 170 can provide geodesic anchoring.

For clarity, in the embodiments of FIGS. 1A-9C, SAMs are illustrated as visibly apparent elements within side panels and side ears. However, in various embodiments, part or all of an anchoring subsystem element may not be readily visibly apparent within a disposable wearable absorbent article. For example, a SAM may not be readily visibly apparent in embodiments wherein the SAM is embedded in or integral with a side panel or a side ear.

Also for clarity, in the embodiments of FIGS. 1A-9C, SAM pathways are illustrated as unitary, continuous pathways. However, in some embodiments, part or all of a SAM can be formed by a number of discrete elements and/or separate areas disposed along a SAM pathway. As examples, a SAM can be formed by substantially parallel strands of material running through a side panel or a side ear, or by a series of pieces of material attached to a side panel or a side ear, or by a distribution of unstretched areas in an incrementally stretched side panel or side ear.

The second end 159 and the fourth end 169 are both disposed outside of the absorbent core area 126, in the back portion of the first side 139, laterally outboard from the longitudinal edge 124 of the absorbent core 125, laterally inboard to the narrowest portion 122 of the chassis 120, and within the back portion of the first side panel 137 proximate to a laterally inboard edge of the back portion of the first side panel 137. In some embodiments, one or both of the second and fourth ends 159, 169 can be disposed at various locations, including locations outside of the back portion of the first side panel 137, and/or within the back portion of the first side 139, and/or laterally outboard from the narrowest portion 122 of the chassis 120, and/or laterally inboard to the longitudinal edges 124 of the absorbent core 125, and/or within the absorbent core area 126. The fourth location 168 is longitudinally outboard from the second location 158.

The first end 153 and the third end 163 are both disposed outside of the absorbent core area 126, in the front portion of the first side 131, laterally outboard from the longitudinal edge 124 of the absorbent core 125, laterally inboard to the narrowest portion 122 of the chassis 120, and within the front portion of the first side panel 133 proximate to a laterally inboard edge of the front portion of the first side panel 133. In some embodiments, one or both of the first and third ends 153, 163 can be disposed at various locations, including locations outside of the front portion of the first side panel 133, and/or within the front portion of the first side 131, and/or laterally outboard from the narrowest portion 122 of the chassis 120, and/or laterally inboard to the longitudinal edges 124 of the absorbent core 125, and/or within the absorbent core area 126. The third location 162 is longitudinally inboard to the first location 152.

The anchoring subsystem 170 is not directly connected to the absorbent core 125, and is outside of the absorbent core area 126, so the anchoring subsystem 170 is separate from the absorbent core 125. However, in various embodiments, part or all of one or more elements of an anchoring subsystem can be inside of an absorbent core area, and/or joined or directly connected to an absorbent core. The anchoring subsystem 170 is considered a subsystem because neither the first SAM 150 nor the second SAM 160 will substantially or completely encircle the lower torso of a wearer, and because the anchoring subsystem 170 is contained within a particular, defined portion of the disposable wearable absorbent article 110. In the embodiment of FIGS. 1A-1C, the anchoring subsystem 170 is contained within the first side of the disposable wearable absorbent article 110, so the anchoring subsystem 170 is considered a side anchoring subsystem. The disposable wearable absorbent article 110 can also include an outer cover, which can, in various embodiments, be separate from the anchoring subsystem 170. In some embodiments, part or all of such an outer cover can be stretchable, elastic, or extensible.

The disposable wearable absorbent article 110 also includes a second side with a front portion of the second side 141 disposed in the front 123 and a back portion of the second side 149 disposed in the back 127. The disposable wearable absorbent article 110 has a second side panel, which includes a front portion of the second side panel 143 and a back portion of the second side panel 147, configured to connect via a second side interface 145. The second side panel is configured similar to the first side panel, however, in various embodiments, the second side panel can, alternatively, be configured differently.

FIG. 1B illustrates a perspective view of an outside of the disposable wearable absorbent article 110 of the embodiment of FIG. 1A, formed for wearing. In the embodiment of FIG. 1B, the first side is connected via the first side interface 135.

FIG. 1C illustrates an enlarged view of a portion of a side of the disposable wearable absorbent article 110 of the embodiment of FIG. 1B. A connection 136 proximate to the first side interface 135 connects the front portion of the first side panel 133 with the back portion of the first side panel 137 to form the first side. The connection 136 can take various forms, such as a fastenable connection or a durable connection. The location of the connection 136 can vary in some embodiments. In some embodiments, a side can, alternatively, be formed with more than one connection at various locations or without a distinct connection within the side.

In various embodiments of the present disclosure, one or more parts of or at least a portion of the anchoring subsystem 170 can be structurally associated with the first side panel. In some embodiments, at least a portion of the anchoring subsystem 170, or substantially all of the anchoring subsystem 170, or even all of the anchoring subsystem 170, can be discrete from, or joined to, attached to, or embedded in, or integral with the first side panel. In various embodiments, at least a portion of the first SAM 150 and/or the second SAM 160, or substantially all of the first SAM 150 and/or the second SAM 160, or even all of the first SAM 150 and/or the second SAM 160, can be discrete from, or joined to, or attached to, or embedded in, or integral with the first side panel.

In embodiments in which one or more portions of the anchoring subsystem 170 are integral with the first side panel, the first side panel can be considered to have a first portion, which includes the integral portions of the anchoring subsystem 170, and a second portion outside of the first portion. For example, if all of the first SAM 150 and all of the second SAM 160 were integral with the first side panel, then the first portion would include the first SAM pathway 151 and the second SAM pathway 161, while the second portion would include the four roughly triangular sections of the first side panel that are outside of the first SAM pathway 151 and the second SAM pathway 161. In such embodiments, this first portion and second portion can be configured in various ways, as described in the following examples.

The disposable wearable absorbent article 110 can be configured such that substantially all of the first portion can be incrementally stretched to one or more lesser degrees and substantially all of the second portion can be incrementally stretched to one or more greater degrees.

Figure 10A:
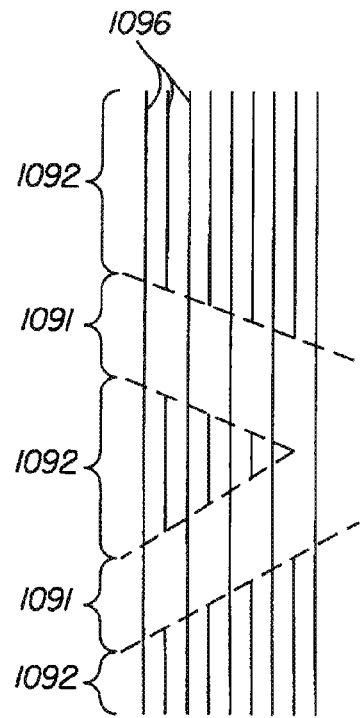
FIG. 10A illustrates a first embodiment of incremental stretching for use in an anchoring subsystem in a side of the disposable wearable absorbent article, according to embodiments of the present disclosure.
Figure 10B:
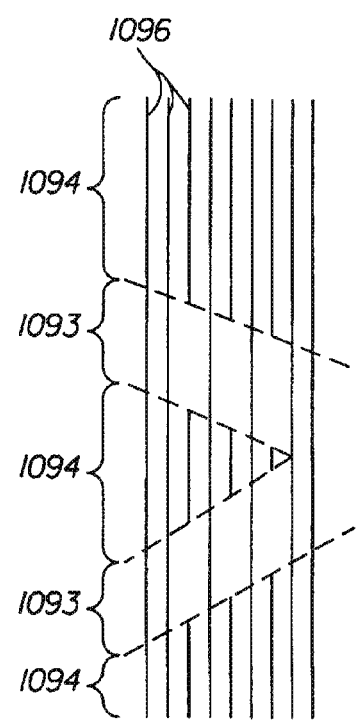
FIG. 10B illustrates a second embodiment of incremental stretching for use in an anchoring subsystem in a side of the disposable wearable absorbent article, according to embodiments of the present disclosure.
Figure 10C:
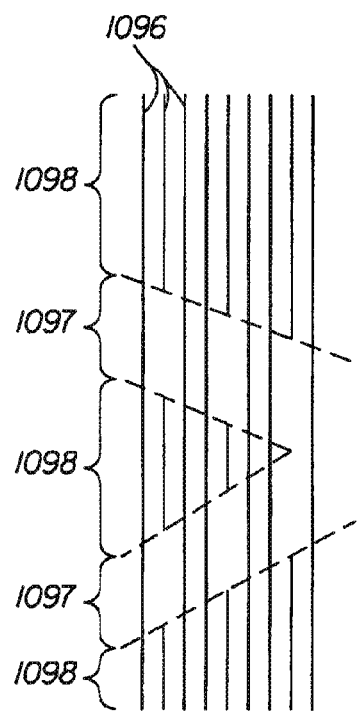
FIG. 10C illustrates a third embodiment of incremental stretching for use in an anchoring subsystem in a side of the disposable wearable absorbent article, according to embodiments of the present disclosure.

The disposable wearable absorbent article 110 can be configured such that the first portion can be incrementally stretched with a first particular number of teeth per a unit of distance, and the second portion can be incrementally stretched with a second particular number of teeth per the unit of distance, wherein the first particular number of teeth can be less than or equal to the second particular number of teeth. As examples, the first particular number of teeth can be at or about nine tenths, or four fifths, or three quarters, or two thirds, or one half, or one third, or one quarter, or one fifth, or one tenth of the second particular number of teeth. The embodiments of FIGS. 10A-10C illustrate incremental stretching.

The disposable wearable absorbent article 110 can be configured such that substantially all of the first portion can be configured to have a higher directional modulus of elasticity, and substantially all of the second portion can be configured to have one or more lower directional modulii of elasticity, based on the directionality described in the modulus mapping method described herein. In various embodiments, the higher directional modulus of elasticity can be at least 10, or at least 50, or at least 100, or at least 250, or at least 400 percent greater than the one or more lower directional modulii of elasticity.

The disposable wearable absorbent article 110 can be configured such that substantially all of the first portion includes one or more higher caliper elastomers, and substantially all of the second portion includes one or more lower caliper elastomers. The disposable wearable absorbent article 110 can be configured such that substantially all of the first portion includes one or more higher performance elastomers, and substantially all of the second portion includes one or more lower performance elastomers.

The disposable wearable absorbent article 110 can be configured such that one or more unstretched portions can be distributed throughout substantially all of the first portion, and substantially all of the second portion can be incrementally stretched.

The disposable wearable absorbent article 110 can be configured such that one or more over-bonded portions can be distributed throughout substantially all of the first portion.

The disposable wearable absorbent article 110 can be configured such that substantially all of the first portion can be configured to have one or more higher forces per unit width at a particular strain, and substantially all of the second portion can be configured to have one or more lower forces per unit width at the particular strain. In various embodiments, the ratio of one of the higher force per unit width to one of the lower force per unit width can be at least 1.1, or at least 1.5, or at least 2, or at least 3.5, or at least 5.

In some embodiments, the disposable wearable absorbent article 110 can be configured such that one or more loads in the article can cause tension in the anchoring subsystem 170 before the load can cause tension in a portion of the first side panel that is outside of the anchoring subsystem 170. In various embodiments, the disposable wearable absorbent article 110 can be configured such that one or more loads in the article can cause greater tension in the anchoring subsystem 170 than in a portion of the first side panel that is outside of the anchoring subsystem 170.

In addition to the elements previously described, the embodiment of FIG. 1C includes tension lines 175. The tension lines 175 illustrate how the first SAM 150 and the second SAM 160 can balance collected loads with obtained holding forces, so that the anchoring subsystem 170 can at least assist in holding the disposable wearable absorbent article 110 in place on a wearer. For example, the first SAM 150 can collect loads at the second end 159 and/or along the first SAM pathway 151. Also as an example, the second SAM 160 can collect loads at the third end 163 and/or along the second SAM pathway 161. In a further example, the first SAM 150 can obtain holding forces at the first end 153 and/or along the first SAM pathway 151 as the first SAM 150 experiences anchoring from direct or indirect contact with a wearer's body underneath the first SAM pathway 151. In still a further example, the second SAM 160 can obtain holding forces at the fourth end 169 and/or along the second SAM pathway 161 as the second SAM 150 experiences anchoring. These loads and forces can be received through various parts of the disposable wearable absorbent article 110, such as the chassis 120 and/or the first side panel.

The anchoring subsystem 170 is configured to indirectly anchor the absorbent core 125 to a wearer, in that, while the first SAM 150 and the second SAM 160 are not directly connected to the absorbent core 125, and the first SAM pathway 151 and the second SAM pathway 161 are each disposed outside of the absorbent core area 126, loads from the absorbent core 125 can be transmitted through various parts of the disposable wearable absorbent article 110 to the first SAM 150 and/or the second SAM 160, which can balance collected loads with obtained holding forces, so that the anchoring subsystem 170 can at least assist in holding the disposable wearable absorbent article 110 in place on a wearer. As a result, the disposable wearable absorbent article 110 can feel comfortable, look attractive, and perform well as the article tends to stay in place on a wearer and not leak.

Figure 2A:
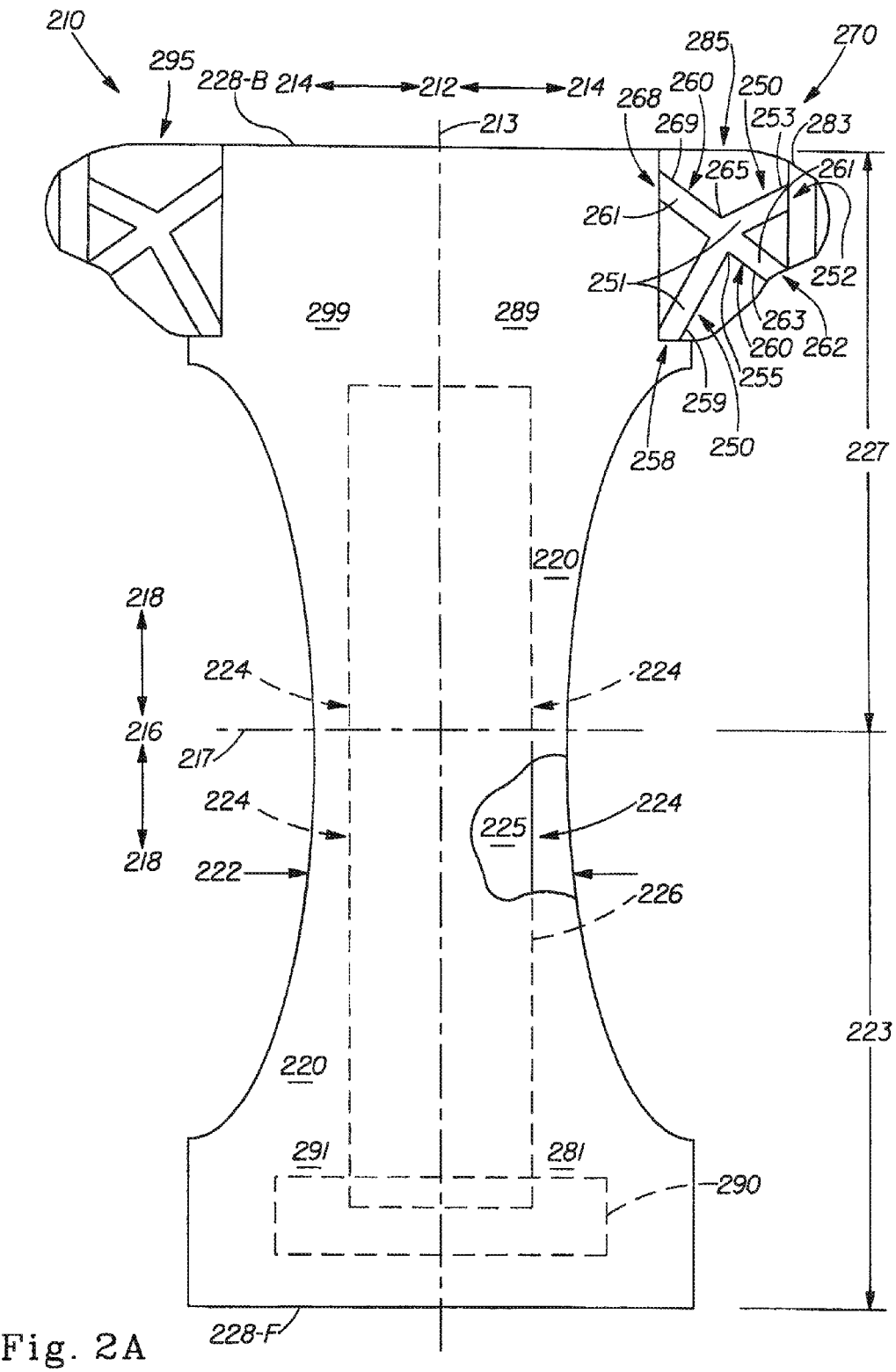
FIG. 2A illustrates a plan view of an inside of a fastenable disposable wearable absorbent article, including an anchoring subsystem with crossing side anchoring members, and side ears, each with one fastener, according to embodiments of the present disclosure.

FIG. 2A illustrates a plan view of an inside of a fastenable disposable wearable absorbent article 210, including an anchoring subsystem 270 with crossing side anchoring members 250, 260, and side ears 285, 295, each with one fastener, according to embodiments of the present disclosure. The disposable wearable absorbent article 210 includes a longitudinal centerline 217 and a lateral centerline 213, which provide lines of reference for referring to laterally inboard 212, laterally outboard 214, longitudinally inboard 216, and longitudinally outboard 218 relative locations of the disposable wearable absorbent article 210.

The disposable wearable absorbent article 210 also includes a chassis 220, a narrowest portion 222 of the chassis 220, a front 223, an absorbent core 225 with longitudinal edges 224, an absorbent core area 226, a back 227, a front waist edge 228-F, and a back waist edge 228-B. A portion of the chassis 220 is illustrated as cut away in order to show the absorbent core 225 and the longitudinal edges 224 more clearly. In some embodiments, the front 223 and the back 227 can be considered first and second halves of the disposable wearable absorbent article 210, although the halves may not be equal. A front portion of a first side 281 is disposed in the front 223. A back portion of the first side 289 is disposed in the back 227.

The disposable wearable absorbent article 210 has a first side ear 285 connected to the back portion of the first side 289. Throughout the present disclosure, for clarity, side ears are illustrated as distinct elements within disposable wearable absorbent articles. However, in various embodiments, one or more portions or all of a side ear may not be distinct elements within a disposable wearable absorbent article.

The first side ear 285 includes a fastener 283 and the anchoring subsystem 270. The anchoring subsystem 270 includes a first SAM 250 and a second SAM 260. The first SAM 250 is disposed along a first SAM pathway 251, and includes a first end 253 disposed at a first location 252, a second end 259 disposed at a second location 258, and a first middle 255 between the first end 253 and the second end 259. The second SAM 260 is disposed along a second SAM pathway 261, and includes a third end 263 disposed at a third location 262, a fourth end 269 disposed at a fourth location 268, and a second middle 265 between the third end 263 and the fourth end 269. Portions of the first SAM pathway 251 are distinct from the second SAM pathway 261. However, the first SAM pathway 251 and the second SAM pathway 261 cross, so a portion of the first middle 255 is coextensive with a portion of the second middle 265. In various embodiments, part or all of the first SAM pathway 251 and/or the second SAM pathway 261 can be configured as a geodesic, so that the anchoring subsystem 270 can provide geodesic anchoring.

The second end 259 and the fourth end 269 are both disposed outside of the absorbent core area 226, in the back portion of the first side 289, laterally outboard from the longitudinal edge 224 of the absorbent core 225, laterally outboard from the narrowest portion 222 of the chassis 220, and within the first side ear 285 proximate to a laterally inboard edge of the first side ear 285. In some embodiments, one or both of the second and fourth ends 259, 269 can be disposed at various locations, including locations outside of the first side ear 285, and/or within the back portion of the first side 289, and/or laterally inboard to the narrowest portion 222 of the chassis 220, and/or laterally inboard to the longitudinal edges 224 of the absorbent core 225, and/or within the absorbent core area 226. The fourth location 268 is longitudinally outboard from the second location 258. The first end 253 and the third end 263 are both disposed within the first side ear 285. The dispositions of the first and third ends 253, 263 are further described in connection with the embodiment of FIG. 2C.

Figure 2B:
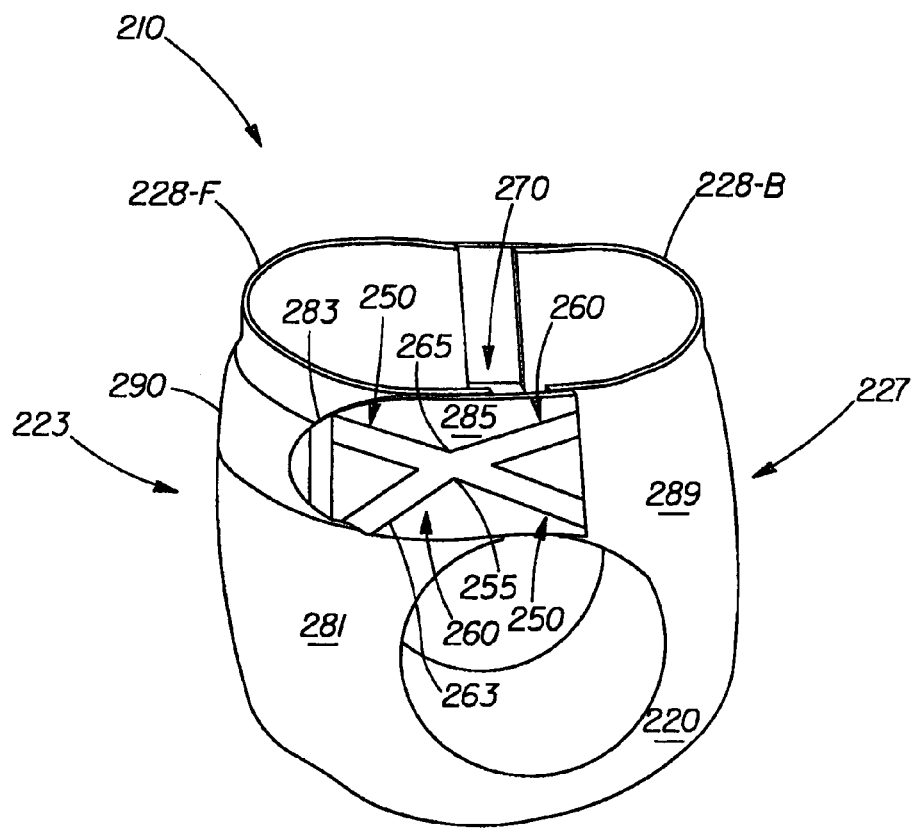
FIG. 2B illustrates a perspective view of an outside of the disposable wearable absorbent article of the embodiment of FIG. 2A, formed for wearing.
Figure 2C:
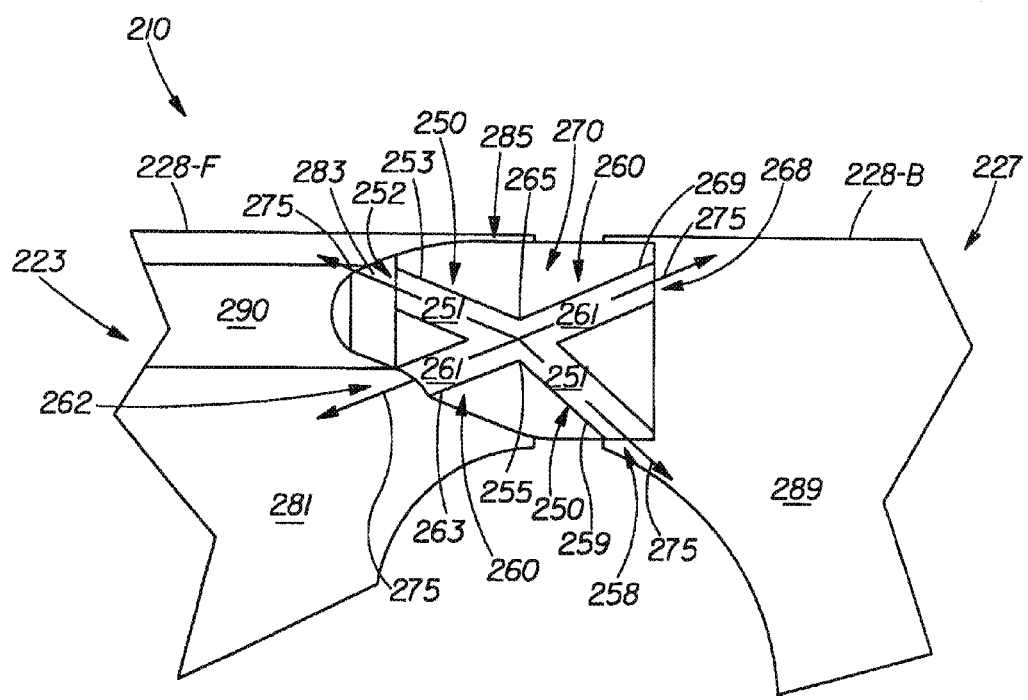
FIG. 2C illustrates an enlarged view of a portion of a side of the disposable wearable absorbent article of the embodiment of FIG. 2B.

The anchoring subsystem 270 is not directly connected to the absorbent core 225, and is outside of the absorbent core area 226, so the anchoring subsystem 270 is separate from the absorbent core 225. The anchoring subsystem 270 is considered a subsystem because neither the first SAM 250 nor the second SAM 260 will substantially or completely encircle the lower torso of a wearer, and because the anchoring subsystem 270 is contained within a particular, defined portion of the disposable wearable absorbent article 210. In the embodiment of FIGS. 2A-2C, the anchoring subsystem 270 is contained within the first side of the disposable wearable absorbent article 270, so the anchoring subsystem 270 is considered a side anchoring subsystem. The disposable wearable absorbent article 210 can also include an outer cover, which can, in various embodiments, be separate from the anchoring subsystem 270. In some embodiments, part or all of such an outer cover can be stretchable, elastic, or extensible.

The disposable wearable absorbent article 210 also includes a front portion of a second side 291, and a second side ear 295 connected to a back portion of the second side 299. The second side ear 295 is configured similar to the first side ear 285, however, in various embodiments, the second side ear 295 can, alternatively, be configured differently. The disposable wearable absorbent article 210 further includes a fastening area 290.

FIG. 2B illustrates a perspective view of an outside of the disposable wearable absorbent article 210 of the embodiment of FIG. 2A, formed for wearing. In the embodiment of FIG. 2B, the fastener 283 is fastened to the fastening area 290.

FIG. 2C illustrates an enlarged view of a portion of a side of the disposable wearable absorbent article 210 of the embodiment of FIG. 2B. The fastener 283 is fastened to the fastening area 290, so that the first side ear 285 fastens the front 223 to the back 227. As a result, a portion of the first side ear 285 is disposed in the front 223 and a portion of the first side ear 285 is disposed in the back 227. In this fastened configuration, the first end 253 and the third end 263 are both disposed outside of the absorbent core area 226, in the front portion of the first side 281, laterally outboard from the longitudinal edge 224 of the absorbent core 225, laterally outboard from the narrowest portion 222 of the chassis 220, and within the first side ear 285. The first end 253 is disposed proximate to an edge of the fastener 283 and the third end 263 is disposed proximate to a longitudinally inboard edge of the first side ear 285. In various embodiments, the third end 263 can also be disposed proximate to an edge of the fastener 283. In some embodiments, the fastener 283 can be fastened so that one or both of the first and third ends 253, 263 can be disposed at various locations, including locations laterally inboard to the narrowest portion 222 of the chassis 220, and/or laterally inboard to the longitudinal edges 224 of the absorbent core 225, and/or within the front portion of the first side 281, and/or within the absorbent core area 226. The third location 262 is longitudinally inboard to the first location 252.

In various embodiments of the present disclosure, one or more parts of or at least a portion of the anchoring subsystem 270 can be structurally associated with the first side ear 285. In some embodiments, at least a portion of the anchoring subsystem 270, or substantially all of the anchoring subsystem 270, or even all of the anchoring subsystem 270, can be discrete from, or joined to, attached to, or embedded in, or integral with the first side ear 285. In various embodiments, at least a portion of the first SAM 250 and/or the second SAM 260, or substantially all of the first SAM 250 and/or the second SAM 260, or even all of the first SAM 250 and/or the second SAM 260, can be discrete from, or joined to, or attached to, or embedded in, or integral with the first side ear 285.

In embodiments in which one or more portions of the anchoring subsystem 270 are integral with the first side ear 285, the first side ear 285 can be considered to have a first portion, which includes the integral portions of the anchoring subsystem 270, and a second portion outside of the first portion. For example, if all of the first SAM 250 and all of the second SAM 260 were integral with the first side ear 285, then the first portion would include the first SAM pathway 251 and the second SAM pathway 261, while the second portion would include the four roughly triangular sections of the first side ear 285 that are outside of the first SAM pathway 251 and the second SAM pathway 261. In such embodiments, this first portion and second portion can be configured in various ways, as described in the connection with the embodiment of FIG. 1C.

In some embodiments, the disposable wearable absorbent article 210 can be configured such that one or more loads in the article can cause tension in the anchoring subsystem 270 before the load can cause tension in a portion of the first side ear 285 that is outside of the anchoring subsystem 270. In various embodiments, the disposable wearable absorbent article 210 can be configured such that one or more loads in the article can cause greater tension in the anchoring subsystem 270 than in a portion of the first side ear 285 that is outside of the anchoring subsystem 270.

In addition to the elements previously described, the embodiment of FIG. 2C includes tension lines 275. The tension lines 275 illustrate how the first SAM 250 and the second SAM 260 can balance collected loads with obtained holding forces, so that the anchoring subsystem 270 can at least assist in holding the disposable wearable absorbent article 210 in place on a wearer. For example, the first SAM 250 can collect loads at the second end 259 and/or along the first SAM pathway 251, with loads received through various parts of the disposable wearable absorbent article 210, such as the chassis 220 and/or the first side ear 285. Also as an example, the second SAM 260 can collect loads at the third end 263 and/or along the second SAM pathway 261, with loads received through various parts of the disposable wearable absorbent article 210, such as the fastener 283 and/or the first side ear 285.

In a further example, the first SAM 250 can obtain holding forces at the first end 253 with forces received through various parts of the disposable wearable absorbent article 210, such as the fastener 283 and/or the first side ear 285. In a still further example, the first SAM 250 can also obtain holding forces along the first SAM pathway 251 as the first SAM 250 experiences anchoring from direct or indirect contact with a wearer's body underneath the first SAM pathway 251. As a similar example, the second SAM 260 can obtain holding forces at the fourth end 269 with forces received through various parts of the disposable wearable absorbent article 210, such as the chassis 220 and/or the first side ear 285. As another similar example, the second SAM 260 can obtain holding forces along the second SAM pathway 261 as the second SAM 250 experiences anchoring.

The anchoring subsystem 270 is configured to indirectly anchor the absorbent core 225 to a wearer, in that, while the first SAM 250 and the second SAM 260 are not directly connected to the absorbent core 225, and the first SAM pathway 251 and the second SAM pathway 261 are each disposed outside of the absorbent core area 226, loads from the absorbent core 225 can be transmitted through various parts of the disposable wearable absorbent article 210 to the first SAM 250 and/or the second SAM 260, which can balance collected loads with obtained holding forces, so that the anchoring subsystem 270 can at least assist in holding the disposable wearable absorbent article 210 in place on a wearer. As a result, the disposable wearable absorbent article 210 can feel comfortable, look attractive, and perform well as the article tends to stay in place on a wearer and not leak.

Figure 2D:
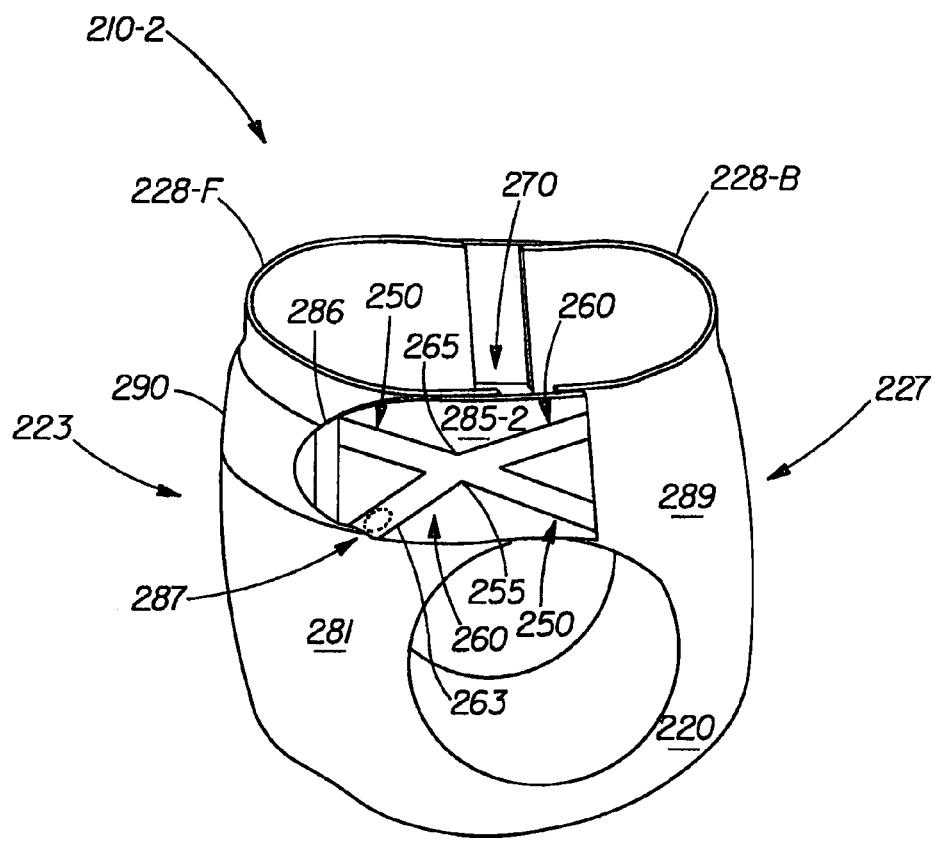
FIG. 2D illustrates a perspective view of an outside of a fastenable disposable wearable absorbent article, including an anchoring subsystem with crossing side anchoring members, and side ears, each with a first fastener and a second passive fastener, according to embodiments of the present disclosure.

FIG. 2D illustrates a perspective view of an outside of a fastenable disposable wearable absorbent article 210-2, including an anchoring subsystem 270 with partially coextensive side anchoring members, 250, 260, and side ears, each with a first fastener 286 and a second passive fastener 287, according to embodiments of the present disclosure. The disposable wearable absorbent article 210-2 is configured as the disposable wearable absorbent article 210 of the embodiments of FIGS. 2A-2C, except as described otherwise herein. The disposable wearable absorbent article 210-2 includes a chassis 220, a front 223, and a back 227. The first SAM 250 includes a first middle 255 and the second SAM 260 includes a third end 263 and a second middle 265. The disposable wearable absorbent article 210-2 also includes a first side, with a front portion of the first side 281 and a back portion of the first side 289, as well as a first side ear 285-2. The first side ear 285-2 includes the active fastener 286 and the passive fastener 287. The passive fastener 287 is disposed proximate to the third end 263 of the second SAM 260. The second SAM 260 can collect loads at the third end 263 through various parts of the disposable wearable absorbent article 210, such as through the passive fastener 287. The second side ear (not shown) can be configured similar to the first side ear 285-2 or can be configured differently.

Figure 3A:
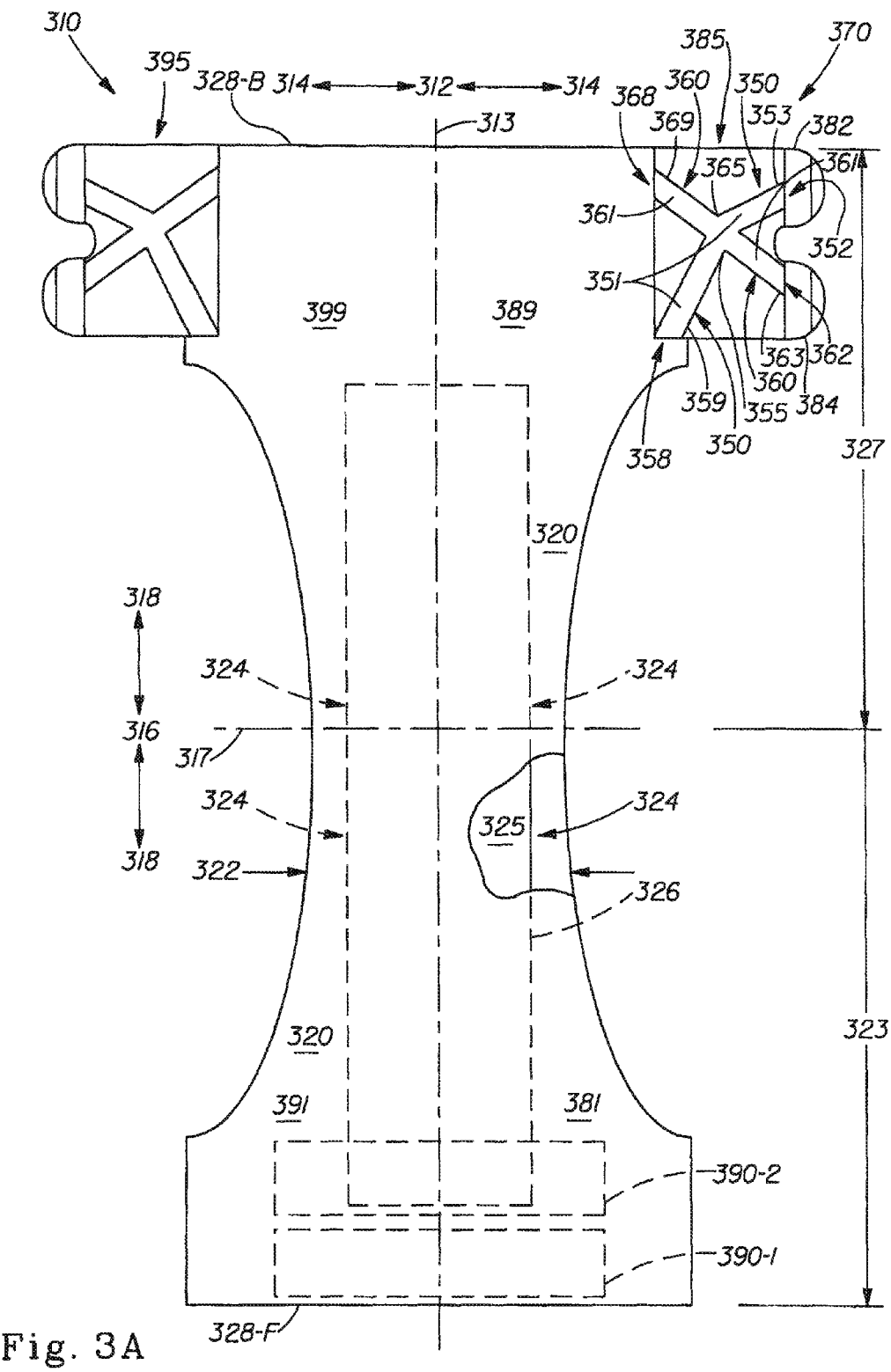
FIG. 3A illustrates a plan view of an inside of a fastenable disposable wearable absorbent article, including an anchoring subsystem with crossing side anchoring members, and side ears, each with two fasteners, according to embodiments of the present disclosure.

FIG. 3A illustrates a plan view of an inside of a fastenable disposable wearable absorbent article 310, including an anchoring subsystem 370 with crossing side anchoring members, 350, 360, and side ears, 385, 395, each with two fasteners, according to embodiments of the present disclosure. The disposable wearable absorbent article 310 includes a lateral centerline 317 and a longitudinal centerline 313, which provide lines of reference for referring to laterally inboard 312, laterally outboard 314, longitudinally inboard 316, and longitudinally outboard 318 relative locations of the disposable wearable absorbent article 310.

The disposable wearable absorbent article 310 also includes a chassis 320, a narrowest portion 322 of the chassis 320, a front 323, an absorbent core 325 with longitudinal edges 324, an absorbent core area 326, a back 327, a front waist edge 328-F, and a back waist edge 328-B. A portion of the chassis 320 is illustrated as cut away in order to show the absorbent core 325 and the longitudinal edges 324 more clearly. In some embodiments, the front 323 and the back 327 can be considered first and second halves of the disposable wearable absorbent article 310, although the halves may not be equal. A front portion of a first side 381 is disposed in the front 323. A back portion of the first side 389 is disposed in the back 327.

The disposable wearable absorbent article 310 has a first side ear 385 connected to the back portion of the first side 389. The first side ear 385 includes a first fastener 382, a second fastener 384, and the anchoring subsystem 370. The anchoring subsystem 370 includes a first SAM 350 and a second SAM 360. The first SAM 350 is disposed along a first SAM pathway 351, and includes a first end 353 disposed at a first location 352, a second end 359 disposed at a second location 358, and a first middle 355 between the first end 353 and the second end 359. The second SAM 360 is disposed along a second SAM pathway 361, and includes a third end 363 disposed at a third location 362, a fourth end 369 disposed at a fourth location 368, and a second middle 365 between the third end 363 and the fourth end 369. Portions of the first SAM pathway 351 are distinct from the second SAM pathway 361. However, the first SAM pathway 351 and the second SAM pathway 361 cross, so a portion of the first middle 355 is coextensive with a portion of the second middle 365. In various embodiments, part or all of the first SAM pathway 351 and/or the second SAM pathway 361 can be configured as a geodesic, so that the anchoring subsystem 370 can provide geodesic anchoring.

The second end 359 and the fourth end 369 are both disposed outside of the absorbent core area 326, in the back portion of the first side 389, laterally outboard from the longitudinal edge 324 of the absorbent core 325, laterally outboard from the narrowest portion 322 of the chassis 320, and within the first side ear 385 proximate to a laterally inboard edge of the first side ear 385. In some embodiments, one or both of the second and fourth ends 359, 369 can be disposed at various locations, including locations outside of the first side ear 385, and/or within the back portion of the first side 389, and/or laterally inboard to the narrowest portion 322 of the chassis 320, and/or laterally inboard to the longitudinal edges 324 of the absorbent core 325, and/or within the absorbent core area 326. The fourth location 368 is longitudinally outboard from the second location 358. The first end 353 and the third end 363 are both disposed within the first side ear 385. The dispositions of the first and third ends 353, 363 are further described in connection with the embodiment of FIG. 3C.

Figure 3B:
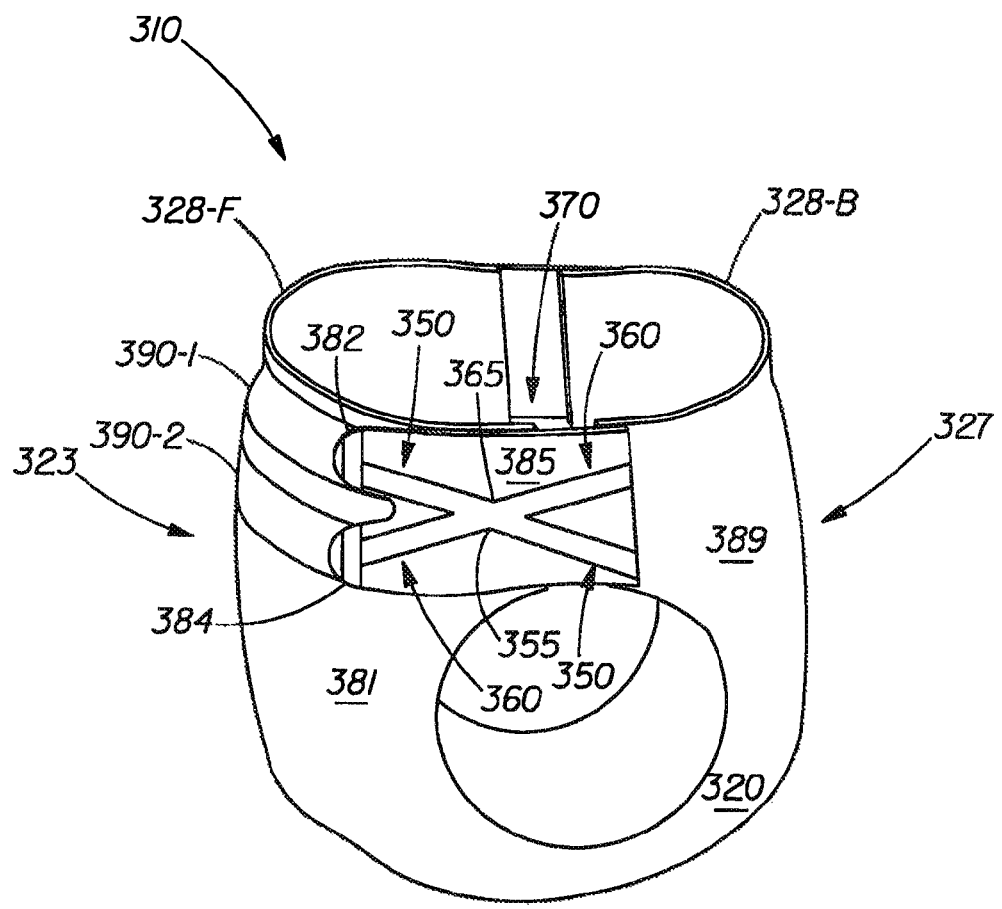
FIG. 3B illustrates a perspective view of an outside of the disposable wearable absorbent article of the embodiment of FIG. 3A, formed for wearing.
Figure 3C:
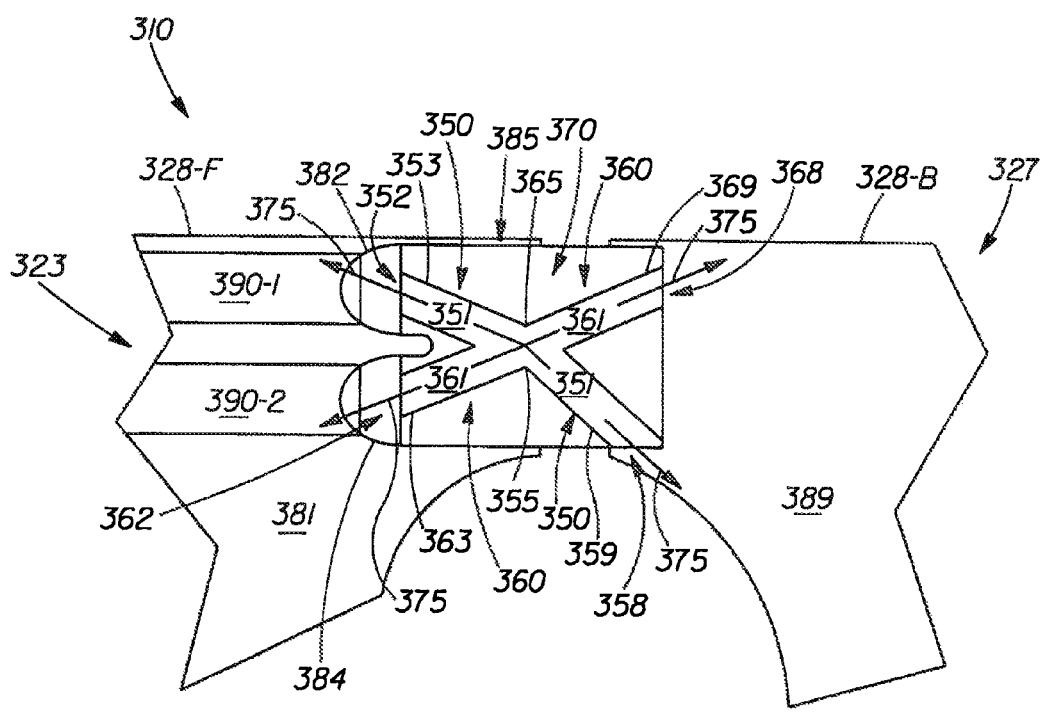
FIG. 3C illustrates an enlarged view of a portion of a side of the disposable wearable absorbent article of the embodiment of FIG. 3B.

The anchoring subsystem 370 is not directly connected to the absorbent core 325, and is outside of the absorbent core area 326, so the anchoring subsystem 370 is separate from the absorbent core 325. The anchoring subsystem 370 is considered a subsystem because neither the first SAM 350 nor the second SAM 360 will substantially or completely encircle the lower torso of a wearer, and because the anchoring subsystem 370 is contained within a particular, defined portion of the disposable wearable absorbent article 310. In the embodiment of FIGS. 3A-3C, the anchoring subsystem 370 is contained within the first side of the disposable wearable absorbent article 370, so the anchoring subsystem 370 is considered a side anchoring subsystem. The disposable wearable absorbent article 310 can also include an outer cover, which can, in various embodiments, be separate from the anchoring subsystem 370. In some embodiments, part or all of such an outer cover can be stretchable, elastic, or extensible.

The disposable wearable absorbent article 310 also includes a front portion of a second side 391, a second side ear 395 connected to a back portion of the second side 399. The second side ear 395 is configured similar to the first side ear 385, however, in various embodiments, the second side ear 395 can, alternatively, be configured differently. The disposable wearable absorbent article 310 further includes a first fastening area 390-1 and a second fastening area 390-2.

FIG. 3B illustrates a perspective view of an outside of the disposable wearable absorbent article 310 of the embodiment of FIG. 3A, formed for wearing. In the embodiment of FIG. 3B, the first fastener 382 is fastened to the first fastening area 390-1 and the second fastener 384 is fastened to the second fastening areas 390-2.

FIG. 3C illustrates an enlarged view of a portion of a side of the disposable wearable absorbent article 310 of the embodiment of FIG. 3B. The first fastener 382 is fastened to the first fastening area 390-1 and the second fastener 384 is fastened to the second fastening area 390-2, so that the first side ear 385 fastens the front 323 to the back 327. As a result, a portion of the first side ear 385 is disposed in the front 323 and a portion of the first side ear 385 is disposed in the back 327. In this fastened configuration, the first end 353 and the third end 363 are both disposed outside of the absorbent core area 326, in the front portion of the first side 381, laterally outboard from the longitudinal edge 324 of the absorbent core 325, laterally outboard from the narrowest portion 322 of the chassis 320, and within the first side ear 385. The first end 353 is disposed proximate to an edge of the first fastener 382 and the third end 363 is disposed proximate to an edge of the second fastener 384. In some embodiments, the first and second fasteners 382, 384 can be fastened so that one or both of the first and third ends 353, 363 can be disposed at various locations, including locations laterally inboard to the narrowest portion 322 of the chassis 320, and/or laterally inboard to the longitudinal edges 324 of the absorbent core 325, and/or within the front portion of the first side 381, and/or within the absorbent core area 326. The third location 362 is longitudinally inboard to the first location 352.

In various embodiments of the present disclosure, one or more parts of or at least a portion of the anchoring subsystem 370 can be structurally associated with the first side ear 385. In some embodiments, at least a portion of the anchoring subsystem 370, or substantially all of the anchoring subsystem 370, or even all of the anchoring subsystem 370, can be discrete from, or joined to, attached to, or embedded in, or integral with the first side ear 385. In various embodiments, at least a portion of the first SAM 350 and/or the second SAM 360, or substantially all of the first SAM 350 and/or the second SAM 360, or even all of the first SAM 350 and/or the second SAM 360, can be discrete from, or joined to, or attached to, or embedded in, or integral with the first side ear 385.

In embodiments in which one or more portions of the anchoring subsystem 370 are integral with the first side ear 385, the first side ear 385 can be considered to have a first portion, which includes the integral portions of the anchoring subsystem 370, and a second portion outside of the first portion. For example, if all of the first SAM 350 and all of the second SAM 360 were integral with the first side ear 385, then the first portion would include the first SAM pathway 351 and the second SAM pathway 361, while the second portion would include the four roughly triangular sections of the first side ear 385 that are outside of the first SAM pathway 351 and the second SAM pathway 361. In such embodiments, this first portion and second portion can be configured in various ways, as described in the connection with the embodiment of FIG. 1C.

In some embodiments, the disposable wearable absorbent article 310 can be configured such that one or more loads in the article can cause tension in the anchoring subsystem 370 before the load can cause tension in a portion of the first side ear 385 that is outside of the anchoring subsystem 370. In various embodiments, the disposable wearable absorbent article 310 can be configured such that one or more loads in the article can cause greater tension in the anchoring subsystem 370 than in a portion of the first side ear 385 that is outside of the anchoring subsystem 370.

In addition to the elements previously described, the embodiment of FIG. 3C includes tension lines 375. The tension lines 375 illustrate how the first SAM 350 and the second SAM 360 can balance collected loads with obtained holding forces, so that the anchoring subsystem 370 can at least assist in holding the disposable wearable absorbent article 310 in place on a wearer. For example, the first SAM 350 can collect loads at the second end 359 and/or along the first SAM pathway 351, with loads received through various parts of the disposable wearable absorbent article 310, such as the chassis 320 and/or the first side ear 385. Also as an example, the second SAM 360 can collect loads at the third end 363 and/or along the second SAM pathway 361, with loads received through various parts of the disposable wearable absorbent article 310, such as the second fastener 384 and/or the first side ear 385.

In a further example, the first SAM 350 can obtain holding forces at the first end 353 with forces received through various parts of the disposable wearable absorbent article 310, such as the first fastener 382 and/or the first side ear 385. In a still further example, the first SAM 350 can also obtain holding forces along the first SAM pathway 351 as the first SAM 350 experiences anchoring from direct or indirect contact with a wearer's body underneath the first SAM pathway 351. As a similar example, the second SAM 360 can obtain holding forces at the fourth end 369 with forces received through various parts of the disposable wearable absorbent article 310, such as the chassis 320 and/or the first side ear 385. As another similar example, the second SAM 360 can obtain holding forces along the second SAM pathway 361 as the second SAM 350 experiences anchoring.

The anchoring subsystem 370 is configured to indirectly anchor the absorbent core 325 to a wearer, in that, while the first SAM 350 and the second SAM 360 are not directly connected to the absorbent core 325, and the first SAM pathway 351 and the second SAM pathway 361 are each disposed outside of the absorbent core area 326, loads from the absorbent core 325 can be transmitted through various parts of the disposable wearable absorbent article 310 to the first SAM 350 and/or the second SAM 360, which can balance collected loads with obtained holding forces, so that the anchoring subsystem 370 can at least assist in holding the disposable wearable absorbent article 310 in place on a wearer. As a result, the disposable wearable absorbent article 310 can feel comfortable, look attractive, and perform well as the article tends to stay in place on a wearer and not leak.

Figure 4A:
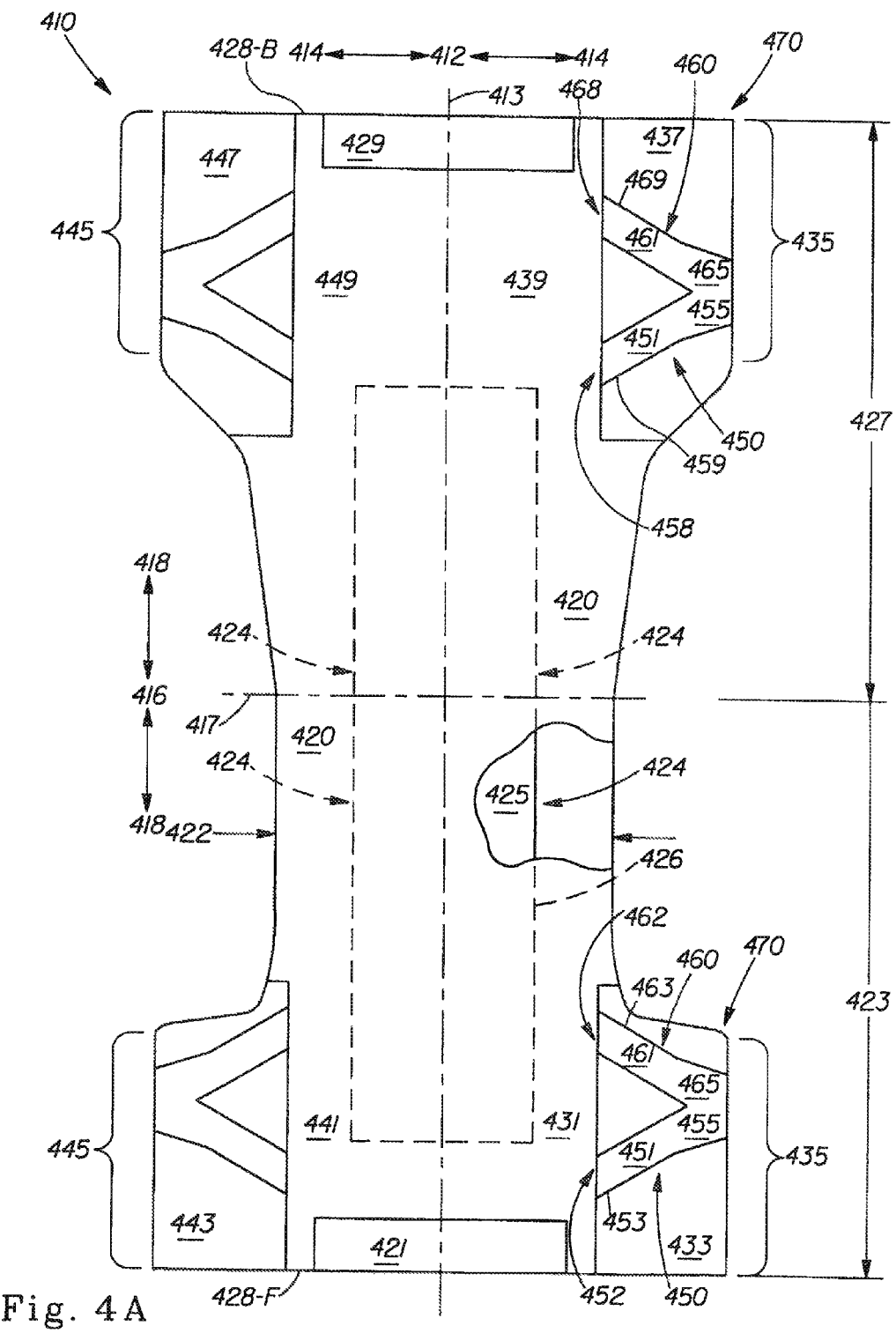
FIG. 4A illustrates a plan view of an inside of a pant-type disposable wearable absorbent article, including an anchoring subsystem with partially coextensive side anchoring members, according to embodiments of the present disclosure.

FIG. 4A illustrates a plan view of an inside of a pant-type disposable wearable absorbent article 410, including an anchoring subsystem 470 with partially coextensive side anchoring members, 450, 460, according to embodiments of the present disclosure. The disposable wearable absorbent article 410 includes a longitudinal centerline 417 and a lateral centerline 413, which provide lines of reference for referring to laterally inboard 412, laterally outboard 414, longitudinally inboard 416, and longitudinally outboard 418 relative locations of the disposable wearable absorbent article 410.

The disposable wearable absorbent article 410 also includes a chassis 420, a front waistband 421, a narrowest portion 422 of the chassis 420, a front 423, an absorbent core 425 with longitudinal edges 424, an absorbent core area 426, a back 427, a front waist edge 424-F, a back waist edge 428-B, and a back waistband 429. A portion of the chassis 420 is illustrated as cut away in order to show the absorbent core 425 and the longitudinal edges 424 more clearly. In some embodiments, the front 423 and the back 427 can be considered first and second halves of the disposable wearable absorbent article 410, although the halves may not be equal. A front portion of a first side 431 is disposed in the front 423. A back portion of the first side 439 is disposed in the back 427.

Figure 4B:
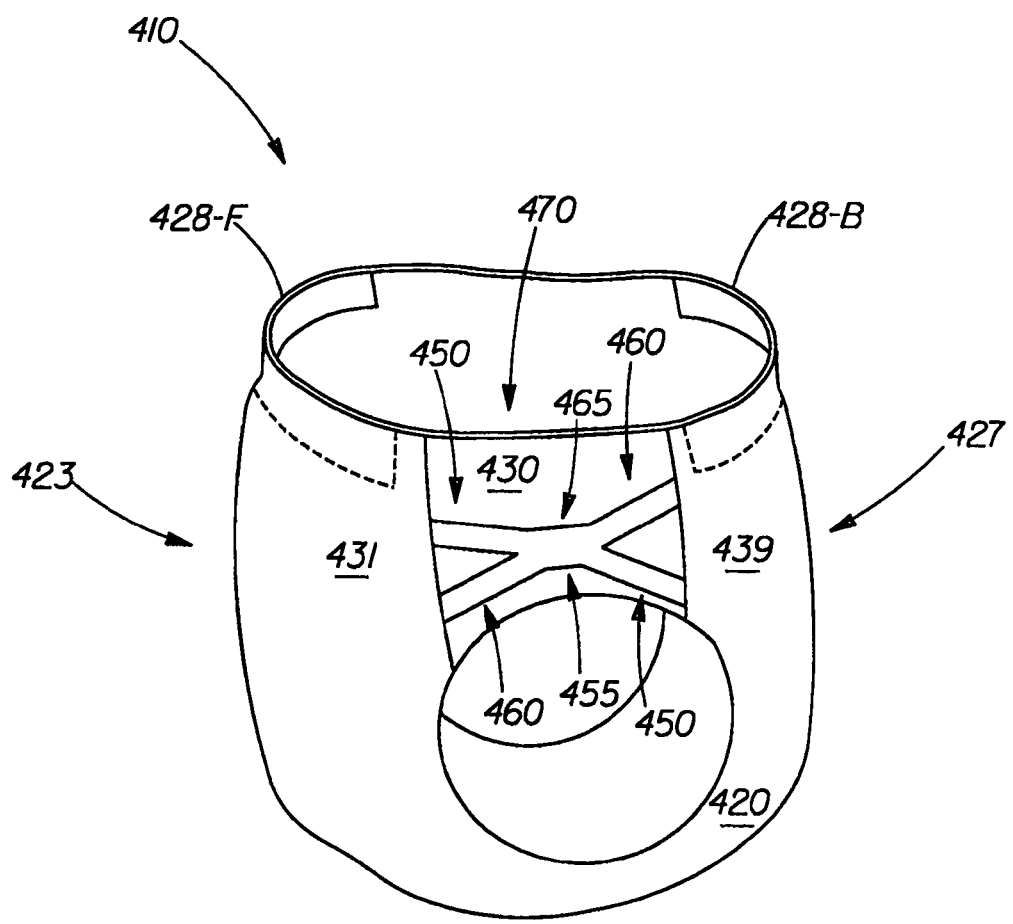
FIG. 4B illustrates a perspective view of an outside of the disposable wearable absorbent article of the embodiment of FIG. 4A, formed for wearing.
Figure 4C:
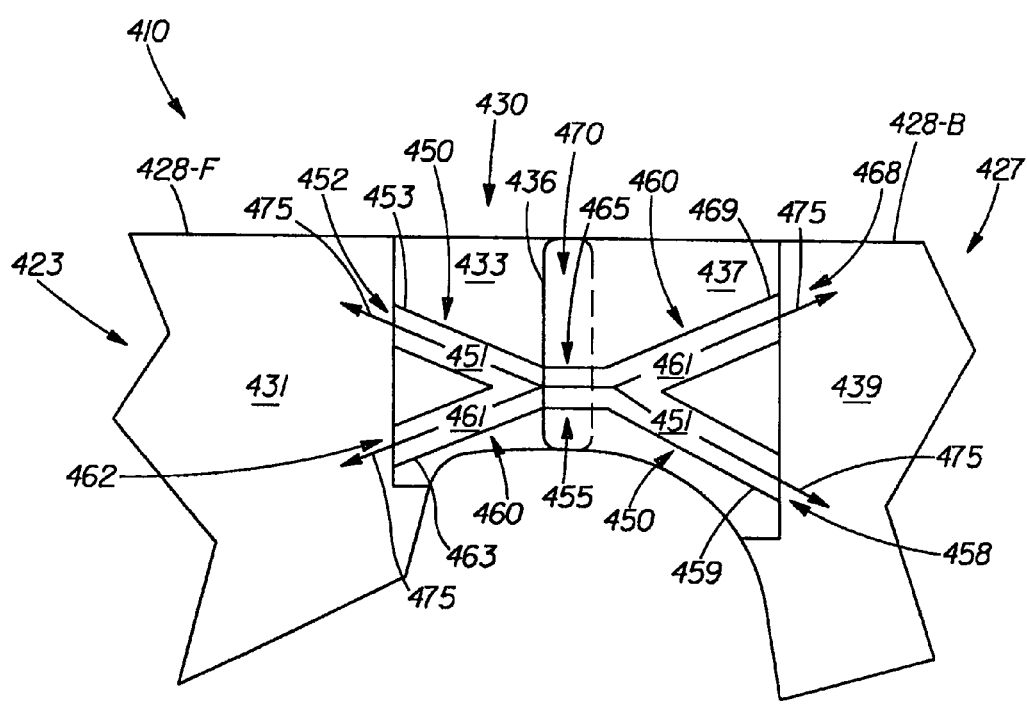
FIG. 4C illustrates an enlarged view of a portion of a side of the disposable wearable absorbent article of the embodiment of FIG. 4B.

The disposable wearable absorbent article 410 has a first side panel, which includes a front portion of the first side panel 433 and a back portion of the first side panel 437, configured to connect via a first side interface 435. The first side panel also includes the anchoring subsystem 470. The anchoring subsystem 470 includes a first SAM 450 and a second SAM 460. The first SAM 450 is disposed along a first SAM pathway 451, and includes a first end 453 disposed at a first location 452, a second end 459 disposed at a second location 458, and a first middle 455 between the first end 453 and the second end 459. The second SAM 460 is disposed along a second SAM pathway 461, and includes a third end 463 disposed at a third location 462, a fourth end 469 disposed at a fourth location 468, and a second middle 465 between the third end 463 and the fourth end 469. Portions of the first SAM pathway 451 are distinct from the second SAM pathway 461. However, a portion of the first middle 455 shares a common section of pathway with a portion of the second middle 465, so a portion of the first middle 455 is coextensive with a portion of the second middle 465. In the embodiment of FIGS. 4A-4C, the coextensive portion bridges the first side interface 435, however, in some embodiments, the SAM pathways can cross in the front portion of the first side panel 433 or in the back portion of the first side panel 437. In various embodiments, part or all of the first SAM pathway 451 and/or the second SAM pathway 461 can be configured as a geodesic, so that the anchoring subsystem 470 can provide geodesic anchoring.

The second end 459 and the fourth end 469 are both disposed outside of the absorbent core area 426, in the back portion of the first side 439, laterally outboard from the longitudinal edge 424 of the absorbent core 425, laterally inboard to the narrowest portion 422 of the chassis 420, and within the back portion of the first side panel 437 proximate to a laterally inboard edge of the back portion of the first side panel 437. In some embodiments, one or both of the second and fourth ends 459, 469 can be disposed at various locations, including locations outside of the back portion of the first side panel 437, and/or within the back portion of the first side 439, and/or laterally outboard from the narrowest portion 422 of the chassis 420, and/or laterally inboard to the longitudinal edges 424 of the absorbent core 425, and/or within the absorbent core area 426. The fourth location 468 is longitudinally outboard from the second location 458.

The first end 453 and the third end 463 are both disposed outside of the absorbent core area 426, in the front portion of the first side 431, laterally outboard from the longitudinal edge 424 of the absorbent core 425, laterally inboard to the narrowest portion 422 of the chassis 420, and within the front portion of the first side panel 433 proximate to a laterally inboard edge of the front portion of the first side panel 433. In some embodiments, one or both of the first and third ends 453, 463 can be disposed at various locations, including locations outside of the front portion of the first side panel 433, and/or within the front portion of the first side 431, and/or laterally outboard from the narrowest portion 422 of the chassis 420, and/or laterally inboard to the longitudinal edges 424 of the absorbent core 425, and/or within the absorbent core area 426. The third location 462 is longitudinally inboard to the first location 452.

The anchoring subsystem 470 is not directly connected to the absorbent core 425, and is outside of the absorbent core area 426, so the anchoring subsystem 470 is separate from the absorbent core 425. The anchoring subsystem 470 is considered a subsystem because neither the first SAM 450 nor the second SAM 460 will substantially or completely encircle the lower torso of a wearer, and because the anchoring subsystem 470 is contained within a particular, defined portion of the disposable wearable absorbent article 410. In the embodiment of FIGS. 4A-4C, the anchoring subsystem 470 is contained within the first side of the disposable wearable absorbent article 470, so the anchoring subsystem 470 is considered a side anchoring subsystem. The disposable wearable absorbent article 410 can also include an outer cover, which can, in various embodiments, be separate from the anchoring subsystem 470. In some embodiments, part or all of such an outer cover can be stretchable, elastic, or extensible.

The disposable wearable absorbent article 410 also includes a second side with a front portion of the second side 441 disposed in the front 423 and a back portion of the second side 449 disposed in the back 427. The disposable wearable absorbent article 410 has a second side panel, which includes a front portion of the second side panel 443 and a back portion of the second side panel 447, configured to connect via a second side interface 445. The second side panel is configured similar to the first side panel, however, in various embodiments, the second side panel can, alternatively, be configured differently.

FIG. 4B illustrates a perspective view of an outside of the disposable wearable absorbent article 410 of the embodiment of FIG. 4A, formed for wearing. In the embodiment of FIG. 4B, the first side is connected via the first side interface 435.

FIG. 4C illustrates an enlarged view of a portion of a side of the disposable wearable absorbent article 410 of the embodiment of FIG. 4B. A connection 436 proximate to the first side interface 435 connects the front portion of the first side panel 433 with the back portion of the first side panel 437 to form the first side. The connection 436 can take various forms, such as a fastenable connection or a durable connection. The location of the connection 436 can vary in some embodiments. In some embodiments, a side can, alternatively, be formed with more than one connection at various locations or without a distinct connection within the side.

In various embodiments of the present disclosure, one or more parts of or at least a portion of the anchoring subsystem 470 can be structurally associated with the first side panel. In some embodiments, at least a portion of the anchoring subsystem 470, or substantially all of the anchoring subsystem 470, or even all of the anchoring subsystem 470, can be discrete from, or joined to, attached to, or embedded in, or integral with the first side panel. In various embodiments, at least a portion of the first SAM 450 and/or the second SAM 460, or substantially all of the first SAM 450 and/or the second SAM 460, or even all of the first SAM 450 and/or the second SAM 460, can be discrete from, or joined to, or attached to, or embedded in, or integral with the first side panel.

In embodiments in which one or more portions of the anchoring subsystem 470 are integral with the first side panel, the first side panel can be considered to have a first portion, which includes the integral portions of the anchoring subsystem 470, and a second portion outside of the first portion. For example, if all of the first SAM 450 and all of the second SAM 460 were integral with the first side panel, then the first portion would include the first SAM pathway 451 and the second SAM pathway 461, while the second portion would include the four roughly triangular sections of the first side panel that are outside of the first SAM pathway 451 and the second SAM pathway 461. In such embodiments, this first portion and second portion can be configured in various ways, as described in the connection with the embodiment of FIG. 1C.

In some embodiments, the disposable wearable absorbent article 410 can be configured such that one or more loads in the article can cause tension in the anchoring subsystem 470 before the load can cause tension in a portion of the first side panel that is outside of the anchoring subsystem 470. In various embodiments, the disposable wearable absorbent article 410 can be configured such that one or more loads in the article can cause greater tension in the anchoring subsystem 470 than in a portion of the first side panel that is outside of the anchoring subsystem 470.

In addition to the elements previously described, the embodiment of FIG. 4C includes tension lines 475. The tension lines 475 illustrate how the first SAM 450 and the second SAM 460 can balance collected loads with obtained holding forces, so that the anchoring subsystem 470 can at least assist in holding the disposable wearable absorbent article 410 in place on a wearer. For example, the first SAM 450 can collect loads at the second end 459 and/or along the first SAM pathway 451. Also as an example, the second SAM 460 can collect loads at the third end 463 and/or along the second SAM pathway 461. In a further example, the first SAM 450 can obtain holding forces at the first end 453 and/or along the first SAM pathway 451 as the first SAM 450 experiences anchoring from direct or indirect contact with a wearer's body underneath the first SAM pathway 451. In still a further example, the second SAM 460 can obtain holding forces at the fourth end 469 and/or along the second SAM pathway 461 as the second SAM 450 experiences anchoring. These loads and forces can be received through various parts of the disposable wearable absorbent article 410, such as the chassis 420 and/or the first side panel.

The anchoring subsystem 470 is configured to indirectly anchor the absorbent core 425 to a wearer, in that, while the first SAM 450 and the second SAM 460 are not directly connected to the absorbent core 425, and the first SAM pathway 451 and the second SAM pathway 461 are each disposed outside of the absorbent core area 426, loads from the absorbent core 425 can be transmitted through various parts of the disposable wearable absorbent article 410 to the first SAM 450 and/or the second SAM 460, which can balance collected loads with obtained holding forces, so that the anchoring subsystem 470 can at least assist in holding the disposable wearable absorbent article 410 in place on a wearer. As a result, the disposable wearable absorbent article 410 can feel comfortable, look attractive, and perform well as the article tends to stay in place on a wearer and not leak.

Figure 5A:
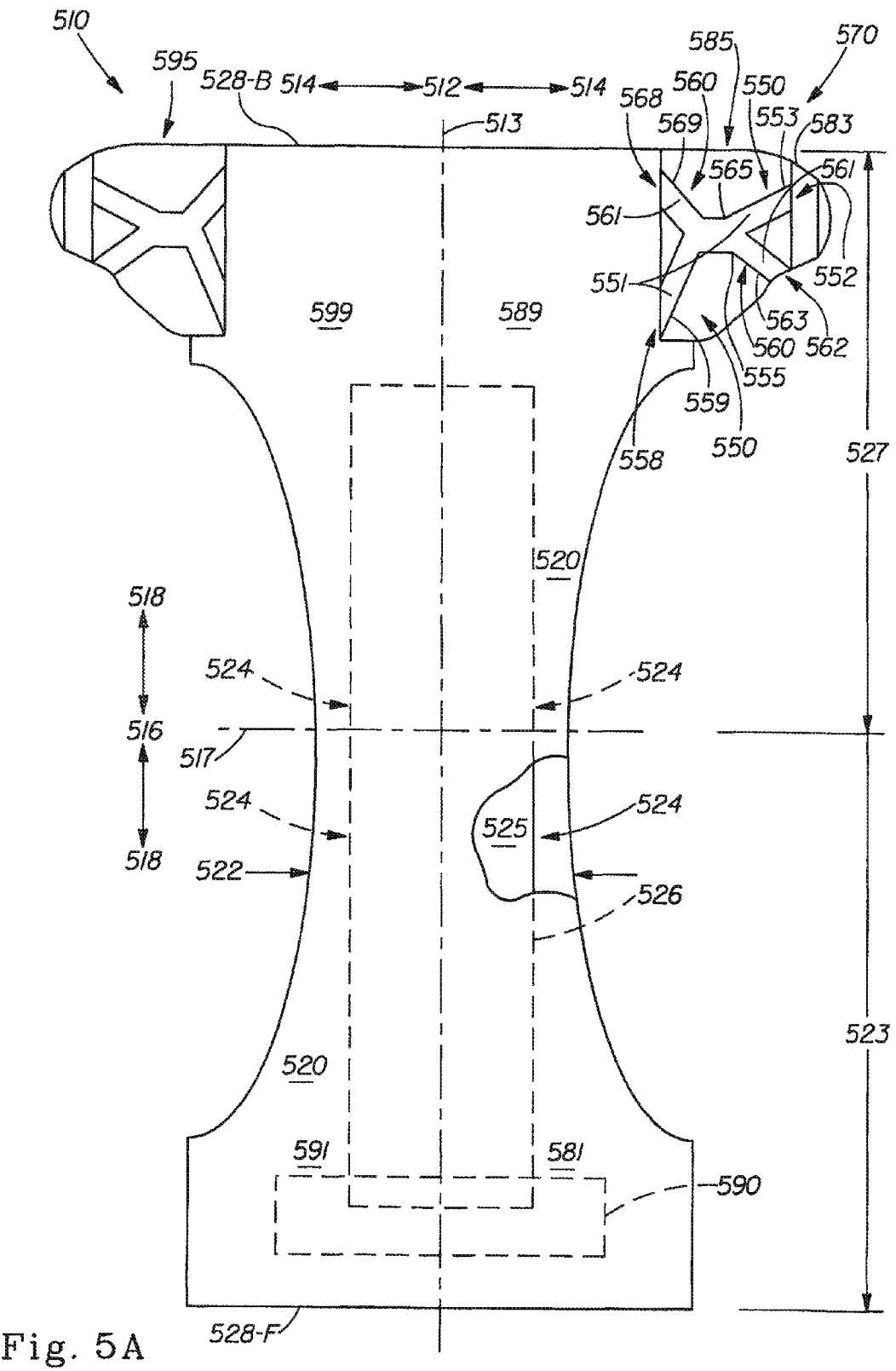
FIG. 5A illustrates a plan view of an inside of a fastenable disposable wearable absorbent article, including an anchoring subsystem with partially coextensive side anchoring members, and side ears, each with one fastener, according to embodiments of the present disclosure.

FIG. 5A illustrates a plan view of an inside of a fastenable disposable wearable absorbent article 510, including an anchoring subsystem 570 with partially coextensive side anchoring members, 550, 560, and side ears, each with one fastener, according to embodiments of the present disclosure. The disposable wearable absorbent article 510 includes a longitudinal centerline 517 and a lateral centerline 513, which provide lines of reference for referring to laterally inboard 512, laterally outboard 514, longitudinally inboard 516, and longitudinally outboard 518 relative locations of the disposable wearable absorbent article 510.

The disposable wearable absorbent article 510 also includes a chassis 520, a narrowest portion 522 of the chassis 520, a front 523, an absorbent core 525 with longitudinal edges 524, an absorbent core area 526, a back 527, a front waist edge 528-F, and a back waist edge 528-B. A portion of the chassis 520 is illustrated as cut away in order to show the absorbent core 525 and the longitudinal edges 524 more clearly. In some embodiments, the front 523 and the back 527 can be considered first and second halves of the disposable wearable absorbent article 510, although the halves may not be equal. A front portion of a first side 581 is disposed in the front 523. A back portion of the first side 589 is disposed in the back 527.

The disposable wearable absorbent article 510 has a first side ear 585 connected to the back portion of the first side 589. The first side ear 585 includes a fastener 583 and the anchoring subsystem 570. The anchoring subsystem 570 includes a first SAM 550 and a second SAM 560. The first SAM 550 is disposed along a first SAM pathway 551, and includes a first end 553 disposed at a first location 552, a second end 559 disposed at a second location 558, and a first middle 555 between the first end 553 and the second end 559. The second SAM 560 is disposed along a second SAM pathway 561, and includes a third end 563 disposed at a third location 562, a fourth end 569 disposed at a fourth location 568, and a second middle 565 between the third end 563 and the fourth end 569. Portions of the first SAM pathway 551 are distinct from the second SAM pathway 561. However, a portion of the first middle 555 shares a common section of pathway with a portion of the second middle 565, so a portion of the first middle 555 is coextensive with a portion of the second middle 565. In various embodiments, part or all of the first SAM pathway 551 and/or the second SAM pathway 561 can be configured as a geodesic, so that the anchoring subsystem 570 can provide geodesic anchoring.

The second end 559 and the fourth end 569 are both disposed outside of the absorbent core area 526, in the back portion of the first side 589, laterally outboard from the longitudinal edge 524 of the absorbent core 525, laterally outboard from the narrowest portion 522 of the chassis 520, and within the first side ear 585 proximate to a laterally inboard edge of the first side ear 585. In some embodiments, one or both of the second and fourth ends 559, 569 can be disposed at various locations, including locations outside of the first side ear 585, and/or within the back portion of the first side 589, and/or laterally inboard to the narrowest portion 522 of the chassis 520, and/or laterally inboard to the longitudinal edges 524 of the absorbent core 525, and/or within the absorbent core area 526. The fourth location 568 is longitudinally outboard from the second location 558. The first end 553 and the third end 563 are both disposed within the first side ear 585. The dispositions of the first and third ends 553, 563 are further described in connection with the embodiment of FIG. 5C.

Figure 5B:
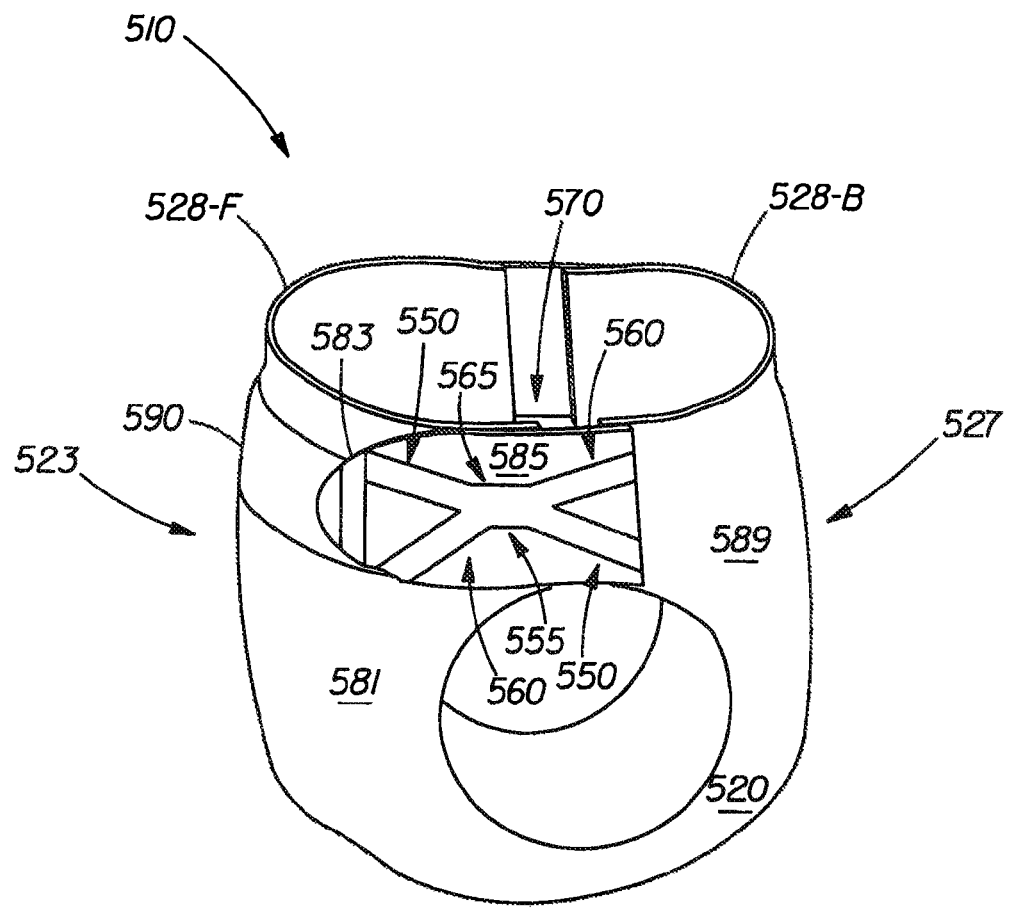
FIG. 5B illustrates a perspective view of an outside of the disposable wearable absorbent article of the embodiment of FIG. 5A, formed for wearing.
Figure 5C:
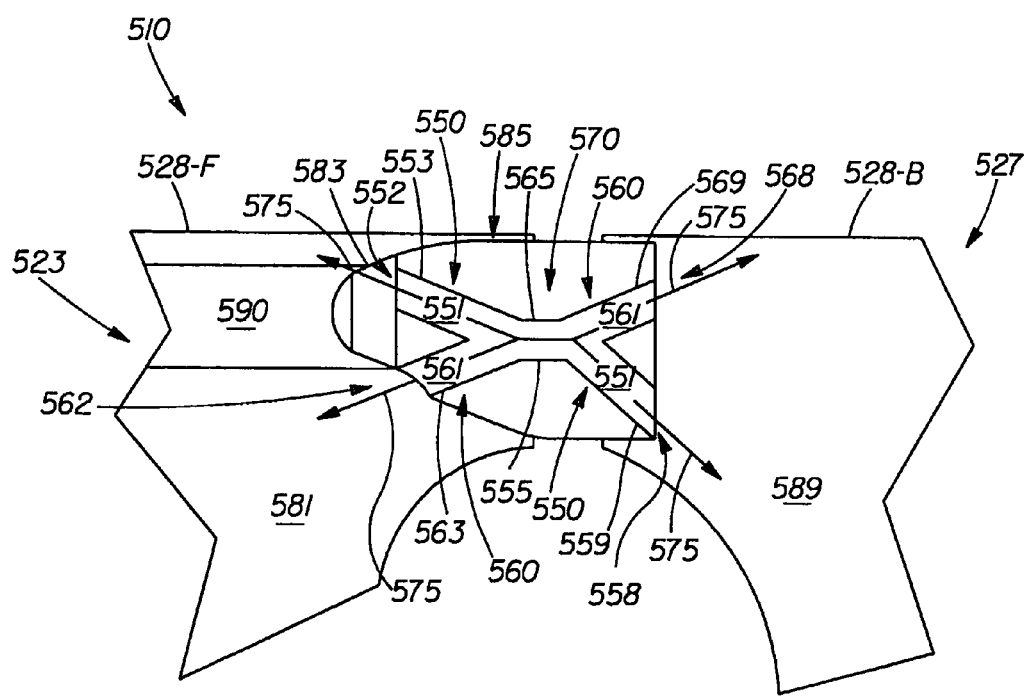
FIG. 5C illustrates an enlarged view of a portion of a side of the disposable wearable absorbent article of the embodiment of FIG. 5B.

The anchoring subsystem 570 is not directly connected to the absorbent core 525, and is outside of the absorbent core area 526, so the anchoring subsystem 570 is separate from the absorbent core 525. The anchoring subsystem 570 is considered a subsystem because neither the first SAM 550 nor the second SAM 560 will substantially or completely encircle the lower torso of a wearer, and because the anchoring subsystem 570 is contained within a particular, defined portion of the disposable wearable absorbent article 510. In the embodiment of FIGS. 5A-5C, the anchoring subsystem 570 is contained within the first side of the disposable wearable absorbent article 570, so the anchoring subsystem 570 is considered a side anchoring subsystem. The disposable wearable absorbent article 510 can also include an outer cover, which can, in various embodiments, be separate from the anchoring subsystem 570. In some embodiments, part or all of such an outer cover can be stretchable, elastic, or extensible.

The disposable wearable absorbent article 510 also includes a front portion of a second side 591, a second side ear 595 connected to a back portion of the second side 599. The second side ear 595 is configured similar to the first side ear 585, however, in various embodiments, the second side ear 595 can, alternatively, be configured differently. The disposable wearable absorbent article 510 further includes a fastening area 590.

FIG. 5B illustrates a perspective view of an outside of the disposable wearable absorbent article 510 of the embodiment of FIG. 5A, formed for wearing. In the embodiment of FIG. 5B, the fastener 583 is fastened to the fastening area 590.

FIG. 5C illustrates an enlarged view of a portion of a side of the disposable wearable absorbent article 510 of the embodiment of FIG. 5B. The fastener 583 is fastened to the fastening area 590, so that the first side ear 585 fastens the front 523 to the back 527. As a result, a portion of the first side ear 585 is disposed in the front 523 and a portion of the first side ear 585 is disposed in the back 527. In this fastened configuration, the first end 553 and the third end 563 are both disposed outside of the absorbent core area 526, in the front portion of the first side 581, laterally outboard from the longitudinal edge 524 of the absorbent core 525, laterally outboard from the narrowest portion 522 of the chassis 520, and within the first side ear 585. The first end 553 is disposed proximate to a laterally inboard edge of the fastener 583 and the third end 563 is disposed proximate to a longitudinally inboard edge of the first side ear 585. In various embodiments, the third end 563 can also be disposed proximate to an edge of the fastener 583. In some embodiments, the fastener 583 can be fastened so that one or both of the first and third ends 553, 563 can be disposed at various locations, including locations laterally inboard to the narrowest portion 522 of the chassis 520, and/or laterally inboard to the longitudinal edges 524 of the absorbent core 525, and/or within the front portion of the first side 581, and/or within the absorbent core area 526. The third location 562 is longitudinally inboard to the first location 552. In variations of the embodiment of FIGS. 5A-5C, the first side ear 585 can also include a passive fastener disposed proximate to the third end 563 of the second SAM 560, as described in the embodiment of FIG. 2D.

In various embodiments of the present disclosure, one or more parts of or at least a portion of the anchoring subsystem 570 can be structurally associated with the first side ear 585. In some embodiments, at least a portion of the anchoring subsystem 570, or substantially all of the anchoring subsystem 570, or even all of the anchoring subsystem 570, can be discrete from, or joined to, attached to, or embedded in, or integral with the first side ear 585. In various embodiments, at least a portion of the first SAM 550 and/or the second SAM 560, or substantially all of the first SAM 550 and/or the second SAM 560, or even all of the first SAM 550 and/or the second SAM 560, can be discrete from, or joined to, attached to, or embedded in, or integral with the first side ear 585.

In embodiments in which one or more portions of the anchoring subsystem 570 are integral with the first side ear 585, the first side ear 585 can be considered to have a first portion, which includes the integral portions of the anchoring subsystem 570, and a second portion outside of the first portion. For example, if all of the first SAM 550 and all of the second SAM 560 were integral with the first side ear 585, then the first portion would include the first SAM pathway 551 and the second SAM pathway 561, while the second portion would include the four roughly triangular sections of the first side ear 585 that are outside of the first SAM pathway 551 and the second SAM pathway 561. In such embodiments, this first portion and second portion can be configured in various ways, as described in the connection with the embodiment of FIG. 1C.

In some embodiments, the disposable wearable absorbent article 510 can be configured such that one or more loads in the article can cause tension in the anchoring subsystem 570 before the load can cause tension in a portion of the first side ear 585 that is outside of the anchoring subsystem 570. In various embodiments, the disposable wearable absorbent article 510 can be configured such that one or more loads in the article can cause greater tension in the anchoring subsystem 570 than in a portion of the first side ear 585 that is outside of the anchoring subsystem 570.

In addition to the elements previously described, the embodiment of FIG. 5C includes tension lines 575. The tension lines 575 illustrate how the first SAM 550 and the second SAM 560 can balance collected loads with obtained holding forces, so that the anchoring subsystem 570 can at least assist in holding the disposable wearable absorbent article 510 in place on a wearer. For example, the first SAM 550 can collect loads at the second end 559 and/or along the first SAM pathway 551, with loads received through various parts of the disposable wearable absorbent article 510, such as the chassis 520 and/or the first side ear 585. Also as an example, the second SAM 560 can collect loads at the third end 563 and/or along the second SAM pathway 561, with loads received through various parts of the disposable wearable absorbent article 510, such as the fastener 583 and/or the first side ear 585.

In a further example, the first SAM 550 can obtain holding forces at the first end 553 with forces received through various parts of the disposable wearable absorbent article 510, such as the fastener 583 and/or the first side ear 585. In a still further example, the first SAM 550 can also obtain holding forces along the first SAM pathway 551 as the first SAM 550 experiences anchoring from direct or indirect contact with a wearer's body underneath the first SAM pathway 551. As a similar example, the second SAM 560 can obtain holding forces at the fourth end 569 with forces received through various parts of the disposable wearable absorbent article 510, such as the chassis 520 and/or the first side ear 585. As another similar example, the second SAM 560 can obtain holding forces along the second SAM pathway 561 as the second SAM 550 experiences anchoring.

The anchoring subsystem 570 is configured to indirectly anchor the absorbent core 525 to a wearer, in that, while the first SAM 550 and the second SAM 560 are not directly connected to the absorbent core 525, and the first SAM pathway 551 and the second SAM pathway 561 are each disposed outside of the absorbent core area 526, loads from the absorbent core 525 can be transmitted through various parts of the disposable wearable absorbent article 510 to the first SAM 550 and/or the second SAM 560, which can balance collected loads with obtained holding forces, so that the anchoring subsystem 570 can at least assist in holding the disposable wearable absorbent article 510 in place on a wearer. As a result, the disposable wearable absorbent article 510 can feel comfortable, look attractive, and perform well as the article tends to stay in place on a wearer and not leak.

Figure 6A:
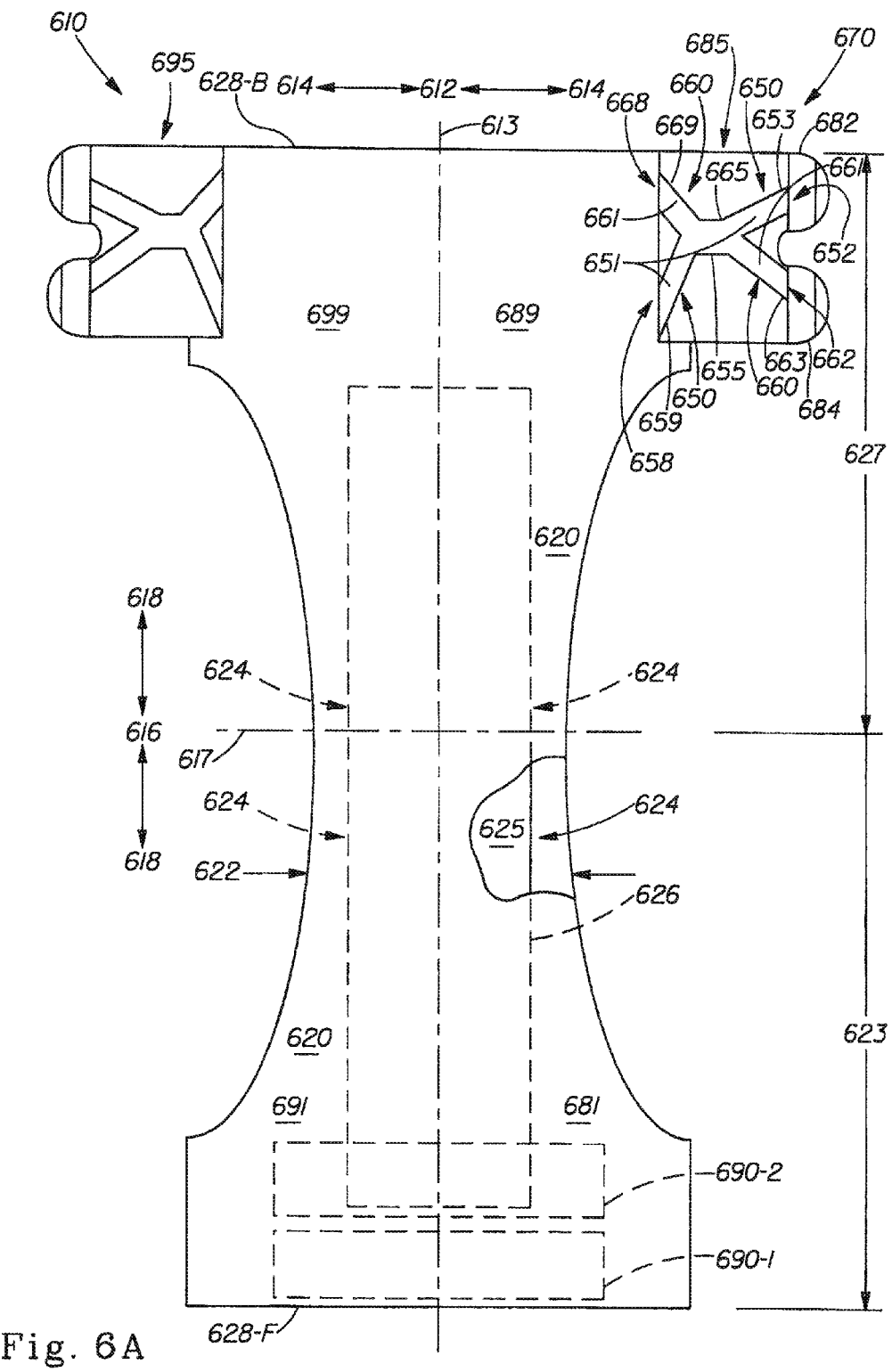
FIG. 6A illustrates a plan view of an inside of a fastenable disposable wearable absorbent article, including an anchoring subsystem with partially coextensive side anchoring members, and side ears, each with two fasteners, according to embodiments of the present disclosure.

FIG. 6A illustrates a plan view of an inside of a fastenable disposable wearable absorbent article 610, including an anchoring subsystem 670 with partially coextensive side anchoring members, 650, 660, and side ears, 685, 695, each with two fasteners, according to embodiments of the present disclosure. The disposable wearable absorbent article 610 includes a longitudinal centerline 617 and a lateral centerline 613, which provide lines of reference for referring to laterally inboard 612, laterally outboard 614, longitudinally inboard 616, and longitudinally outboard 618 relative locations of the disposable wearable absorbent article 610.

The disposable wearable absorbent article 610 also includes a chassis 620, a narrowest portion 622 of the chassis 620, a front 623, an absorbent core 625 with longitudinal edges 624, an absorbent core area 626, a back 627, a front waist edge 628-F, and a back waist edge 628-B. A portion of the chassis 620 is illustrated as cut away in order to show the absorbent core 625 and the longitudinal edges 624 more clearly. In some embodiments, the front 623 and the back 627 can be considered first and second halves of the disposable wearable absorbent article 610, although the halves may not be equal. A front portion of a first side 681 is disposed in the front 623. A back portion of the first side 689 is disposed in the back 627.

The disposable wearable absorbent article 610 has a first side ear 685 connected to the back portion of the first side 689. The first side ear 685 includes a first fastener 682, a second fastener 684, and the anchoring subsystem 670. The anchoring subsystem 670 includes a first SAM 650 and a second SAM 660. The first SAM 650 is disposed along a first SAM pathway 651, and includes a first end 653 disposed at a first location 652, a second end 659 disposed at a second location 658, and a first middle 655 between the first end 653 and the second end 659. The second SAM 660 is disposed along a second SAM pathway 661, and includes a third end 663 disposed at a third location 662, a fourth end 669 disposed at a fourth location 668, and a second middle 665 between the third end 663 and the fourth end 669. Portions of the first SAM pathway 651 are distinct from the second SAM pathway 661. However, a portion of the first middle 655 shares a common section of pathway with a portion of the second middle 665, so a portion of the first middle 655 is coextensive with a portion of the second middle 665. In various embodiments, part or all of the first SAM pathway 651 and/or the second SAM pathway 661 can be configured as a geodesic, so that the anchoring subsystem 670 can provide geodesic anchoring.

The second end 659 and the fourth end 669 are both disposed outside of the absorbent core area 626, in the back portion of the first side 689, laterally outboard from the longitudinal edge 624 of the absorbent core 625, laterally outboard from the narrowest portion 622 of the chassis 620, and within the first side ear 685 proximate to a laterally inboard edge of the first side ear 685. In some embodiments, one or both of the second and fourth ends 659, 669 can be disposed at various locations, including locations outside of the first side ear 685, and/or within the back portion of the first side 689, and/or laterally inboard to the narrowest portion 622 of the chassis 620, and/or laterally inboard to the longitudinal edges 624 of the absorbent core 625, and/or within the absorbent core area 626. The fourth location 668 is longitudinally outboard from the second location 658. The first end 653 and the third end 663 are both disposed within the first side ear 685. The dispositions of the first and third ends 653, 663 are further described in connection with the embodiment of FIG. 6C.

Figure 6B:
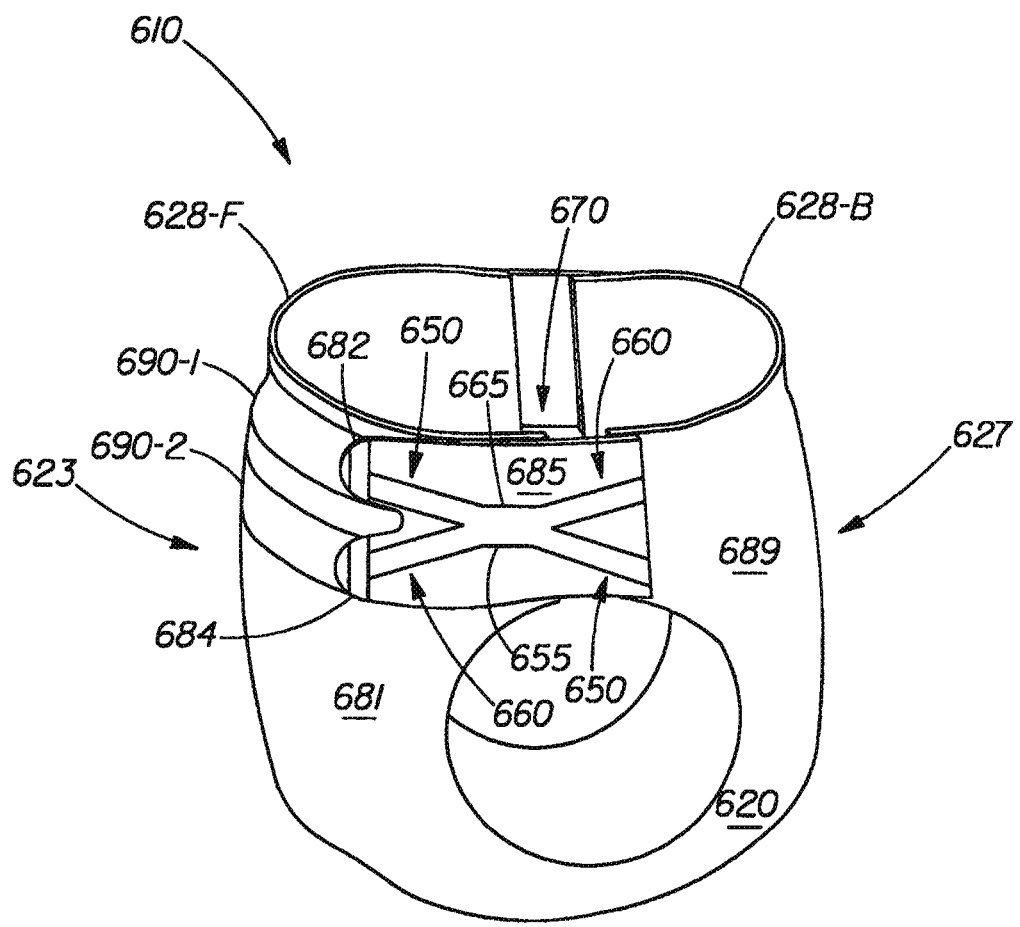
FIG. 6B illustrates a perspective view of an outside of the disposable wearable absorbent article of the embodiment of FIG. 6A, formed for wearing.
Figure 6C:
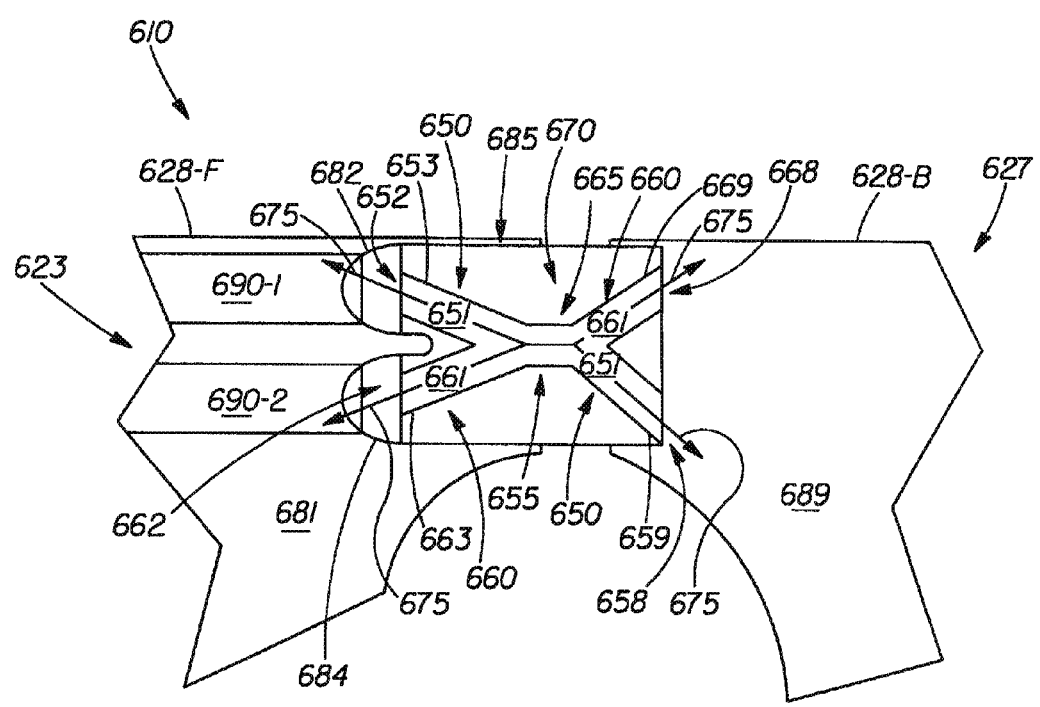
FIG. 6C illustrates an enlarged view of a portion of a side of the disposable wearable absorbent article of the embodiment of FIG. 6B.

The anchoring subsystem 670 is not directly connected to the absorbent core 625, and is outside of the absorbent core area 626, so the anchoring subsystem 670 is separate from the absorbent core 625. The anchoring subsystem 670 is considered a subsystem because neither the first SAM 650 nor the second SAM 660 will substantially or completely encircle the lower torso of a wearer, and because the anchoring subsystem 670 is contained within a particular, defined portion of the disposable wearable absorbent article 610. In the embodiment of FIGS. 6A-6C, the anchoring subsystem 670 is contained within the first side of the disposable wearable absorbent article 670, so the anchoring subsystem 670 is considered a side anchoring subsystem. The disposable wearable absorbent article 610 can also include an outer cover, which can, in various embodiments, be separate from the anchoring subsystem 670. In some embodiments, part or all of such an cover can be stretchable, elastic, or extensible.

The disposable wearable absorbent article 610 also includes a front portion of a second side 691, a second side ear 695 connected to a back portion of the second side 699. The second side ear 695 is configured similar to the first side ear 685, however, in various embodiments, the second side ear 695 can, alternatively, be configured differently. The disposable wearable absorbent article 610 further includes a first fastening area 690-1 and a second fastening area 690-2.

FIG. 6B illustrates a perspective view of an outside of the disposable wearable absorbent article 610 of the embodiment of FIG. 6A, formed for wearing. In the embodiment of FIG. 6B, the first fastener 682 is fastened to the first fastening area 690-1 and the second fastener 684 is fastened to the second fastening areas 690-2.

FIG. 6C illustrates an enlarged view of a portion of a side of the disposable wearable absorbent article 610 of the embodiment of FIG. 6B. The first fastener 682 is fastened to the first fastening area 690-1 and the second fastener 684 is fastened to the second fastening area 690-2, so that the first side ear 685 fastens the front 623 to the back 627. As a result, a portion of the first side ear 685 is disposed in the front 623 and a portion of the first side ear 685 is disposed in the back 627. In this fastened configuration, the first end 653 and the third end 663 are both disposed outside of the absorbent core area 626, in the front portion of the first side 681, laterally outboard from the longitudinal edge 624 of the absorbent core 625, laterally outboard from the narrowest portion 622 of the chassis 620, and within the first side ear 685. The first end 653 is disposed proximate to an edge of the first fastener 682 and the third end 663 is disposed proximate to an edge of the second fastener 684. In some embodiments, the first and second fasteners 682, 684 can be fastened so that one or both of the first and third ends 653, 663 can be disposed at various locations, including locations laterally inboard to the narrowest portion 622 of the chassis 620, and/or laterally inboard to the longitudinal edges 624 of the absorbent core 625, and/or within the front portion of the first side 681, and/or within the absorbent core area 626. The third location 662 is longitudinally inboard to the first location 652.

In various embodiments of the present disclosure, one or more parts of or at least a portion of the anchoring subsystem 670 can be structurally associated with the first side ear 685. In some embodiments, at least a portion of the anchoring subsystem 670, or substantially all of the anchoring subsystem 670, or even all of the anchoring subsystem 670, can be discrete from, or joined to, attached to, or embedded in, or integral with the first side ear 685. In various embodiments, at least a portion of the first SAM 650 and/or the second SAM 660, or substantially all of the first SAM 650 and/or the second SAM 660, or even all of the first SAM 650 and/or the second SAM 660, can be discrete from, or joined to, or attached to, or embedded in, or integral with the first side ear 685.

In embodiments in which one or more portions of the anchoring subsystem 670 are integral with the first side ear 685, the first side ear 685 can be considered to have a first portion, which includes the integral portions of the anchoring subsystem 670, and a second portion outside of the first portion. For example, if all of the first SAM 650 and all of the second SAM 660 were integral with the first side ear 685, then the first portion would include the first SAM pathway 651 and the second SAM pathway 661, while the second portion would include the four roughly triangular sections of the first side ear 685 that are outside of the first SAM pathway 651 and the second SAM pathway 661. In such embodiments, this first portion and second portion can be configured in various ways, as described in the connection with the embodiment of FIG. 1C.

In some embodiments, the disposable wearable absorbent article 610 can be configured such that one or more loads in the article can cause tension in the anchoring subsystem 670 before the load can cause tension in a portion of the first side ear 685 that is outside of the anchoring subsystem 670. In various embodiments, the disposable wearable absorbent article 610 can be configured such that one or more loads in the article can cause greater tension in the anchoring subsystem 670 than in a portion of the first side ear 685 that is outside of the anchoring subsystem 670.

In addition to the elements previously described, the embodiment of FIG. 6C includes tension lines 675. The tension lines 675 illustrate how the first SAM 650 and the second SAM 660 can balance collected loads with obtained holding forces, so that the anchoring subsystem 670 can at least assist in holding the disposable wearable absorbent article 610 in place on a wearer. For example, the first SAM 650 can collect loads at the second end 659 and/or along the first SAM pathway 651, with loads received through various parts of the disposable wearable absorbent article 610, such as the chassis 620 and/or the first side ear 685. Also as an example, the second SAM 660 can collect loads at the third end 663 and/or along the second SAM pathway 661, with loads received through various parts of the disposable wearable absorbent article 610, such as the second fastener 684 and/or the first side ear 685.

In a further example, the first SAM 650 can obtain holding forces at the first end 653 with forces received through various parts of the disposable wearable absorbent article 610, such as the first fastener 682 and/or the first side ear 685. In a still further example, the first SAM 650 can also obtain holding forces along the first SAM pathway 651 as the first SAM 650 experiences anchoring from direct or indirect contact with a wearer's body underneath the first SAM pathway 651. As a similar example, the second SAM 660 can obtain holding forces at the fourth end 669 with forces received through various parts of the disposable wearable absorbent article 610, such as the chassis 620 and/or the first side ear 685. As another similar example, the second SAM 660 can obtain holding forces along the second SAM pathway 661 as the second SAM 650 experiences anchoring.

The anchoring subsystem 670 is configured to indirectly anchor the absorbent core 625 to a wearer, in that, while the first SAM 650 and the second SAM 660 are not directly connected to the absorbent core 625, and the first SAM pathway 651 and the second SAM pathway 661 are each disposed outside of the absorbent core area 626, loads from the absorbent core 625 can be transmitted through various parts of the disposable wearable absorbent article 610 to the first SAM 650 and/or the second SAM 660, which can balance collected loads with obtained holding forces, so that the anchoring subsystem 670 can at least assist in holding the disposable wearable absorbent article 610 in place on a wearer. As a result, the disposable wearable absorbent article 610 can feel comfortable, look attractive, and perform well as the article tends to stay in place on a wearer and not leak.

Figure 7A:
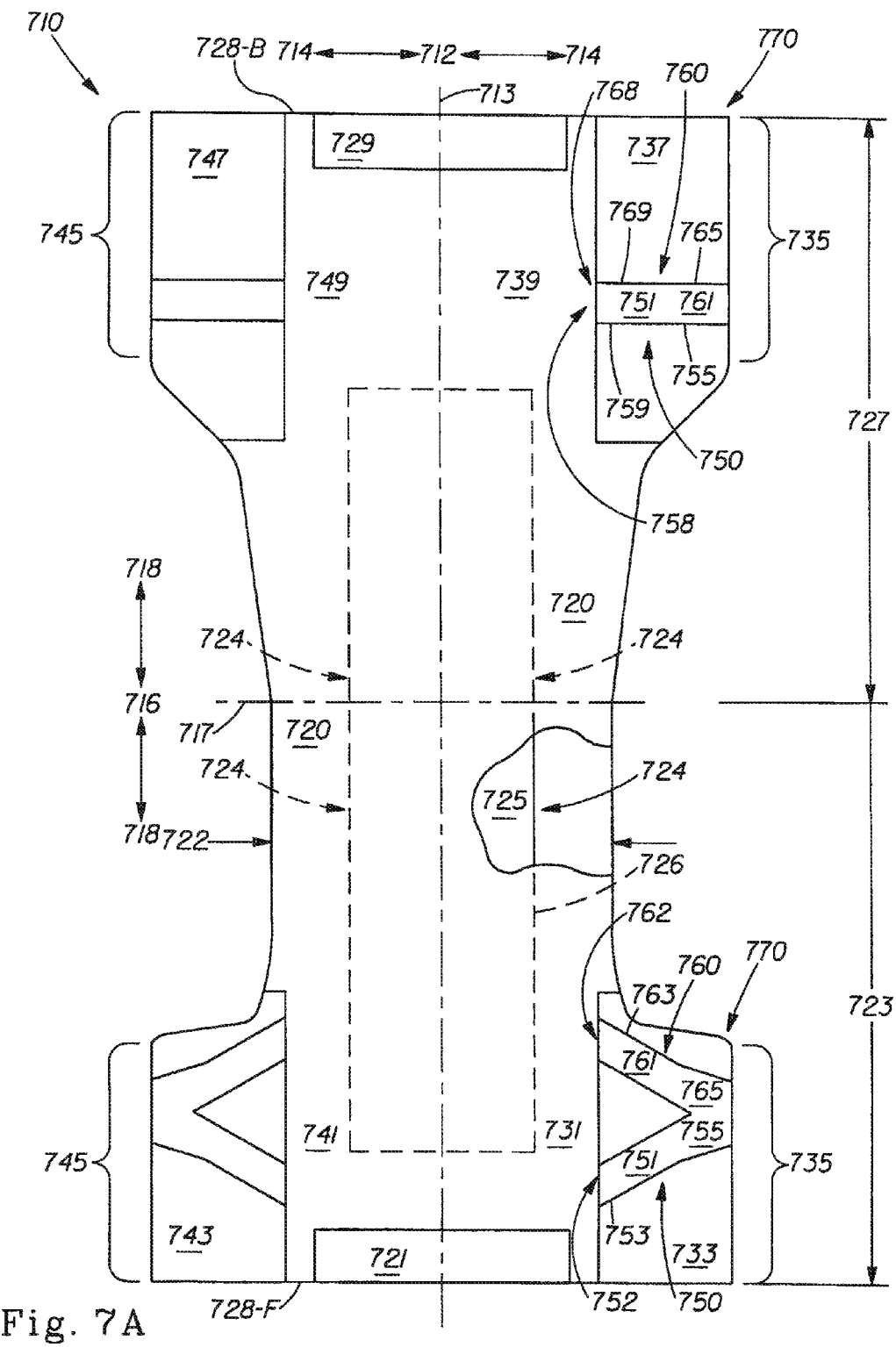
FIG. 7A illustrates a plan view of an inside of a pant-type disposable wearable absorbent article, including an anchoring subsystem with partially coextensive and partially coterminous side anchoring members, according to embodiments of the present disclosure.

FIG. 7A illustrates a plan view of an inside of a pant-type disposable wearable absorbent article 710, including an anchoring subsystem 770 with partially coextensive and partially coterminous side anchoring members, 750, 760, according to embodiments of the present disclosure. The disposable wearable absorbent article 710 includes a longitudinal centerline 717 and a lateral centerline 713, which provide lines of reference for referring to laterally inboard 712, laterally outboard 714, longitudinally inboard 716, and longitudinally outboard 718 relative locations of the disposable wearable absorbent article 710.

The disposable wearable absorbent article 710 also includes a chassis 720, a front waistband 721, a narrowest portion 722 of the chassis 720, a front 723, an absorbent core 725 with longitudinal edges 724, an absorbent core area 726, a back 727, a front waist edge 728-F, a back waist edge 728-B, and a back waistband 729. A portion of the chassis 720 is illustrated as cut away in order to show the absorbent core 725 and the longitudinal edges 724 more clearly. In some embodiments, the front 723 and the back 727 can be considered first and second halves of the disposable wearable absorbent article 710, although the halves may not be equal. A front portion of a first side 731 is disposed in the front 723. A back portion of the first side 739 is disposed in the back 727.

The disposable wearable absorbent article 710 has a first side panel, which includes a front portion of the first side panel 733 and a back portion of the first side panel 737, configured to connect via a first side interface 735. The first side panel also includes the anchoring subsystem 770. The anchoring subsystem 770 includes a first SAM 750 and a second SAM 760. The first SAM 750 is disposed along a first SAM pathway 751, and includes a first end 753 disposed at a first location 752, a second end 759 disposed at a second location 758, and a first middle 755 between the first end 753 and the second end 759. The second SAM 760 is disposed along a second SAM pathway 761, and includes a third end 763 disposed at a third location 762, a fourth end 769 disposed at a fourth location 768, and a second middle 765 between the third end 763 and the fourth end 769.

Figure 7B:
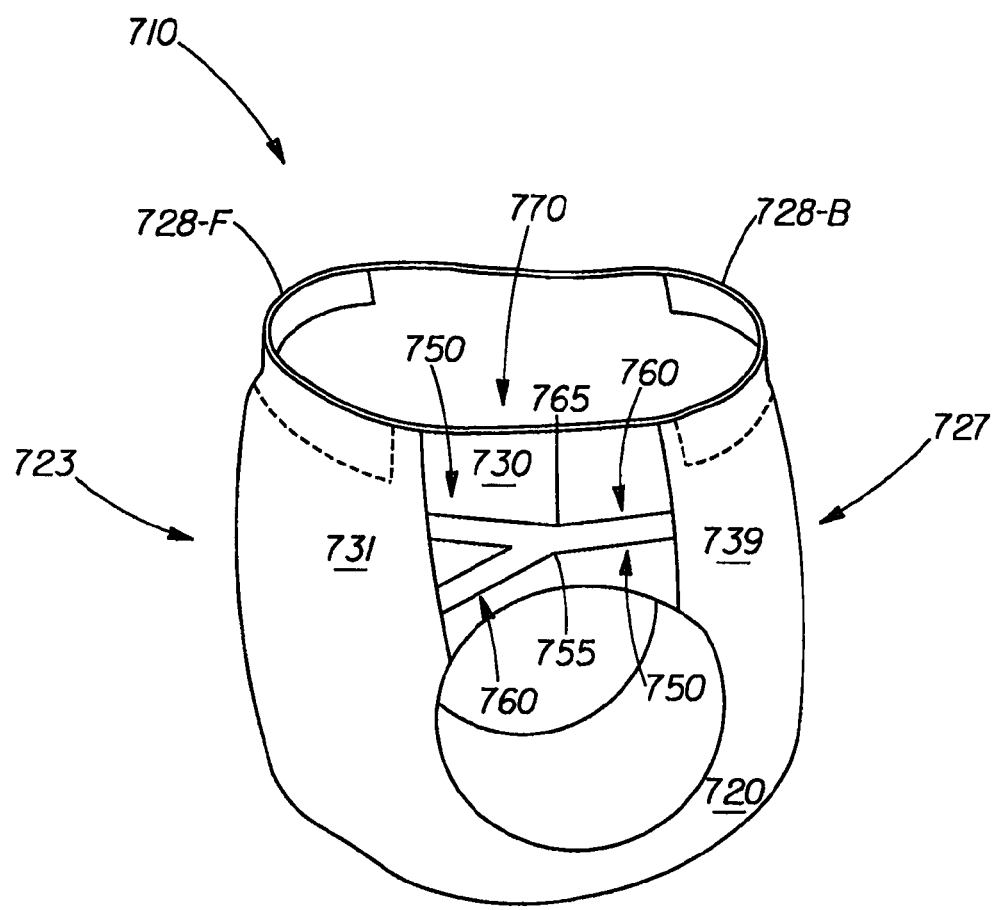
FIG. 7B illustrates a perspective view of an outside of the disposable wearable absorbent article of the embodiment of FIG. 7A, formed for wearing.
Figure 7C:
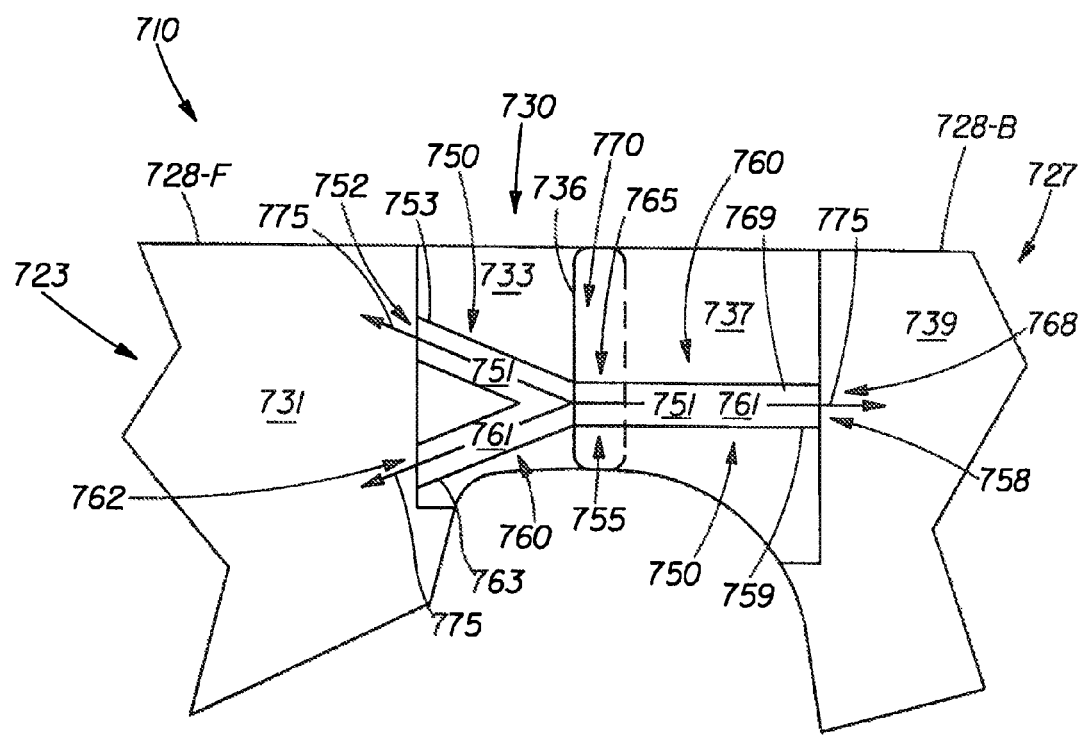
FIG. 7C illustrates an enlarged view of a portion of a side of the disposable wearable absorbent article of the embodiment of FIG. 7B.

A portion of the first SAM pathway 751 from about the first end 753 to about the first middle 755 is distinct from a portion of the second SAM pathway 761 from about the third end 763 to about the second middle 765. However, a portion of the first SAM pathway 751 from about the first middle 755 to the second end 759 shares a common section of pathway with a portion of the second SAM pathway 761 from about the second middle 765 to the fourth end 769. As a result, a portion of the first SAM pathway 751 is coextensive with a portion of the second SAM pathway 761. In the embodiment of FIGS. 7A-7C, the coextensive portion begins in the front portion of the first side panel 733, however, in some embodiments, the coextensive portion can begin in the back portion of the first side panel 737. In an alternate embodiment of the disposable wearable absorbent article 710, the first and second SAM pathways 751 and 761 can be mirrored, front to back, so that the pathways are coextensive in the front portion of the first side panel 733 and distinct in the back portion of the first side panel 737. In various embodiments, part or all of the first SAM pathway 751 and/or the second SAM pathway 761 can be configured as a geodesic, so that the anchoring subsystem 770 can provide geodesic anchoring.

The second end 759 and the fourth end 769 are both disposed outside of the absorbent core area 726, in the back portion of the first side 739, laterally outboard from the longitudinal edge 724 of the absorbent core 725, laterally inboard to the narrowest portion 722 of the chassis 720, and within the back portion of the first side panel 737 proximate to a laterally inboard edge of the back portion of the first side panel 737. In some embodiments, one or both of the second and fourth ends 759, 769 can be disposed at various locations, including locations outside of the back portion of the first side panel 737, and/or within the back portion of the first side 739, and/or laterally outboard from the narrowest portion 722 of the chassis 720, and/or laterally inboard to the longitudinal edges 724 of the absorbent core 725, and/or within the absorbent core area 726. The fourth location 768 is longitudinally outboard from the second location 758. The second location 758 at least partially overlaps with the fourth location 768, so that the first SAM pathway 851 and the second SAM pathway 861 are coterminous at their second and fourth ends 759, 769. In some embodiments, the second location 758 can substantially or completely coincide with the fourth location 768.

The first end 753 and the third end 763 are both disposed outside of the absorbent core area 726, in the front portion of the first side 731, laterally outboard from the longitudinal edge 724 of the absorbent core 725, laterally inboard to the narrowest portion 722 of the chassis 720, and within the front portion of the first side panel 733 proximate to a laterally inboard edge of the front portion of the first side panel 733. In some embodiments, one or both of the first and third ends 753, 763 can be disposed at various locations, including locations outside of the front portion of the first side panel 733, and/or within the front portion of the first side 731, and/or laterally outboard from the narrowest portion 722 of the chassis 720, and/or laterally inboard to the longitudinal edges 724 of the absorbent core 725, and/or within the absorbent core area 726. The third location 762 is longitudinally inboard to the first location 752.

The anchoring subsystem 770 is not directly connected to the absorbent core 725, and is outside of the absorbent core area 726, so the anchoring subsystem 770 is separate from the absorbent core 725. The anchoring subsystem 770 is considered a subsystem because neither the first SAM 750 nor the second SAM 760 will substantially or completely encircle the lower torso of a wearer, and because the anchoring subsystem 770 is contained within a particular, defined portion of the disposable wearable absorbent article 710. In the embodiment of FIGS. 7A-7C, the anchoring subsystem 770 is contained within the first side of the disposable wearable absorbent article 770, so the anchoring subsystem 770 is considered a side anchoring subsystem. The disposable wearable absorbent article 710 can also include an outer cover, which can, in various embodiments, be separate from the anchoring subsystem 770. In some embodiments, part or all of such an outer cover can be stretchable, elastic, or extensible.

The disposable wearable absorbent article 710 also includes a second side with a front portion of the second side 741 disposed in the front 723 and a back portion of the second side 749 disposed in the back 727. The disposable wearable absorbent article 710 has a second side panel, which includes a front portion of the second side panel 743 and a back portion of the second side panel 747, configured to connect via a second side interface 745. The second side panel is configured similar to the first side panel, however, in various embodiments, the second side panel can, alternatively, be configured differently.

FIG. 7B illustrates a perspective view of an outside of the disposable wearable absorbent article 710 of the embodiment of FIG. 7A, formed for wearing. In the embodiment of FIG. 7B, the first side is connected via the first side interface 735.

FIG. 7C illustrates an enlarged view of a portion of a side of the disposable wearable absorbent article 710 of the embodiment of FIG. 7B. A connection 736 proximate to the first side interface 735 connects the front portion of the first side panel 733 with the back portion of the first side panel 737 to form the first side. The connection 736 can take various forms, such as a fastenable connection or a durable connection. The location of the connection 736 can vary in some embodiments. In some embodiments, a side can, alternatively, be formed with more than one connection at various locations or without a distinct connection within the side.

In various embodiments of the present disclosure, one or more parts of or at least a portion of the anchoring subsystem 770 can be structurally associated with the first side panel. In some embodiments, at least a portion of the anchoring subsystem 770, or substantially all of the anchoring subsystem 770, or even all of the anchoring subsystem 770, can be discrete from, or joined to, attached to, or embedded in, or integral with the first side panel. In various embodiments, at least a portion of the first SAM 750 and/or the second SAM 760, or substantially all of the first SAM 750 and/or the second SAM 760, or even all of the first SAM 750 and/or the second SAM 760, can be discrete from, or joined to, or attached to, or embedded in, or integral with the first side panel.

In embodiments in which one or more portions of the anchoring subsystem 770 are integral with the first side panel, the first side panel can be considered to have a first portion, which includes the integral portions of the anchoring subsystem 770, and a second portion outside of the first portion. For example, if all of the first SAM 750 and all of the second SAM 760 were integral with the first side panel, then the first portion would include the first SAM pathway 751 and the second SAM pathway 761, while the second portion would include the three sections of the first side panel that are outside of the first SAM pathway 751 and the second SAM pathway 761. In such embodiments, this first portion and second portion can be configured in various ways, as described in the connection with the embodiment of FIG. 1C.

In some embodiments, the disposable wearable absorbent article 710 can be configured such that one or more loads in the article can cause tension in the anchoring subsystem 770 before the load can cause tension in a portion of the first side panel that is outside of the anchoring subsystem 770. In various embodiments, the disposable wearable absorbent article 710 can be configured such that one or more loads in the article can cause greater tension in the anchoring subsystem 770 than in a portion of the first side panel that is outside of the anchoring subsystem 770.

In addition to the elements previously described, the embodiment of FIG. 7C includes tension lines 775. The tension lines 775 illustrate how the first SAM 750 and the second SAM 760 can balance collected loads with obtained holding forces, so that the anchoring subsystem 770 can at least assist in holding the disposable wearable absorbent article 710 in place on a wearer. For example, the first SAM 750 can collect loads at the second end 759 and/or along the first SAM pathway 751. Also as an example, the second SAM 760 can collect loads at the third end 763 and/or along the second SAM pathway 761. In a further example, the first SAM 750 can obtain holding forces at the first end 753 and/or along the first SAM pathway 751 as the first SAM 750 experiences anchoring from direct or indirect contact with a wearer's body underneath the first SAM pathway 751. In still a further example, the second SAM 760 can obtain holding forces at the fourth end 769 and/or along the second SAM pathway 761 as the second SAM 750 experiences anchoring. These loads and forces can be received through various parts of the disposable wearable absorbent article 710, such as the chassis 720 and/or the first side panel.

The anchoring subsystem 770 is configured to indirectly anchor the absorbent core 725 to a wearer, in that, while the first SAM 750 and the second SAM 760 are not directly connected to the absorbent core 725, and the first SAM pathway 751 and the second SAM pathway 761 are each disposed outside of the absorbent core area 726, loads from the absorbent core 725 can be transmitted through various parts of the disposable wearable absorbent article 710 to the first SAM 750 and/or the second SAM 760, which can balance collected loads with obtained holding forces, so that the anchoring subsystem 770 can at least assist in holding the disposable wearable absorbent article 710 in place on a wearer. As a result, the disposable wearable absorbent article 710 can feel comfortable, look attractive, and perform well as the article tends to stay in place on a wearer and not leak.

Figure 8A:
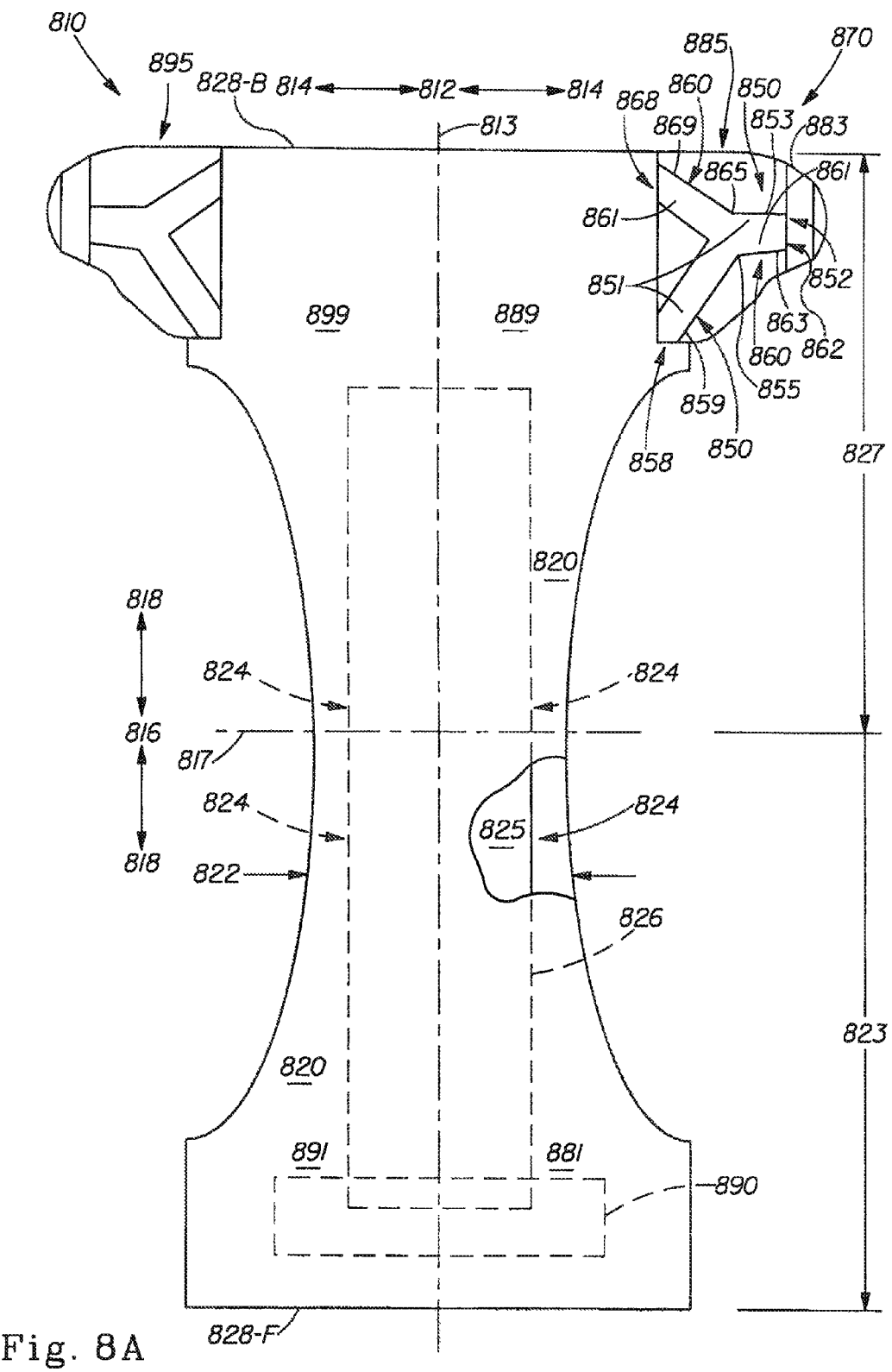
FIG. 8A illustrates a plan view of an inside of a fastenable disposable wearable absorbent article, including an anchoring subsystem with partially coextensive and partially coterminous side anchoring members, and side ears, each with one fastener, according to embodiments of the present disclosure.

FIG. 8A illustrates a plan view of an inside of a fastenable disposable wearable absorbent article 810, including an anchoring subsystem 870 with partially coextensive and partially coterminous side anchoring members, 850, 860, and side ears, 885, 895, each with one fastener, according to embodiments of the present disclosure. The disposable wearable absorbent article 810 includes a lateral centerline 817 and a longitudinal centerline 813, which provide lines of reference for referring to laterally inboard 812, laterally outboard 814, longitudinally inboard 816, and longitudinally outboard 818 relative locations of the disposable wearable absorbent article 810.

The disposable wearable absorbent article 810 also includes a chassis 820, a narrowest portion 822 of the chassis 820, a front 823, an absorbent core 825 with longitudinal edges 824, an absorbent core area 826, a back 827, a front waist edge 828-F, and a back waist edge 828-B. A portion of the chassis 820 is illustrated as cut away in order to show the absorbent core 825 and the longitudinal edges 824 more clearly. In some embodiments, the front 823 and the back 827 can be considered first and second halves of the disposable wearable absorbent article 810, although the halves may not be equal. A front portion of a first side 881 is disposed in the front 823. A back portion of the first side 889 is disposed in the back 827.

The disposable wearable absorbent article 810 has a first side ear 885 connected to the back portion of the first side 889. The first side ear 885 includes a fastener 883 and the anchoring subsystem 870. The anchoring subsystem 870 includes a first SAM 850 and a second SAM 860. The first SAM 850 is disposed along a first SAM pathway 851, and includes a first end 853 disposed at a first location 852, a second end 859 disposed at a second location 858, and a first middle 855 between the first end 853 and the second end 859. The second SAM 860 is disposed along a second SAM pathway 861, and includes a third end 863 disposed at a third location 862, a fourth end 869 disposed at a fourth location 868, and a second middle 865 between the third end 863 and the fourth end 869.

A portion of the first SAM pathway 851 from about the first middle 855 to the second end 859 is distinct from a portion of the second SAM pathway 861 from about the second middle 865 to the fourth end 869. However, a portion of the first SAM pathway 851 from the first end 853 to about the first middle 855 shares a common section of pathway with a portion of the second SAM pathway 861 from the third end 863 to about the second middle 865. As a result, a portion of the first SAM pathway 851 is coextensive with a portion of the second SAM pathway 861. In various embodiments, part or all of the first SAM pathway 851 and/or the second SAM pathway 861 can be configured as a geodesic, so that the anchoring subsystem 870 can provide geodesic anchoring.

The second end 859 and the fourth end 869 are both disposed outside of the absorbent core area 826, in the back portion of the first side 889, laterally outboard from the longitudinal edge 824 of the absorbent core 825, laterally outboard from the narrowest portion 822 of the chassis 820, and within the first side ear 885, proximate to a laterally inboard edge of the first side ear 885. In some embodiments, one or both of the second and fourth ends 859, 869 can be disposed at various locations, including locations outside of the first side ear 885, and/or within the back portion of the first side 889, and/or laterally inboard to the narrowest portion 822 of the chassis 820, and/or laterally inboard to the longitudinal edges 824 of the absorbent core 825, and/or within the absorbent core area 826. The fourth location 868 is longitudinally outboard from the second location 858. The first end 853 and the third end 863 are both disposed within the first side ear 885. The dispositions of the first and third ends 853, 863 are further described in connection with the embodiment of FIG. 8C.

Figure 8B:
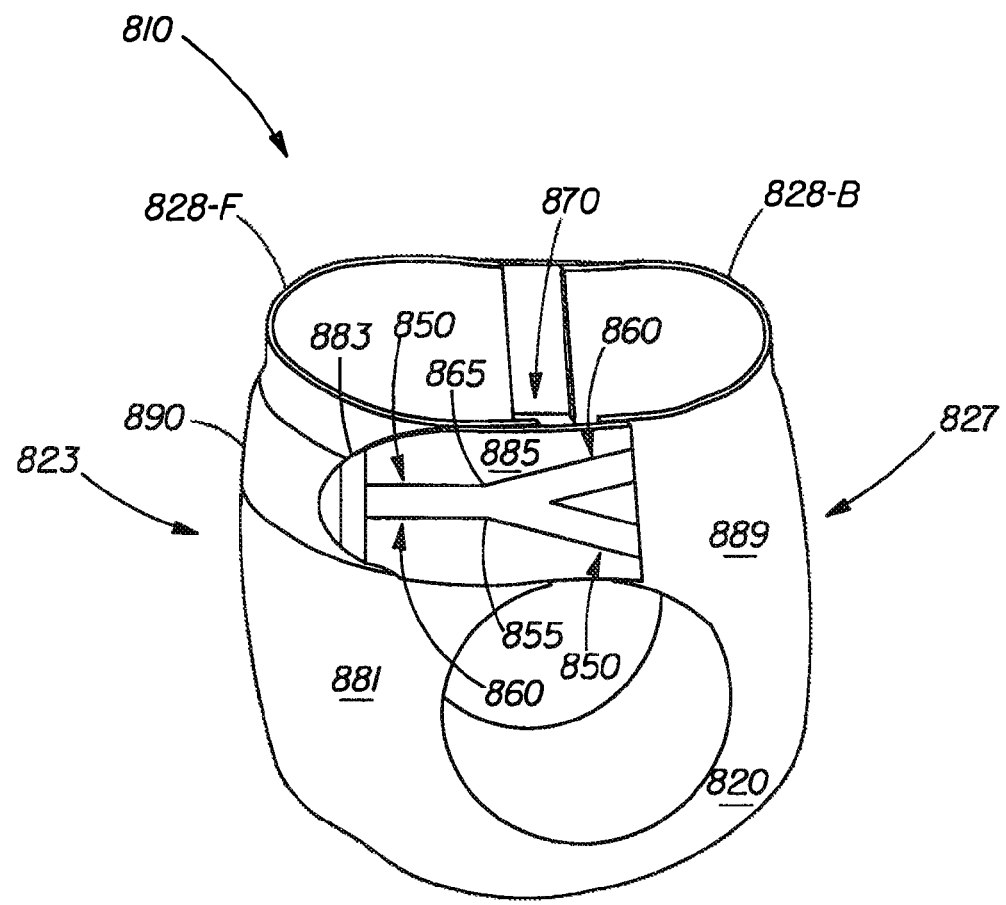
FIG. 8B illustrates a perspective view of an outside of the disposable wearable absorbent article of the embodiment of FIG. 8A, formed for wearing.
Figure 8C:
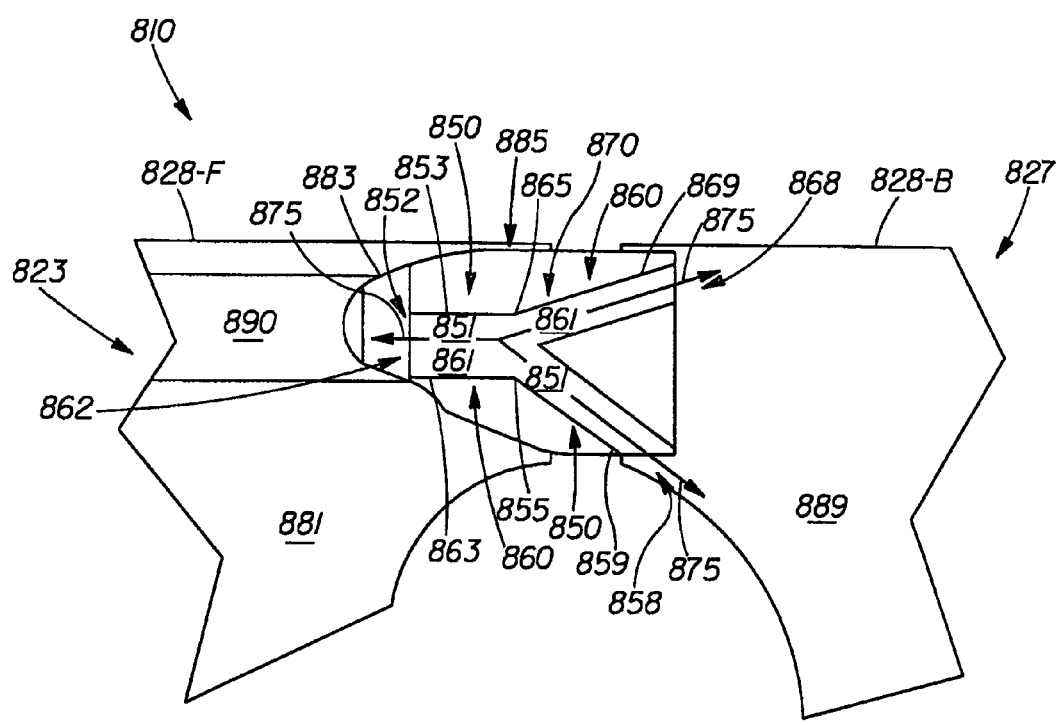
FIG. 8C illustrates an enlarged view of a portion of a side of the disposable wearable absorbent article of the embodiment of FIG. 8B.

The anchoring subsystem 870 is not directly connected to the absorbent core 825, and is outside of the absorbent core area 826, so the anchoring subsystem 870 is separate from the absorbent core 825. The anchoring subsystem 870 is considered a subsystem because neither the first SAM 850 nor the second SAM 860 will substantially or completely encircle the lower torso of a wearer, and because the anchoring subsystem 870 is contained within a particular, defined portion of the disposable wearable absorbent article 810. In the embodiment of FIGS. 8A-8C, the anchoring subsystem 870 is contained within the first side of the disposable wearable absorbent article 870, so the anchoring subsystem 870 is considered a side anchoring subsystem. The disposable wearable absorbent article 810 can also include an outer cover, which can, in various embodiments, be separate from the anchoring subsystem 870. In some embodiments, part or all of such an outer cover can be stretchable, elastic, or extensible.

The disposable wearable absorbent article 810 also includes a front portion of a second side 891, a second side ear 895 connected to a back portion of the second side 899. The second side ear 895 is configured similar to the first side ear 885, however, in various embodiments, the second side ear 895 can, alternatively, be configured differently. The disposable wearable absorbent article 810 further includes a fastening area 890.

FIG. 8B illustrates a perspective view of an outside of the disposable wearable absorbent article 810 of the embodiment of FIG. 8A, formed for wearing. In the embodiment of FIG. 8B, the fastener 883 is fastened to the fastening area 890.

FIG. 8C illustrates an enlarged view of a portion of a side of the disposable wearable absorbent article 810 of the embodiment of FIG. 8B. The fastener 883 is fastened to the fastening area 890, so that the first side ear 885 fastens the front 823 to the back 827. As a result, a portion of the first side ear 885 is disposed in the front 823 and a portion of the first side ear 885 is disposed in the back 827. In this fastened configuration, the first end 853 and the third end 863 are both disposed outside of the absorbent core area 826, in the front portion of the first side 881, laterally outboard from the longitudinal edge 824 of the absorbent core 825, laterally outboard from the narrowest portion 822 of the chassis 820, and within the first side ear 885. The first end 853 and the third end 863 are disposed proximate to an edge of the fastener 883. In some embodiments, the fastener 883 can be fastened so that one or both of the first and third ends 853, 863 can be disposed at various locations, including locations laterally inboard to the narrowest portion 822 of the chassis 820, and/or laterally inboard to the longitudinal edges 824 of the absorbent core 825, and/or within the front portion of the first side 881, and/or within the absorbent core area 826. The third location 862 at least partially overlaps with the first location 852, so that the first SAM pathway 851 and the second SAM pathway 861 are coterminous at their laterally outboard ends. In some embodiments, the third location 862 can substantially or completely coincide with the first location 852.

In various embodiments of the present disclosure, one or more parts of or at least a portion of the anchoring subsystem 870 can be structurally associated with the first side ear 885. In some embodiments, at least a portion of the anchoring subsystem 870, or substantially all of the anchoring subsystem 870, or even all of the anchoring subsystem 870, can be discrete from, or joined to, attached to, or embedded in, or integral with the first side ear 885. In various embodiments, at least a portion of the first SAM 850 and/or the second SAM 860, or substantially all of the first SAM 850 and/or the second SAM 860, or even all of the first SAM 850 and/or the second SAM 860, can be discrete from, or joined to, or attached to, or embedded in, or integral with the first side ear 885.

In embodiments in which one or more portions of the anchoring subsystem 870 are integral with the first side ear 885, the first side ear 885 can be considered to have a first portion, which includes the integral portions of the anchoring subsystem 870, and a second portion outside of the first portion. For example, if all of the first SAM 850 and all of the second SAM 860 were integral with the first side ear 885, then the first portion would include the first SAM pathway 851 and the second SAM pathway 861, while the second portion would include the three sections of the first side ear 885 that are outside of the first SAM pathway 851 and the second SAM pathway 861. In such embodiments, this first portion and second portion can be configured in various ways, as described in the connection with the embodiment of FIG. 1C.

In some embodiments, the disposable wearable absorbent article 810 can be configured such that one or more loads in the article can cause tension in the anchoring subsystem 870 before the load can cause tension in a portion of the first side ear 885 that is outside of the anchoring subsystem 870. In various embodiments, the disposable wearable absorbent article 810 can be configured such that one or more loads in the article can cause greater tension in the anchoring subsystem 870 than in a portion of the first side ear 885 that is outside of the anchoring subsystem 870.

In addition to the elements previously described, the embodiment of FIG. 8C includes tension lines 875. The tension lines 875 illustrate how the first SAM 850 and the second SAM 860 can balance collected loads with obtained holding forces, so that the anchoring subsystem 870 can at least assist in holding the disposable wearable absorbent article 810 in place on a wearer. For example, the first SAM 850 can collect loads at the second end 859 and/or along the first SAM pathway 851, with loads received through various parts of the disposable wearable absorbent article 810, such as the chassis 820 and/or the first side ear 885. Also as an example, the second SAM 860 can collect loads at the third end 863 and/or along the second SAM pathway 861, with loads received through various parts of the disposable wearable absorbent article 810, such as the fastener 883 and/or the first side ear 885.

In a further example, the first SAM 850 can obtain holding forces at the first end 853 with forces received through various parts of the disposable wearable absorbent article 810, such as the fastener 883 and/or the first side ear 885. In a still further example, the first SAM 850 can also obtain holding forces along the first SAM pathway 851 as the first SAM 850 experiences anchoring from direct or indirect contact with a wearer's body underneath the first SAM pathway 851. As a similar example, the second SAM 860 can obtain holding forces at the fourth end 869 with forces received through various parts of the disposable wearable absorbent article 810, such as the chassis 820 and/or the first side ear 885. As another similar example, the second SAM 860 can obtain holding forces along the second SAM pathway 861 as the second SAM 850 experiences anchoring.

The anchoring subsystem 870 is configured to indirectly anchor the absorbent core 825 to a wearer, in that, while the first SAM 850 and the second SAM 860 are not directly connected to the absorbent core 825, and the first SAM pathway 851 and the second SAM pathway 861 are each disposed outside of the absorbent core area 826, loads from the absorbent core 825 can be transmitted through various parts of the disposable wearable absorbent article 810 to the first SAM 850 and/or the second SAM 860, which can balance collected loads with obtained holding forces, so that the anchoring subsystem 870 can at least assist in holding the disposable wearable absorbent article 810 in place on a wearer. As a result, the disposable wearable absorbent article 810 can feel comfortable, look attractive, and perform well as the article tends to stay in place on a wearer and not leak.

Figure 9A:
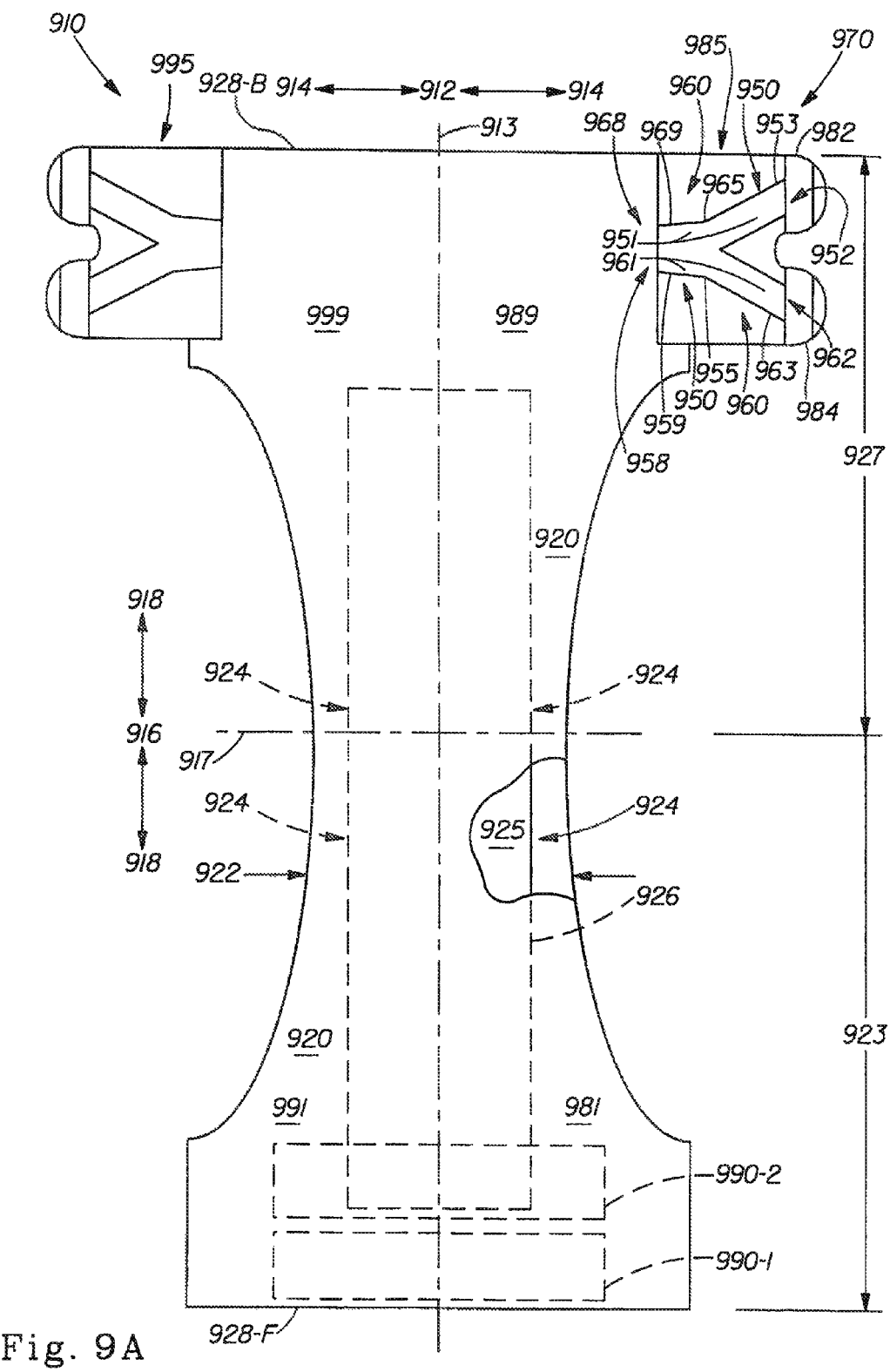
FIG. 9A illustrates a plan view of an inside of a fastenable disposable wearable absorbent article, including an anchoring subsystem with partially coextensive and partially coterminous side anchoring members, and side ears, each with two fasteners, according to embodiments of the present disclosure.

FIG. 9A illustrates a plan view of an inside of a fastenable disposable wearable absorbent article 910, including an anchoring subsystem 970 with partially coextensive and partially coterminous side anchoring members, 950, 960, and side ears, 985, 995, each with two fasteners, according to embodiments of the present disclosure. The disposable wearable absorbent article 910 includes a lateral centerline 917 and a longitudinal centerline 913, which provide lines of reference for referring to laterally inboard 912, laterally outboard 914, longitudinally inboard 916, and longitudinally outboard 918 relative locations of the disposable wearable absorbent article 910.

The disposable wearable absorbent article 910 also includes a chassis 920, a narrowest portion 922 of the chassis 920, a front 923, an absorbent core 925 with longitudinal edges 924, an absorbent core area 926, a back 927, a front waist edge 928-F, and a back waist edge 928-B. A portion of the chassis 920 is illustrated as cut away in order to show the absorbent core 925 and the longitudinal edges 924 more clearly. In some embodiments, the front 923 and the back 927 can be considered first and second halves of the disposable wearable absorbent article 910, although the halves may not be equal. A front portion of a first side 981 is disposed in the front 923. A back portion of the first side 989 is disposed in the back 927.

The disposable wearable absorbent article 910 has a first side ear 985 connected to the back portion of the first side 989. The first side ear 985 includes a first fastener 982, a second fastener 984, and the anchoring subsystem 970. However, in various embodiments, the first side ear 985 can, alternatively, be configured to have a single fastener. The anchoring subsystem 970 includes a first SAM 950 and a second SAM 960. The first SAM 950 is disposed along a first SAM pathway 951, and includes a first end 953 disposed at a first location 952, a second end 959 disposed at a second location 958, and a first middle 955 between the first end 953 and the second end 959. The second SAM 960 is disposed along a second SAM pathway 961, and includes a third end 963 disposed at a third location 962, a fourth end 969 disposed at a fourth location 968, and a second middle 965 between the third end 963 and the fourth end 969.

A portion of the first SAM pathway 951 from the first end 953 to about the first middle 955 is distinct from a portion of the second SAM pathway 961 from the third end 963 to about the second middle 965. However, a portion of the first SAM pathway 951 from about the first middle 955 to the second end 959 shares a common section of pathway with a portion of the second SAM pathway 961 from about the second middle 965 to the fourth end 969. As a result, a portion of the first SAM pathway 951 is coextensive with a portion of the second SAM pathway 961. In various embodiments, part or all of the first SAM pathway 951 and/or the second SAM pathway 961 can be configured as a geodesic, so that the anchoring subsystem 970 can provide geodesic anchoring.

The second end 959 and the fourth end 969 are both disposed outside of the absorbent core area 926, in the back portion of the first side 989, laterally outboard from the longitudinal edge 924 of the absorbent core 925, laterally outboard from the narrowest portion 922 of the chassis 920, and within the first side ear 985, proximate to a laterally inboard edge of the first side ear 985. In some embodiments, one or both of the second and fourth ends 959, 969 can be disposed at various locations, including locations outside of the first side ear 985, and/or within the back portion of the first side 989, and/or laterally inboard to the narrowest portion 922 of the chassis 920, and/or laterally inboard to the longitudinal edges 924 of the absorbent core 925, and/or within the absorbent core area 926. The fourth location 968 at least partially overlaps with the second location 958, so that the first SAM pathway 951 and the second SAM pathway 961 are coterminous at their laterally inboard ends. In some embodiments, the fourth location 968 can substantially or completely coincide with the second location 958. The first end 953 and the third end 963 are both disposed within the first side ear 985. The dispositions of the first and third ends 953, 963 are further described in connection with the embodiment of FIG. 9C.

Figure 9B:
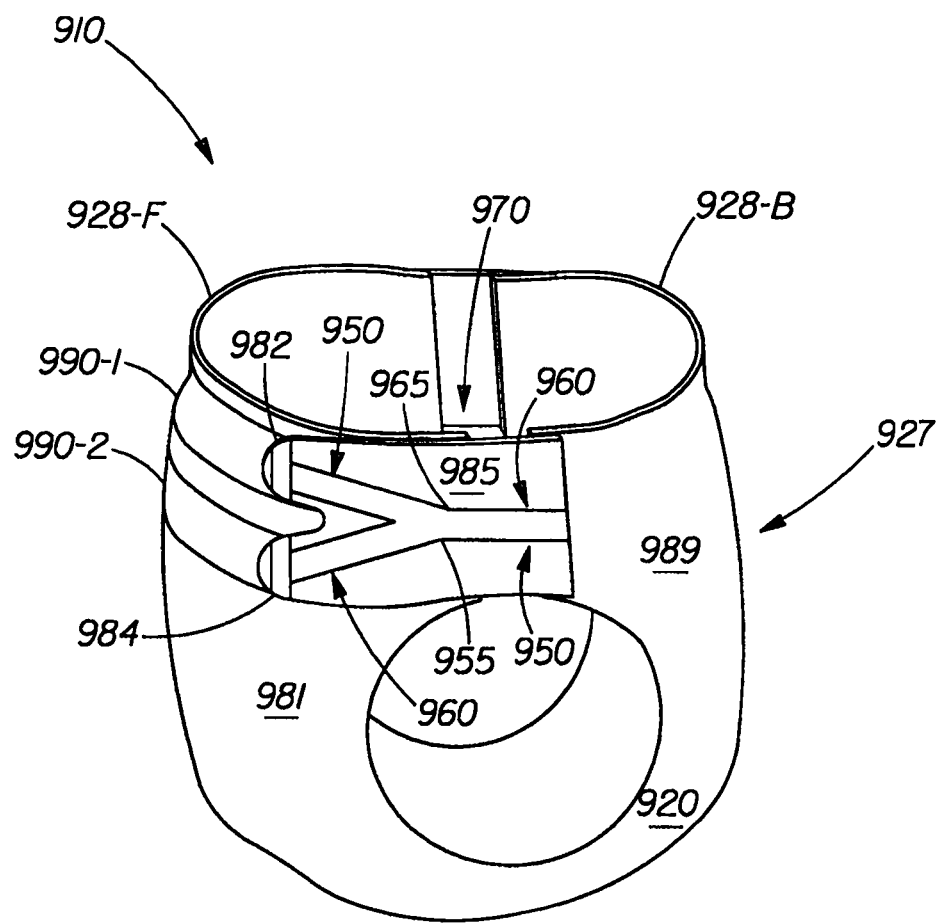
FIG. 9B illustrates a perspective view of an outside of the disposable wearable absorbent article of the embodiment of FIG. 9A, formed for wearing.
Figure 9C:
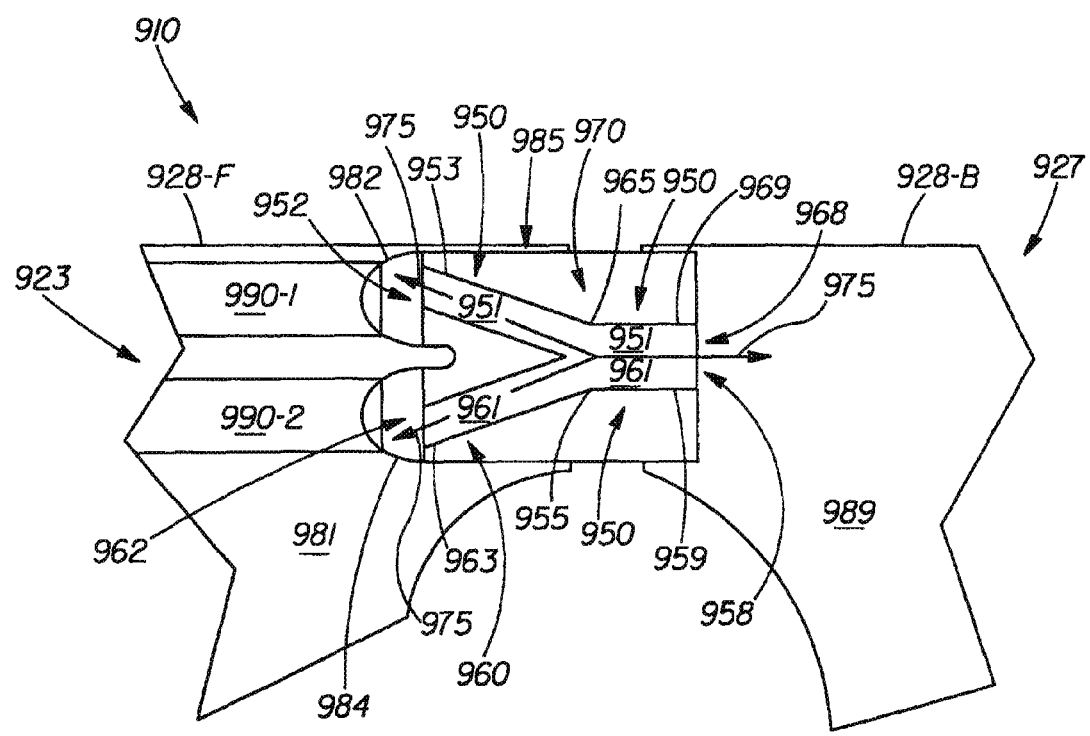
FIG. 9C illustrates an enlarged view of a portion of a side of the disposable wearable absorbent article of the embodiment of FIG. 9B.

The anchoring subsystem 970 is not directly connected to the absorbent core 925, and is outside of the absorbent core area 926, so the anchoring subsystem 970 is separate from the absorbent core 925. The anchoring subsystem 970 is considered a subsystem because neither the first SAM 950 nor the second SAM 960 will substantially or completely encircle the lower torso of a wearer, and because the anchoring subsystem 970 is contained within a particular, defined portion of the disposable wearable absorbent article 910. In the embodiment of FIGS. 9A-9C, the anchoring subsystem 970 is contained within the first side of the disposable wearable absorbent article 970, so the anchoring subsystem 970 is considered a side anchoring subsystem. The disposable wearable absorbent article 910 can also include an outer cover, which can, in various embodiments, be separate from the anchoring subsystem 970. In some embodiments, part or all of such an outer cover can be stretchable, elastic, or extensible.

The disposable wearable absorbent article 910 also includes a front portion of a second side 991, a second side ear 995 connected to a back portion of the second side 999. The second side ear 995 is configured similar to the first side ear 985, however, in various embodiments, the second side ear 995 can, alternatively, be configured differently. The disposable wearable absorbent article 910 further includes a first fastening area 990-1 and a second fastening area 990-2.

FIG. 9B illustrates a perspective view of an outside of the disposable wearable absorbent article 910 of the embodiment of FIG. 9A, formed for wearing. In the embodiment of FIG. 9B, the first fastener 982 is fastened to the first fastening area 990-1 and the second fastener 984 is fastened to the second fastening area 990-2.

FIG. 9C illustrates an enlarged view of a portion of a side of the disposable wearable absorbent article 910 of the embodiment of FIG. 9B. The first fastener 982 is fastened to the first fastening area 990-1 and the second fastener 984 is fastened to the second fastening area 990-2, so that the first side ear 985 fastens the front 923 to the back 927. As a result, a portion of the first side ear 985 is disposed in the front 923 and a portion of the first side ear 985 is disposed in the back 927. In this fastened configuration, the first end 953 and the third end 963 are both disposed outside of the absorbent core area 926, in the front portion of the first side 981, laterally outboard from the longitudinal edge 924 of the absorbent core 925, laterally outboard from the narrowest portion 922 of the chassis 920, and within the first side ear 985. In some embodiments, the fastener 983 can be fastened so that one or both of the first and third ends 953, 963 can be disposed at various locations, including locations laterally inboard to the narrowest portion 922 of the chassis 920, and/or laterally inboard to the longitudinal edges 924 of the absorbent core 925, and/or within the front portion of the first side 981, and/or within the absorbent core area 926. The third location 962 is longitudinally inboard to the first location 952.

In various embodiments of the present disclosure, one or more parts of or at least a portion of the anchoring subsystem 970 can be structurally associated with the first side ear 985. In some embodiments, at least a portion of the anchoring subsystem 970, or substantially all of the anchoring subsystem 970, or even all of the anchoring subsystem 970, can be discrete from, or joined to, attached to, or embedded in, or integral with the first side ear 985. The first end 953 is disposed proximate to an edge of the first fastener 982 and the third end 963 is disposed proximate to an edge of the second fastener 984. In various embodiments, at least a portion of the first SAM 950 and/or the second SAM 960, or substantially all of the first SAM 950 and/or the second SAM 960, or even all of the first SAM 950 and/or the second SAM 960, can be discrete from, or joined to, or attached to, or embedded in, or integral with the first side ear 985.

In embodiments in which one or more portions of the anchoring subsystem 970 are integral with the first side ear 985, the first side ear 985 can be considered to have a first portion, which includes the integral portions of the anchoring subsystem 970, and a second portion outside of the first portion. For example, if all of the first SAM 950 and all of the second SAM 960 were integral with the first side ear 985, then the first portion would include the first SAM pathway 951 and the second SAM pathway 961, while the second portion would include the three sections of the first side ear 985 that are outside of the first SAM pathway 951 and the second SAM pathway 961. In such embodiments, this first portion and second portion can be configured in various ways, as described in the connection with the embodiment of FIG. 1C.

In some embodiments, the disposable wearable absorbent article 910 can be configured such that one or more loads in the article can cause tension in the anchoring subsystem 970 before the load can cause tension in a portion of the first side ear 985 that is outside of the anchoring subsystem 970. In various embodiments, the disposable wearable absorbent article 910 can be configured such that one or more loads in the article can cause greater tension in the anchoring subsystem 970 than in a portion of the first side ear 985 that is outside of the anchoring subsystem 970.

In addition to the elements previously described, the embodiment of FIG. 9C includes tension lines 975. The tension lines 975 illustrate how the first SAM 950 and the second SAM 960 can balance collected loads with obtained holding forces, so that the anchoring subsystem 970 can at least assist in holding the disposable wearable absorbent article 910 in place on a wearer. For example, the first SAM 950 can collect loads at the second end 959 and/or along the first SAM pathway 951, with loads received through various parts of the disposable wearable absorbent article 910, such as the chassis 920 and/or the first side ear 985. Also as an example, the second SAM 960 can collect loads at the third end 963 and/or along the second SAM pathway 961, with loads received through various parts of the disposable wearable absorbent article 910, such as the second fastener 984 and/or the first side ear 985.

In a further example, the first SAM 950 can obtain holding forces at the first end 953 with forces received through various parts of the disposable wearable absorbent article 910, such as the first fastener 982 and/or the first side ear 985. In a still further example, the first SAM 950 can also obtain holding forces along the first SAM pathway 951 as the first SAM 950 experiences anchoring from direct or indirect contact with a wearer's body underneath the first SAM pathway 951. As a similar example, the second SAM 960 can obtain holding forces at the fourth end 969 with forces received through various parts of the disposable wearable absorbent article 910, such as the chassis 920 and/or the first side ear 985. As another similar example, the second SAM 960 can obtain holding forces along the second SAM pathway 961 as the second SAM 950 experiences anchoring.

The anchoring subsystem 970 is configured to indirectly anchor the absorbent core 925 to a wearer, in that, while the first SAM 950 and the second SAM 960 are not directly connected to the absorbent core 925, and the first SAM pathway 951 and the second SAM pathway 961 are each disposed outside of the absorbent core area 926, loads from the absorbent core 925 can be transmitted through various parts of the disposable wearable absorbent article 910 to the first SAM 950 and/or the second SAM 960, which can balance collected loads with obtained holding forces, so that the anchoring subsystem 970 can at least assist in holding the disposable wearable absorbent article 910 in place on a wearer. As a result, the disposable wearable absorbent article 910 can feel comfortable, look attractive, and perform well as the article tends to stay in place on a wearer and not leak.

FIG. 10A illustrates a first embodiment of incremental stretching for use in an anchoring subsystem in a side of the disposable wearable absorbent article, according to embodiments of the present disclosure. The incremental stretching of FIG. 10A includes lines 1096 (for clarity, not all lines are labeled) formed in the material of the side by mechanical teeth. In a first portion 1091, the side is incrementally stretched with a first particular number of teeth per a unit of distance. In a second portion 1092, the side is incrementally stretched with a second particular number of teeth per the unit of distance. In the embodiment of FIG. 10A, the first particular number of teeth is five ninths of the second particular number of teeth. As a result, the first portion 1091 is incrementally stretched to a lesser degree, and substantially all of the second portion 1092 is incrementally stretched to a greater degree, as described in connection with the embodiments of FIG. 1C.

FIG. 10B illustrates a second embodiment of incremental stretching for use in an anchoring subsystem in a side of the disposable wearable absorbent article, according to embodiments of the present disclosure. The incremental stretching of FIG. 10B includes lines 1096 (for clarity, not all lines are labeled) formed in the material of the side by mechanical teeth. In a first portion 1093, the side is incrementally stretched with a first particular number of teeth per a unit of distance. In a second portion 1094, the side is incrementally stretched with a second particular number of teeth per the unit of distance. In the embodiment of FIG. 10B, the first particular number of teeth is two thirds of the second particular number of teeth. As a result, the first portion 1093 is incrementally stretched to a lesser degree, and substantially all of the second portion 1094 is incrementally stretched to a greater degree, as described in connection with the embodiments of FIG. 1C.

FIG. 10C illustrates a third embodiment of incremental stretching for use in an anchoring subsystem in a side of the disposable wearable absorbent article, according to embodiments of the present disclosure. The incremental stretching of FIG. 10C includes lines 1096 (for clarity, not all lines are labeled) formed in the material of the side by mechanical teeth. In a first portion 1097, the side is incrementally stretched with a first particular number of teeth per a unit of distance. In a second portion 1098, the side is incrementally stretched with a second particular number of teeth per the unit of distance. In the embodiment of FIG. 10C, the first particular number of teeth is two thirds of the second particular number of teeth. As a result, the first portion 1097 is incrementally stretched to a lesser degree, and substantially all of the second portion 1098 is incrementally stretched to a greater degree, as described in connection with the embodiments of FIG. 1C.

Figure 11A:
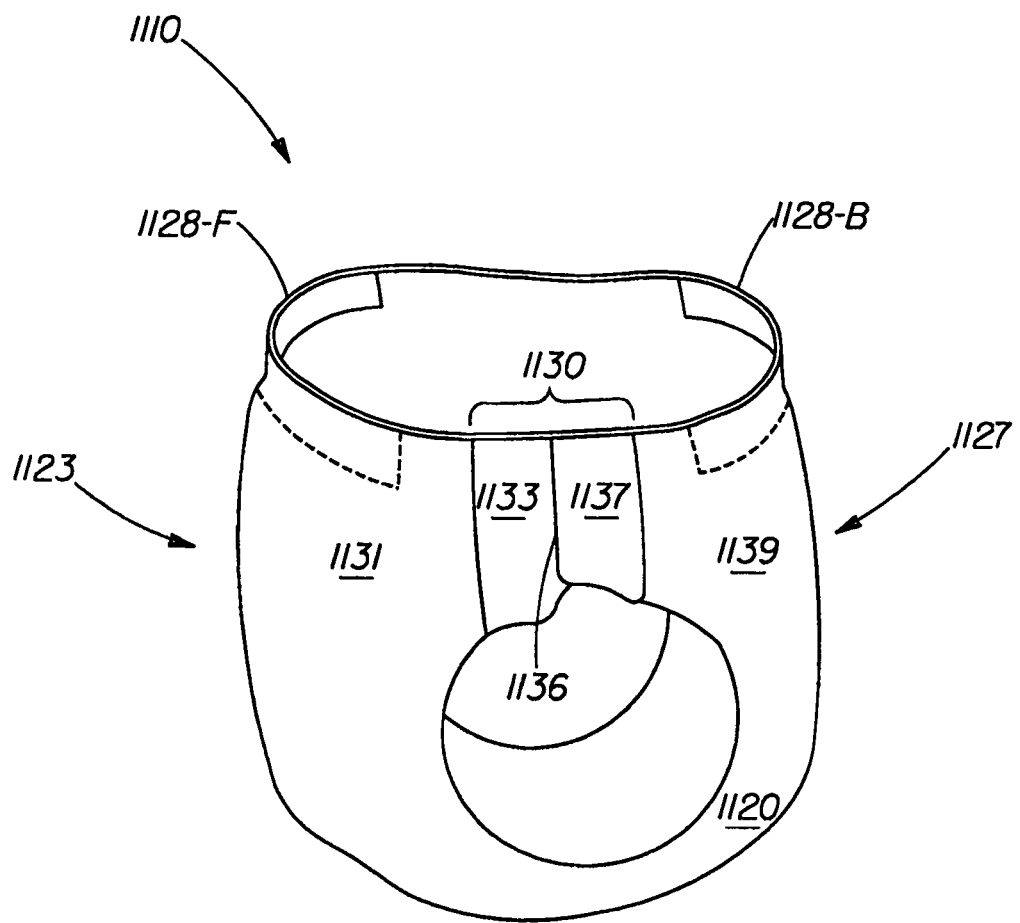
FIG. 11A illustrates a perspective view of an outside of a pant-type disposable wearable absorbent article, formed for wearing, according to embodiments of the present disclosure.

FIG. 11A illustrates a perspective view of an outside of a pant-type disposable wearable absorbent article 1110, formed for wearing. The disposable wearable absorbent article 1110 includes a chassis 1120, a front 1123, a back 1127, a front waist edge 1128-F, and a back waist edge 1128-B. The disposable wearable absorbent article 1110 also includes a first side and a second side. A front portion of the first side 1131 is disposed in the front 1123. A back portion of the first side 1139 is disposed in the back 1127. The disposable wearable absorbent article 1110 has a first side panel 1130, which includes a front portion of the first side panel 1133 and a back portion of the first side panel 1137. A connection 1136 connects the front portion of the first side panel 1133 with the back portion of the first side panel 1137 to form the first side. In the embodiment of FIG. 11A, the connection 1136 is a durable connection. The second side can include a second side panel, configured similar to the first side panel. However, in various embodiments, the second side panel can, alternatively, be configured differently.

The first side panel 1130 also includes an anchoring subsystem with two SAMs. In the embodiment of FIG. 11A, the SAMs are not readily visibly apparent, and thus are not shown in FIG. 11A. However, the presence of one or more anchoring subsystem elements, such as SAMs, can be detected by using a modulus mapping method. This method can also be used to measure particular modulus of elasticity values for one or more anchoring subsystem elements, such as SAMs. The modulus mapping method is described below, and in connection with the embodiments of FIGS. 11B-11F.

A first step in the modulus mapping method is to determine an area of interest in a disposable wearable absorbent article. The area of interest is a continuous portion of the article, which completely contains the one or more anchoring subsystem elements to be tested. The area of interest also includes one or more portions of the article surrounding the anchoring subsystem element(s). In other words, the area of interest is not limited to the anchoring subsystem elements, but includes the one or more portions of the article that form the physical context on all sides of each of the element(s). The area of interest should contain enough of this physical context to be tested with the modulus mapping method on all sides of each of the anchoring system element(s). In this way, the presence of each of the anchoring subsystem element(s) can be detected within their physical context, in the area of interest.

The presence of an anchoring subsystem element may be known from knowledge of the article. In the embodiment of FIG. 11A, since the first side panel 1130 is known to contain an anchoring subsystem with two SAMs, the first side panel 1130 is the area of interest. Alternatively, the presence of an anchoring subsystem element may be apparent upon visual inspection of the article or may be suspected based on other facts. Where the presence of an anchoring subsystem element is uncertain, the area of interest can be determined by testing various portions of one or more samples of a disposable wearable absorbent article with the steps of the modulus mapping method, as will be understood by one of ordinary skill in the art.

Figure 11B:
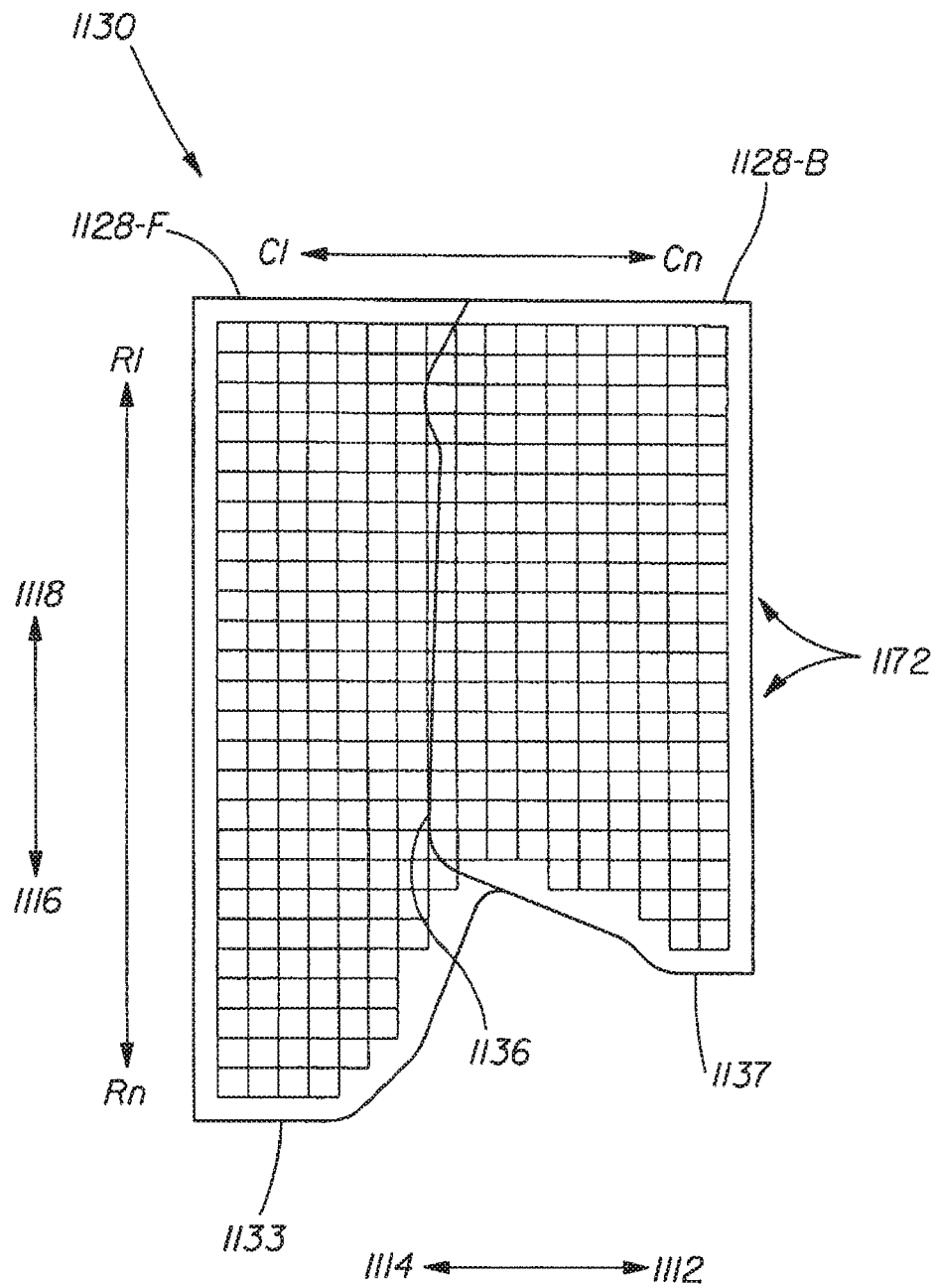
FIG. 11B illustrates an enlarged view of the first side panel of the disposable wearable absorbent article of the embodiment of FIG. 11A, cut from the article and marked with a map for testing with a modulus mapping method, according to embodiments of the present disclosure.

A second step in the modulus mapping method is to cut the area of interest from the disposable wearable absorbent article. If the area of interest is a side panel of a disposable wearable absorbent article, then continuous cuts are made through the article along one or more paths between the side panel and the rest of the article. Any connections in the side panel are left fastened and/or intact, so the area of interest can be a continuous portion of the article. FIG. 11B illustrates an enlarged view of a portion of the first side panel 1130 of the disposable wearable absorbent article 1110 of the embodiment of FIG. 11A, cut from the article 1110 for testing with the modulus mapping method.

If the area of interest is a side ear of a fastenable disposable wearable absorbent article, then continuous cuts are made through the article along one or more paths between the side ear and the rest of the article. If the side ear is fastened, then it is unfastened, for complete removal from the article.

For other areas of interest, including areas that are more than or less than a side panel or a side ear, continuous cuts are made through the article, on both sides of the area, from points on a waist edge of the article, cutting on paths perpendicular to the waist edge. These cuts either continue until they reach a leg opening of the article, or turn to reach the leg opening on the shortest cutting path parallel to the waist edge. Any connections in the area of interest are left fastened and/or intact, so the area of interest can be a continuous portion of the article.

A third step in the modulus mapping method is to mark the area of interest with a map, which is a grid of squares. While the area of interest is marked, the area is laid out flat, so the surface of the area of interest is not disturbed or distorted. In general, the gridlines of the map should run parallel to and perpendicular to the lateral direction of the disposable wearable absorbent article. However, if the material of the area of interest has a primary direction of elasticity, stretchability, or extensibility, then the gridlines of the map should run parallel to and perpendicular to that primary direction of stretch. Each of the squares in the grid is 5.0 millimeters by 5.0 millimeters. The gridlines can be measured in various ways, such as by using a calibrated ruler. The gridlines can also be marked in various ways, such as by using a fine tipped marking pen. The marked map is a grid of squares with rows R1 through Rn and columns C1 through Cn. Thus, each square on the map can be uniquely referenced by row and column number (e.g. C1:R1 for the square of column 1, row 1).

FIG. 11B illustrates an enlarged view of a portion of the first side panel 1130 of the disposable wearable absorbent article 1110 of the embodiment of FIG. 11A, cut from the article 1110 and marked with a map 1172, for testing with the modulus mapping method. FIG. 11B illustrates directions of laterally inboard 1112 and laterally outboard 1114 (using the lateral directions for the back 1127 for ease of reference) as well as directions for longitudinally inboard 1116 and longitudinally outboard 118. The portion of the first side panel 1130 also includes the front waist edge 1128-F, the back waist edge 1128-B, the front portion of the first side panel 1133, the connection 1136, and the back portion of the first side panel 1137. In the embodiment of FIG. 11B, the material of the area of interest has a primary direction of stretchability in the lateral direction. Therefore, the map 1172 is marked on the side panel 1130, as described above, so that the gridlines of the map 1172 run parallel to and perpendicular to that primary direction of stretch, which is the lateral direction.

A fourth step in the modulus mapping method is to test the area of interest. The dimensions of the area of interest are measured and recorded, for use in calculating modulus of elasticity. To determine thickness of material, a 3.14 cm$^2$ round foot caliper is used, with 0.5 kPa of pressure and 10 seconds of residence time.

The testing uses a constant rate of extension tensile tester, fitted with a 5 N load cell. The tensile tester includes a computer interface, such as a MTS Alliance with TestWorks 4 software (available from MTS Systems Corp., Eden Prairie, Minn.). With regard to the test equipment described below, dimensions are given as precise values. The tensile tester is fitted with a set of 10 N Advantage™ pneumatic grips (available from MTS as part 100-032-017) and 15 millimeter wide by 8 millimeter high 10 N Advantage™ grip faces with smooth steel surface (available from MTS as part 56-163-702). Each of the grip faces is modified by mounting a hard rubber facing on the grip face. The rubber facing is a hard neoprene rubber with a Durometer rating of 70A. The rubber facing is 5.00 millimeters wide by 8.0 millimeters high by 2.0 millimeters deep. The rubber facing is centered on the base width of the grip face. When the pneumatic grips are closed, the rubber facings should be vertically and horizontally aligned.

Figure 11C:
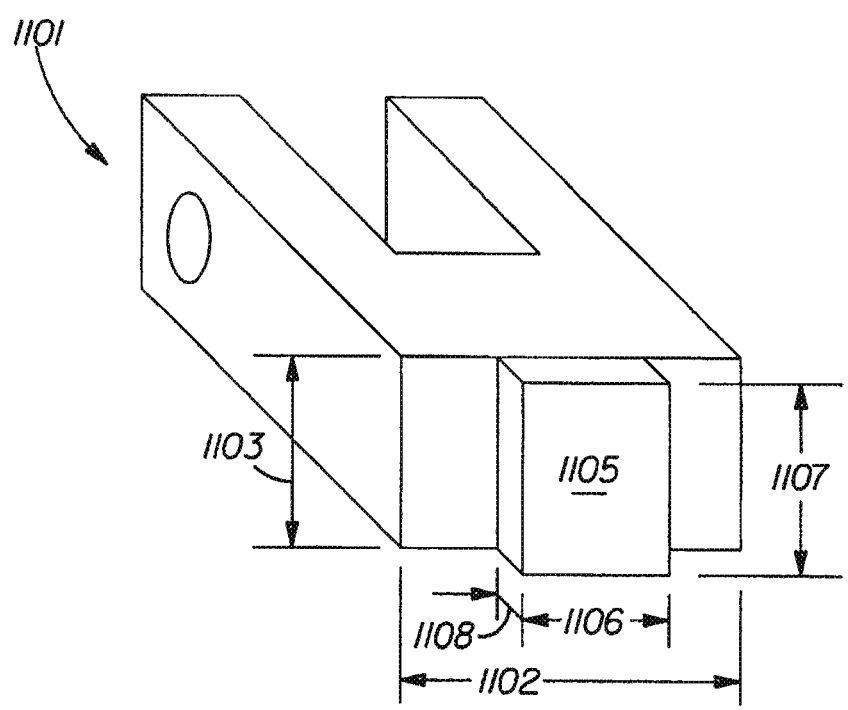
FIG. 11C illustrates a modified pneumatic grip, for use in the modulus mapping method according to embodiments of the present disclosure.

FIG. 11C illustrates a modified pneumatic grip 1101, as described above, for use in the modulus mapping method. The modified pneumatic grip 1101 includes base grip width 1102 (15 millimeters) and base grip height 1103 (8 millimeters). The modified pneumatic grip 1101 also includes a hard rubber facing 1105 with a facing width 1106 (5.00 millimeters), a facing height 1107 (8.0 millimeters), and a facing depth 1108 (2.0 millimeters).

Using this test equipment, the area of interest is tested with the modulus mapping method as follows. For clarity, in this description of testing, references to the area of interest refer to the side panel 1130 of the embodiment of FIG. 11B. The data acquisition rate of the tensile tester is set to 100 Hz and the gage length is set to 5.0 mm. The crosshead and the load cell are zeroed.

If there is no primary direction of elasticity, stretchability, or extensibility in the area of interest, then the area of interest is inserted and aligned as described below. The area of interest is inserted into the upper pneumatic grip at the square C1:R1 and oriented to pull the side panel 1130 in the lateral direction of the disposable wearable absorbent article. The upper grip is aligned outside of square C1:R1, along the laterally outboard gridline of the square C1:R1, and closed. The area of interest is also inserted into the lower pneumatic grip, aligned outside of square C1:R1, along the laterally inboard gridline of the square, and closed.

If there is a primary direction of elasticity, stretchability, or extensibility in the area of interest, then the area of interest is inserted and aligned as described below. The area of interest is inserted into the upper pneumatic grip at the square C1:R1 and oriented to pull the side panel 1130 in the primary direction of stretch. The upper grip is aligned outside of square C1:R1, along a first gridline of the square that is perpendicular to the primary direction of stretch, and closed. The area of interest is also inserted into the lower pneumatic grip, aligned outside of square C1:R1, along a second gridline of the square that is opposite from the first gridline and also perpendicular to the primary direction of stretch, and closed.

Figure 11D:
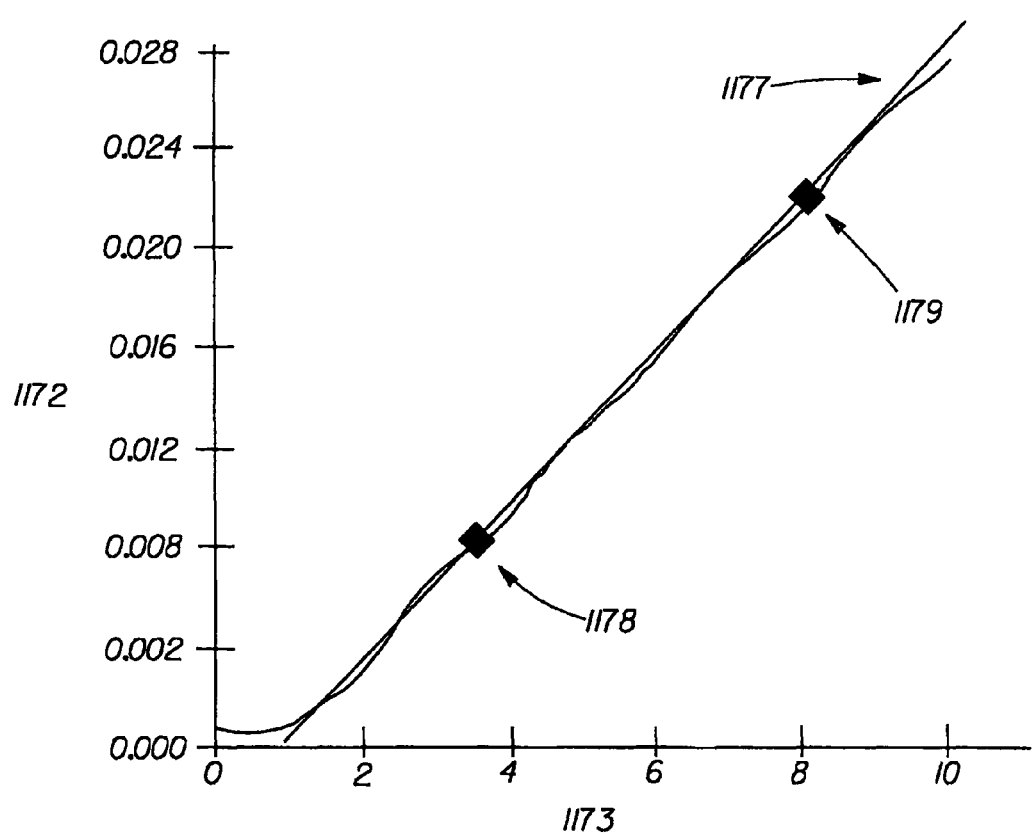
FIG. 11D illustrates an exemplary graph of the modulus of elasticity of a square of the map of the embodiment of FIG. 11B, according to embodiments of the present disclosure.

The area of interest should be under enough tension to eliminate any slack, but with less than 0.02 N of force on the load cell. The tensile tester is started and data is collected. The grips are moved apart at a constant rate of 25 millimeters per minute to 10% strain. The modulus of elasticity of the square is calculated as a directional modulus of elasticity, since the area of interest is pulled in a particular direction, e.g. the lateral direction or the primary direction of stretch. The directional modulus of elasticity of the square is calculated as the slope of the linear region of the resulting stress versus strain curve, using a slope segment length of 50% to determine the modulus line. As an example, FIG. 11D illustrates an exemplary graph of the modulus of elasticity of a square of the map 1172, with stress 1172 in mega Pascals versus strain 1173 as a percentage, and a modulus line 1177 using a slope segment length of 50% from point 1178 to point 1179. The directional modulus of elasticity is determined to ±0.01 mega Pascals and recorded. This testing procedure is repeated for each square on the map, testing the first column (from C1:R1 to C1:Rn) followed by each successive column (from C2 to Cn). FIG. 11E illustrates an exemplary chart, designated as FIGS. 11E-A, 11E-B, and 11E-C, with directional modulus of elasticity values in mega. Pascals, obtained from the modulus mapping method testing and recorded for each square of the map 1172 of the area of interest 1130 of the disposable wearable absorbent article 1110.

A fifth step in the modulus mapping method is to plot and evaluate the directional modulus of elasticity values obtained from the modulus mapping method testing. The directional modulus of elasticity values are transferred to a spreadsheet such as Microsoft Excel™ and plotted as a surface contour plot. For the plot, set the maximum Z-axis value to truncate high modulus values resulting from seams, chassis bonds, and/or other such structural discontinuities in the area of interest that are unrelated to anchoring subsystem element(s). As an example, a maximum value of approximately six times the upper value of the directional modulus of elasticity in the lowest modulus region is useful for the directional modulus of elasticity values in the embodiment of FIG. 11E. Choose major value intervals to visually evaluate the plot for existing patterns of high and low directional modulii of elasticity in the area of interest. A minimum of five intervals should be used for this evaluation. For example, an interval value of approximately 0.25 mega Pascals is useful for the directional modulus of elasticity values in the embodiment of FIG. 11E. One skilled in the art of visual pattern recognition will understand that these values are representative and can be determined empirically for a given set of directional modulus of elasticity values.

Figure 11F:
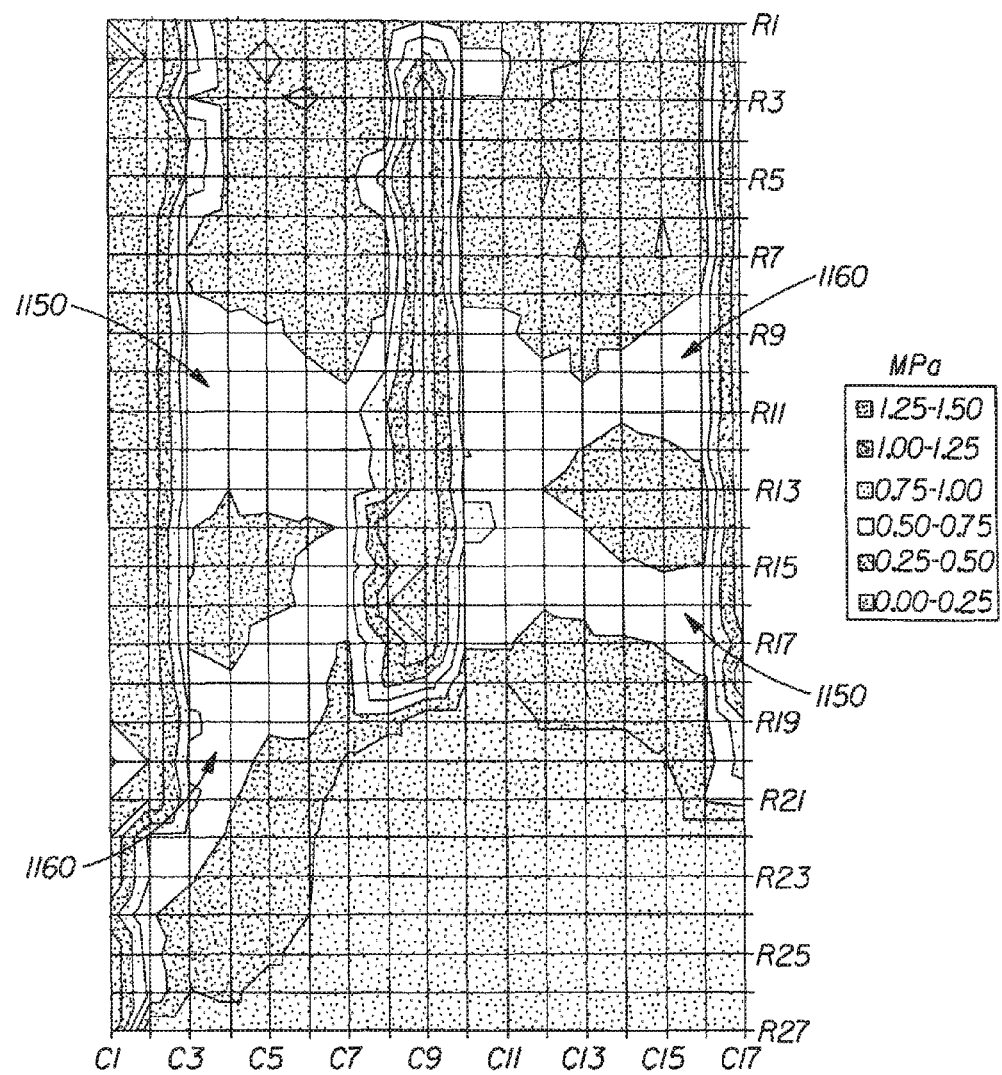
FIG. 11F illustrates an exemplary surface contour plot of the modulus of elasticity values of the chart of the embodiment of FIG. 11E, according to embodiments of the present disclosure.

FIG. 11F illustrates an exemplary surface contour plot of the directional modulus of elasticity values of the chart of the embodiment of FIG. 11E, as described above, for use in the modulus mapping method. In FIG. 11F, the maximum Z-axis values are truncated at 1.50 mega Pascals, which is six times the upper value of the directional modulus of elasticity in the lowest modulus region (e.g. 0.25 mega Pascals). The major value intervals are chosen to be 0.25 mega Pascals. One skilled in the art of visual pattern recognition will recognize that the plot of FIG. 11F illustrates the presence of an anchoring subsystem with a first SAM 1150 and a second SAM 1160, similar to the embodiment of FIGS. 1A-1C. Further, the plot of FIG. 11F indicates that each of the SAMs has a directional modulus of elasticity between 0.50 and 0.75 mega Pascals. Thus, the modulus mapping method can be used to detect the presence of one or more anchoring subsystem elements and to measure particular directional modulus of elasticity values for such elements.

Embodiments of the present disclosure include disposable wearable absorbent articles with anchoring subsystems that fit wearers well. The designs of these articles help prevent the articles from sagging or slipping down on a wearer. As a result, the disposable wearable absorbent articles of the present disclosure can feel comfortable, look attractive, and perform well as the articles tend to stay in place on wearers and not leak.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable wearable absorbent article comprising:
    a side with an area, wherein the area includes a first portion and a second portion, the second portion being disposed outside of the first portion;
    a chassis;
    an anchoring subsystem, including a first side anchoring member with a first middle, disposed along a first pathway within the first portion, and a second side anchoring member with a second middle, disposed along a second pathway within the first portion;
    wherein at least some of the first middle is coextensive with at least some of the second middle, and the first pathway is distinct from the second pathway; and
    wherein the coextensive area of the first middle and the second middle does not touch or overlap the chassis; and
    wherein the article further comprises a back waist edge and a front waist edge, and wherein the entirety of both the first side anchoring member and the second side anchoring member are longitudinally inboard of the back waist edge and the front waist edge.

2. The disposable wearable absorbent article of claim 1, further comprising a longitudinal centerline, a first end edge and a second end edge opposed to the first end edge;
    a first half disposed between the lateral centerline and the first end edge;
    a second half disposed between the lateral centerline and the second end edge;
    an absorbent core area; and
    wherein the first side anchoring member includes a first end disposed in the first half, outside of the absorbent core area, and a second end disposed in the second half, and the second side anchoring member includes a third end disposed in the first half, and a fourth end disposed in the second half.

3. The disposable wearable absorbent article of claim 2, wherein:
    the first end is disposed in the first portion at a first location; and
    the third end is disposed in the first portion at a third location that is longitudinally inboard to the first location.

4. The disposable wearable absorbent article of claim 2, wherein:
    the first end is disposed in the first portion at a first location; and
    the third end is disposed in the first portion at a third location that at least partially overlaps the first location.

5. The disposable wearable absorbent article of claim 2, wherein:
    the second end is disposed in the second portion at a second location; and
    the fourth end is disposed in the second portion at a fourth location that is longitudinally outboard from the second location.

6. The disposable wearable absorbent article of claim 2, wherein:
    the second end is disposed in the second portion at a second location; and
    the fourth end is disposed in the second portion at a fourth location that at least partially overlaps the second location.

7. The disposable wearable absorbent article of claim 2, wherein the side includes the anchoring subsystem, which is a side anchoring subsystem.

8. The disposable wearable absorbent article of claim 2, wherein at least one of the side anchoring members is configured as a geodesic.

9. The disposable wearable absorbent article of claim 2, wherein at least a portion of at least one of the side anchoring members is discrete from the side.

10. The disposable wearable absorbent article of claim 2, wherein at least a portion of at least one of the side anchoring members is attached to the side.

11. The disposable wearable absorbent article of claim 2, wherein at least a portion of at least one of the side anchoring members is embedded in the side.

12. The disposable wearable absorbent article of claim 2, wherein at least a portion of at least one of the side anchoring members is integral with the side.

* * * * *